United States Patent
Kwon et al.

(10) Patent No.: US 7,657,382 B2
(45) Date of Patent: Feb. 2, 2010

(54) METHOD OF DESIGNING PRIMER AND PROBE SETS, PRIMER AND PROBE SET DESIGNED BY THE METHOD, KIT COMPRISING THE SETS, COMPUTER READABLE MEDIUM RECORDED THEREON PROGRAM TO EXECUTE THE METHOD, AND METHOD OF IDENTIFYING TARGET SEQUENCE USING THE SETS

(75) Inventors: Tae-joon Kwon, Seongnam-si (KR); Kyu-sang Lee, Suwon-si (KR); Ji-young Oh, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 238 days.

(21) Appl. No.: 11/370,472

(22) Filed: Mar. 6, 2006

(65) Prior Publication Data
US 2006/0204996 A1 Sep. 14, 2006

(30) Foreign Application Priority Data
Mar. 8, 2005 (KR) .................. 10-2005-0019064

(51) Int. Cl.
*G01N 33/48* (2006.01)
*C12Q 1/68* (2006.01)
*C12P 19/34* (2006.01)

(52) U.S. Cl. ...................... 702/19; 435/6; 435/91.1; 435/91.2

(58) Field of Classification Search ............. None
See application file for complete search history.

(56) References Cited

U.S. PATENT DOCUMENTS

| 5,143,854 | A |   | 9/1992 | Pirrung et al. |
|---|---|---|---|---|
| 5,424,186 | A |   | 6/1995 | Fodor et al. |
| 5,445,934 | A |   | 8/1995 | Fodor et al. |
| 5,744,305 | A |   | 4/1998 | Fodor et al. |
| 6,090,555 | A | * | 7/2000 | Fiekowsky et al. ............ 435/6 |
| 6,144,388 | A | * | 11/2000 | Bornstein ................ 345/629 |
| 2006/0046246 | A1 | * | 3/2006 | Zeng et al. .................. 435/5 |

OTHER PUBLICATIONS

Notredame, C., et al., "T-Coffee: A Novel Method for Fast and Accurate Multiple Sequence Alignment," J. Mol. Biol. (2000) vol. 302, pp. 205-217.
Chenna, R., et al., "Multiple Sequence Alignment With The Clustal Series Of Programs," Nucleic Acids Research, (2003) vol. 31, No. 13, pp. 3497-3500.
Edgar, Robert C., "MUSCLE: Multiple Sequence Alignment With High Accuracy And High Throughput," Nucleic Acids Research, (2004) vol. 32, No. 5, pp. 1792-1797.

* cited by examiner

*Primary Examiner*—Young J Kim
(74) *Attorney, Agent, or Firm*—Cantor Colburn LLP

(57) ABSTRACT

A method of designing primer and probe sets for identification of target sequences by amplification and hybridization is provided. Also, primer and probe sets designed by the method, a kit comprising the sets, a computer readable medium recorded thereon a program to execute the method, and a method of identifying target sequences using the sets are provided. Accordingly, primer and probe sets capable of identifying rapidly and accurately a number of target sequences can be readily designed.

6 Claims, 6 Drawing Sheets

SEQUENCE LISTING

```
<160> NUMBER OF SEQ ID NOS: 77

<210> SEQ ID NO 1
<211> LENGTH: 1501
<212> TYPE: DNA
<213> ORGANISM: Streptococcus agalactiae

<400> SEQUENCE: 1
gacgaacgct ggcggcgtgc ctaatacatg caagtagaac gctgaggttt ggtgtttaca      60
ctagactgat gagttgcgaa cgggtgagta acgcgtaggt aacctgcctc atagcggggg     120
ataactattg gaaacgatag ctaataccgc ataagagtaa ttaacacatg ttagttattt     180
aaaaggagca attgcttcac tgtgagatgg acctgcgttg tattagctag ttggtgaggt     240
aaaggctcac caaggcgacg atacatagcc gacctgagag ggtgatcggc cacactggga     300
ctgagacacg gcccagactc ctacgggagg cagcagtagg gaatcttcgg caatggacgg     360
aagtctgacc gagcaacgcc gcgtgagtga agaaggtttt cggatcgtaa agctctgttg     420
ttagagaaga acgttggtag gagtggaaaa tctaccaagt gacggtaact aaccagaaag     480
ggacggctaa ctacgtgcca gcagccgcgg taatacgtag gtcccgagcg ttgtccggat     540
ttattgggcg taaagcgagc gcaggcggtt ctttaagtct gaagttaaag gcagtggctt     600
aaccattgta cgctttggaa actggaggac ttgagtgcag aaggggagag tggaattcca     660
tgtgtagcgg tgaaatgcgt agatatatgg aggaacaccg gtggcgaaag cggctctctg     720
gtctgtaact gacgctgagg ctcgaaagcg tggggagcaa acaggattag ataccctggt     780
agtccacgcc gtaaacgatg agtgctaggt gttaggccct tccggggct tagtgccgca     840 gctaacgcat taagcactcc gcctggggag tacgaccgca aggttgaaac tcaaaggaat     900 tgacggggc ccgcacaagc ggtggagcat gtggtttaat tcgaagcaac gcgaagaacc     960
ttaccaggtc ttgacatcct tctgaccggc ctagagatag gctttctctt cggagcagaa    1020
gtgacaggtg gtgcatggtt gtcgtcagct cgtgtcgtga gatgttgggt taagtcccgc    1080
aacgagcgca acccctattg ttagttgcca tcattaagtt gggcactcta gcgagactgc    1140
```

-continued

```
cggtaataaa ccggaggaag gtggggatga cgtcaaatca tcatgcccct tatgacctgg      1200
gctacacacg tgctacaatg gttggtacaa cgagtcgcaa gccggtgacg caagctaat       1260 ctcttaaagc caatctcagt tcggattgta ggctgcaact cgcctacatg aagtcggaat      1320
cgctagtaat cgcggatcag cacgccgcgg tgaatacgtt cccgggcctt gtacacaccg      1380
cccgtcacac cacgagagtt tgtaacaccc gaagtcggtg aggtaacctt ttaggagcca      1440
gccgcctaag gtgggataga tgattggggt gaagtcgtaa caaggtagcc gtatcggaag      1500
g                                                                     1501

<210> SEQ ID NO 2
<211> LENGTH: 1450
<212> TYPE: DNA
<213> ORGANISM: Streptococcus agalactiae

<400> SEQUENCE: 2
agaacgcgag gttggtgtac cacctagatc ctgatgagtt gcgaacgggt gagtaacgcg        60
taggtagcct gcctcatagc gggggataac tattggaaac gatagctaat accgcataag      120
agtaattaac acatgttagt tatttaaaag gagcaattgc ttcactgtga gatggacctg      180
cgttgtatta gctagttggt gaggtaaagg ctcaccaagg cgacgataca tagccgacct      240
gagagggtga tcggccacac tgggactgag acacggccca gactcctacg ggaggcagca      300
gtagggaatc ttcggcaatg gacggaagtc tgaccgagca acgccgcgtg agtgaagaag      360
gttttcggat cgtaaagctc tgttgttaga aagaacgttt ggtaggagtg aaaatctac       420 caagtgacgg taactaacca gaaagggacg gctaactacg tgccagcagc cgcggtaata      480
cgtaggtccc gagcgttgtc cggatttatt gggcgtaaag cgagcgcagg cggttctttta     540 agtctgaagt taaaggcagt ggcttaacca ttgtacgctt tggaaactgg aggacttgag      600
tgcagaaggg gagagtggaa ttccatgtgt agcggtgaaa tgcgtagata tatgaggaa       660 caccggtggc gaaagcggct ctctggtctg taactgacgc tgaggctcga aagcgtgggg      720
agcaaacagg attagatacc ctggtagtcc acgccgtaaa cgatgagtgc taggtgttag      780 gcccttttccg ggcgttagtg ccgcagctaa cgcattaagc actccgcctg ggagtacga      840 ccgcaaggtt gaaactcaaa ggaattgacg ggggcccgca caagcggtgg agcatgtggt      900
ttaattcgaa gcaacgcgaa gaaccttacc aggtcttgac atccttctga ccggcctaga      960
gataggcttt ctcttcggag cagaagtgac aggtggtgca tggttgtcgt cagctcgtgt     1020
cgtgagatgt tgggttaagt cccgcaacga gcgcaacccc tattgttagt tgccatcatt     1080
aagttgggca ctctagcgag actaccggta ataaaccgga ggaaggtggg gatgacgtca     1140
aatcatcatg ccccttatga cctgggctac acacgtgcta gaatggttgg tacaacgagt     1200
cgcaagccgg tgacgcaag ctaatctctt aaagccaatc tcagttcgga ttgtaggctg     1260
caactcgcct acatgaagtc ggaatcgcta gtaatcgcgg atcagcacgc cgcggtgaat     1320
acgttcccgg gccttgtaca caccgcccgt cacaccacga gagtttgtaa cacccgaagt     1380
cggtgaggta acctttttagg agccagccgc ctaaggtggg atagatgatt ggggtgaagt     1440
cgtaacaagg                                                            1450

<210> SEQ ID NO 3
<211> LENGTH: 1312
<212> TYPE: DNA
<213> ORGANISM: Streptococcus agalactiae
```

<400> SEQUENCE: 3

```
gcttgcacca gtctaatgag ttgcgaacgg gtgagtaacg cgtaggtaac ctaccttata      60
gcggggata actattggaa acgatagcta ataccgcatg aaagtagaag acccatgtca     120
tctacttaaa agggcaact gctccactat gagatgacc tgcgttgtat tagctagttg     180
gtgaggtaaa ggctcaccaa ggcgacgata catagccgac ctgagagggt gatcggccac     240
actgggactg agacacggcc cagactccta cgggaggcag cagtagggaa tcttcggcaa     300
tgggggaac cctgaccgag caacgccgcg tgagtgaaga aggttttcgg atcgtaaagc     360
tctgttgtta gagaagaacg gtaatgggag tggaaaatcc attacgtgac ggtaactaac     420
cagaaaggga cggctaacta cgtgccagca gccgcggtta tacgtaggtc ccgagtgttg     480
tccggattta ttgggcgtaa agcgagcgca ggcggtttga taagtctgaa gttaaaggct     540
gtggcttaac catagttcgc tttggaaact gtcaacttg agtgcagaag gggagagtgg     600
aattccatgt gtagcggtga aatgcgtaga tatatggagg aacaccggtg gcgaaagcgg     660
ctctctggtc tgtaactgac gctgaggctc gaaagcgtgg ggagcaaaca ggattagata     720
ccctggtagt ccacgccgta aacgatgagt gctaggtgtt aggcccttc cggggcttag     780
tgccggctag aacgcattaa gcactccgcc tggggagtac gaccgcaagg ttgaaactca     840
aaggaattga cggggcccg cacaagcggt ggagcatgtg gtttaattcg aagcaacgcg     900
aagaaccta ccaggtcttg acatccttct gaccggccta gagataggct ttctcttcgg     960
agcagaagtg acaggtggtg catggttgtc gtcagctcgt gtcgtgagat gttgggttaa    1020
gtcccgcaac gagcgcaacc cctattgtta gttgccatca ttaagttggg cactctagcg    1080
agactgccgg taataaaccg gaggaaggtg gggatgacgt caaatcatca tgccccttat    1140
gacctgggct acacacgtgc tacaatggtt ggtacaacga gtcgcaagcc ggtgacggca    1200
agctaatctc ttaaagccaa tctcagttcg gattgtaggc tgcaactcgc ctacatgaag    1260
tcggaatcgc tagtaatcgc ggatcagcac gccgcggtga atacgttccc gg            1312
```

<210> SEQ ID NO 4
<211> LENGTH: 1472
<212> TYPE: DNA
<213> ORGANISM: Streptococcus agalactiae

<400> SEQUENCE: 4

```
gacgaacgct ggcggcgtgc ctaatacatg caagtagaac gctgaggttt ggtgtttaca      60
ctagactgat gagttgcgaa cgggtgagta acgcgtaggt aacctgcctc atagcggggg     120
ataactattg gaaacgatag ctaataccgc ataagagtaa ttaacacatg ttggttattt     180
aaaaggagca attgcttcac tgtgagatgg acctgcgttg tattagctag ttggtgaggt     240
aaaggctcac caaggcgacg atacatagcc gacctgagag ggtgatcggc cacactggga     300
ctgagacacg gcccagactc ctacgggagg cagcagtagg gaatcttcgg caatggacgg     360
aagtctgacc gagcaacgcc gcgtgagtga agaaggtttt cggatcgtaa agctctgttg     420
ttagagaaga acgttggtag gagtggaaaa tctaccaagt gacggtaact aaccagaaag     480
ggacggctaa ctacgtgcca gcagccgcgg taatacgtag gtcccgagcg ttgtccggat     540
ttattgggcg taaagcgagc gcaggcggtt ctttaagtct gaagttaaag gcagtggctt     600
aaccattgta cgctttggaa actggaggac ttgagtgcag aaggggagag tggaattcca     660
tgtgtagcgg tgaaatgcgt agatatatgg aggaacaccg gtggcgaaag cggctctctg     720
gtctgtaact gacgctgagg ctcgaaagcg tggggagcaa acaggattag ataccctggt     780
```

| | |
|---|---|
| agtccacgcc gtaaacgatg agtgctaggt gttaggccct ttccggggct tagtgccgca | 840 |
| gctaacgcat taagcactcc gcctggggag tacgaccgca aggttgaaac tcaaaggaat | 900 |
| tgacggggc ccgcacaagc ggtggagcat gtggtttaat tcgaagcaac gcgaagaacc | 960 |
| ttaccaggtc ttgacatcct tctgaccggc ctagagatag gctttctctt cggagcagaa | 1020 |
| gtgacaggtg gtgcatggtt gtcgtcagct cgtgtcgtga gatgttgggt taagtcccgc | 1080 |
| aacgagcgca acccctattg ttagttgcca tcattaagtt gggcactcta gcgagactgc | 1140 |
| cggtaataaa ccggaggaag gtggggatga cgtcaaatca tcatgcccct tatgacctgg | 1200 |
| gctacacacg tgctacaatg gttggtacaa cgagtcgcaa gccggtgacg gcaagctaat | 1260 |
| ctcttaaagc caatctcagt tcggattgta ggctgcaact cgcctacatg aagtcggaat | 1320 |
| cgctagtaat cgcggatcag cacgccgcgg tgaatacgtt cccgggcctt gtacacaccg | 1380 |
| cccgtcacac cacgagagtt tgtaacaccc gaagtcggtg aggtaacctt ttaggagcca | 1440 |
| gccgcctaag gtgggataga tgattgggt ga | 1472 |

```
<210> SEQ ID NO 5
<211> LENGTH: 1508
<212> TYPE: DNA
<213> ORGANISM: Streptococcus bovis

<400> SEQUENCE: 5
```

| | |
|---|---|
| agagtttgat cctggctcag gacgaacgct ggcggcgtgc ctaatacatg caagtagaac | 60 |
| gctgaagact ttagcttgct aaagttggaa gagttgcgaa cgggtgagta acgcgtaggt | 120 |
| aacctgccta ctagcggggg ataactattg gaaacgatag ctaataccgc ataacagcat | 180 |
| ttaacacatg ttagatgctt gaaaggagca attgcttcac tagtagatgg acctgcgttg | 240 |
| tattagctag ttggtgaggt aacggctcac caaggctacg atacatagcc gacctgagag | 300 |
| ggtgatcggc cacactggga ctgagacacg gcccagactc ctacgggagg cagcagtagg | 360 |
| gaatcttcgg caatggggc aaccctgacc gagcaacgcc gcgtgagtga agaaggtttt | 420 |
| cggatcgtaa agctctgttg taagagaaga acgtgtgtga gagtggaaag ttcacacagt | 480 |
| gacggtaact taccagaaag ggacggctaa ctacgtgcca gcagccgcgg taatacgtag | 540 |
| gtcccgagcg ttgtccggat ttattgggcg taagcgagcg caggcggttt aataagtctg | 600 |
| aagttaaagg cagtggctta accattgttc gctttggaaa ctgttagact tgagtgcaga | 660 |
| agggagagt ggaattccat gtgtagcggt gaaatgcgta gatatatgga ggaacaccgg | 720 |
| tggcgaaagc ggctctctgg tctgtaactg acgctgaggc tcgaaagcgt ggggagcaaa | 780 |
| caggattaga taccctggta gtccacgccg taaacgatga gtgctaggtg ttaggccctt | 840 |
| tccggggctt agtgccgcag ctaacgcatt aagcactccg cctggggagt acgaccgcaa | 900 |
| ggttgaaact caaaggaatt gacggggcc cgcacaagcg gtggagcatg tggtttaatt | 960 |
| cgaagcaacg cgaagaacct taccaggtct tgacatcccg atgctattcc tagagatagg | 1020 |
| aagtttcttc ggaacatcgg tgacaggtgg tgcatggttg tcgtcagctc gtgtcgtgag | 1080 |
| atgttgggtt aagtcccgca acgagcgcaa ccctattgt tagttgccat cattaagttg | 1140 |
| ggcactctag cgagactgcc ggtaataaac cggaggaagg tggggatgac gtcaaatcat | 1200 |
| catgcccctt atgacctggg ctacacacgt gctacaatgg ttggtacaac gagtcgcgag | 1260 |
| tcggtgacgg caagcaaatc tcttaaagcc aatctcagtt cggattgtag gctgcaactc | 1320 |
| gcctacatga agtcggaatc gctagtaatc gcggatcagc acgccgcggt gaatacgttc | 1380 |

```
ccgggccttg tacacaccgc ccgtcacacc acgagagttt gtaacacccg aagtcggtga    1440 ggtaacctttt tggagccagc cgcctaaggt gggatagatg attggggtga agtcgtaaca    1500
aggtaacc                                                             1508
```

<210> SEQ ID NO 6
<211> LENGTH: 1508
<212> TYPE: DNA
<213> ORGANISM: Streptococcus bovis

<400> SEQUENCE: 6

```
agagtttgat cctggctcag gacgaacgct ggcggcgtgc ctaatacatg caagtacaac     60
gctgaagact ttagcttgct aaagttggaa gagttgcgaa cgggtgagta acgcgtaggt    120
aacctgccta ctagcggggg ataactattg gaaacgatag ctaataccgc ataacagcat    180
ttaacacatg ttagatgctt gaaaggagca attgcttcac tagtagatgg acctgcgttg    240
tattagctag ttggtgaggt aacggctcac caaggctacg atacatagcc gacctgagag    300
ggtgatcggc cacactggga ctgagacacg gcccagactc ctacgggagg cagcagtagg    360
gaatcttcgg caatggggc aaccctgacc gagcaacgcc gcgtgagtga agaaggtttt    420
cggatcgtaa agctctgttg taagagaaga acgtgtgtga gagtggaaag ttcacacagt    480
gacggtaact taccagaaag ggacggctaa ctacgtgcca gcagccgcgg taatacgtag    540
gtcccgagcg ttgtccggat ttattgggcg taaagcgagc gcaggcggtt taataagtct    600
gaagttaaag gcagtggctt aaccattgtt cgctttggaa actgttagac ttgagtgcag    660
aaggggagag tggaattcca tgtgtagcgg tgaaatgcgt agatatatgg aggaacaccg    720
gtggcgaaag cggctctctg gtctgtaact gacgctgagg ctcgaaagcg tggggagcaa    780
acaggattag ataccctggt agtccacgcc gtaaacgatg agtgctaggt gttaggccct    840
ttccggggct tagtgccgca gctaacgcat taagcactcc gcctggggag tacgaccgca    900
aggttgaaac tcaaaggaat tgacggggc ccgcacaagc ggtggagcat gtggtttatt    960
cgaagcaacg cgaagaacct taccaggtct tgacatcccg atgctattcc tagagatagg   1020
aagtttcttc ggaacatcgg tgacaggtgg tgcatggttg tcgtcagctc gtgtcgtgag   1080
atgttgggtt aagtcccgca acgagcgcaa cccctattgt tagttgccat cattaagttg   1140
ggcactctag cgagactgcc ggtaataaac cggaggaagg tggggatgac gtcaaatcat   1200
catgcccctt atgacctggg ctacacacgt gctacaatgg ttggtacaac gagtcgcgag   1260
tcggtgacgg caagcaaatc tcttaaagcc aatctcagtt cggattgtag gctgcaactc   1320
gcctacatga agtcggaatc gctagtaatc gcggatcagc acgccgcggt gaatacgttc   1380
ccgggccttg tacacaccgc ccgtcacacc acgagagttt gtaacacccg aagtcggtga   1440 ggtaacctttt tggagccagc cgcctaaggt gggatagatg attggggtga agtcgtaaca   1500
aggtaacc                                                             1508
```

<210> SEQ ID NO 7
<211> LENGTH: 1508
<212> TYPE: DNA
<213> ORGANISM: Streptococcus bovis

<400> SEQUENCE: 7

```
agagtttgat cctggctcag gacgaacgct ggcggcgtgc ctaatacatg caagtagaac     60
gctgaagact ttagcttgct aaagttggaa gagttgcgaa cgggtgagta acgcgtaggt    120
aacctgccta ctagcggggg ataactattg gaaacgatag ctaataccgc ataacagcat    180
```

```
ttaacacatg ttagatgctt gaaaggagca attgcttcac tagtagatgg acctgcgttg      240
tattagctag ttggtgaggt aacggctcac caaggcgacg atacatagcc gacctgagag      300
ggtgatcggc cacactggga ctgagacacg gcccagactc ctacgggagg cagcagtagg      360
gaatcttcgg caatggggc aaccctgacc gagcaacgcc gcgtgagtga agaaggtttt       420
cggatcgtaa agctctgttg taagagaaga acgtgtgtga gagtggaaag ttcacacagt      480
gacggtaact taccagaaag ggacggctaa ctacgtgcca gcagccgcgg taatacgtaa      540
gtcccgagcg ttgtccggat ttattgggcg taagcgagcg caggcggttt aataagtctg      600
aagttaaagg cagtggctta accattgttc gctttggaaa ctgttagact tgagtgcaga      660
aggggagagt ggaattccat gtgtagcggt gaaatgcgta gatatatgga ggaacaccgg      720
tggcgaaagc ggctctctgg tctgtaactg acgctgaggc tcgaaagcgt ggggagcaaa      780
caggattaga taccctggta gtccacgccg taaacgatga gtgctaggtg ttaggcccctt     840 tccgggcctt agtgccgcag ctaacgcatt aagcactccg cctggggagt acgaccgcaa      900
ggttgaaact caaaggaatt gacggggggcc cgcacaagcg gtggagcatg tggtttaatt    960
cgaagcaacg cgaagaacct taccaggtct tgacatcccg atgctattcc tagagatagg     1020
aagtttcttc ggaacatcgg tgacaggtgg tgcatggttg tcgtcagctc gtgtcgtgag     1080
atgttgggtt aagtcccgca acgagcgcaa cccctattgt tagttgccat cattaagttg     1140
ggcactctag cgagactgcc ggtaataaac cggaggaagg tggggatgac gtcaaatcat     1200
catgcccctt atgacctggg ctacacacgt gctacaatgg ttggtacaac gagtcgcgag     1260
tcggtgacgg caagcaaatc tcttaaagcc aatctcagtt cggattgtag gctgcaactc     1320
gcctacatga agtcggaatc gctagtaatc gcggatcagc acgccgcggt gaatacgttc     1380
ccgggccttg tacacaccgc ccgtcacacc acgagagttt gtaacacccg aagtcggtga     1440
ggtaaccttt tggagccagc cgcctaaggt gggatagatg attggggtga agtcgtaaca     1500
aggtaacc                                                               1508
```

<210> SEQ ID NO 8
<211> LENGTH: 1508
<212> TYPE: DNA
<213> ORGANISM: Streptococcus bovis

<400> SEQUENCE: 8

```
agagtttgat cctggctcag gacgaacgct ggcggcgtgc ctaatacatg caagtagaac       60
gctgaagact ttagcttgct aaagttggaa gagttgcgaa cgggtgagta acgcgtaggt      120
aacctgccta ctaacggggg ataactattg gaaacgatag ctaataccgc ataacagcat      180
ttaacacatg ttagatgctt gaagggagca attgcttcac tagtagatgg acctgcgttg      240
tattagctag ttggtgaggt aacggctcac caaggcgacg atacatagcc gacctgagag      300
ggtgatcggc cacactggga ctgagacacg gcccagactc ctacgggagg cagcagtagg      360
gaatcttcgg caatggggc aaccctgacc gagcaacgcc gcgtgagtga agaaggtttt       420
cggatcgtaa agctctgttg taagagaaga acgtgtgtga gagtggaaag ttcacacagt      480
gacggtaact taccagaaag ggacggctaa ctacgtgcca gcagccgcgg taatacgtag      540
gtcccgagcg ttgtccggat ttattgggcg taagcgagcg caggcggttt aataagtctg      600
aagttaaagg cagtggctta accattgttc gctttggaaa ctgttagact tgagtgcaga      660
aggggagagt ggaattccat gtgtagcggt gaaatgcgta gatatatgga ggaacaccgg      720
```

```
tggcgaaagc ggctctctgg tctgtaactg acgctgaggc tcgaaagcgt ggggagcaaa      780
caggattaga taccctggta gtccacgccg taaacgatga gtgctaggtg ttaggccctt      840
tccggggctt agtgccgcag ctaacgcatt aagcactccg cctggggagt acgaccgcaa      900
ggttgaaact caaaggaatt gacggggggcc cgcacaagcg gtggagcatg tggtttaatt   960
cgaagcaacg cgaagaacct taccaggtct tgacatcccg atgctattcc tagagatagg    1020
aagtttcttc ggaacatcgg tgacaggtgg tgcatggttg tcgtcagctc gtgtcgtgag   1080
atgttgggtt aagtcccgca acgagcgcaa ccctattgt tagttgccat cattaagttg    1140
ggcactctag cgagactgcc ggtaataaac cggaggaagg tggggatgac gtcaaatcat   1200
catgcccctt atgacctggg ctacacacgt gctacaatgg ttggtacaac gagtcgcgag   1260
tcggtgacgg caagcaaatc tcttaaagcc aatctcagtt cggattgtag ctgcaactc    1320 gcctacatga agtcggaatc gctagtaatc gcggatcagc acgccgcggt gaatacgttc   1380
ccgggccttg tacaccgc ccgtcacacc acgagagttt gtaacacccg aagtcggtga     1440
ggtaaccttt tggagccagc cgcctaaggt gggatagatg attggggtga agtcgtaaca   1500
aggtaacc                                                              1508

<210> SEQ ID NO 9
<211> LENGTH: 1468
<212> TYPE: DNA
<213> ORGANISM: Streptococcus bovis

<400> SEQUENCE: 9
gagtttgatc ctggctcagg acgaacgctg gcggcgtgcc taatacatgc aagtagaacg     60
ctgaagactt agcttgcta aagttggaag agttgcgaac gggtgagtaa cgcgtaggta    120
acctgcctac tagcggggga taactattgg aaacgatagc taataccgca taacagcttt   180
taactcatgt taggagcttg aaagatgcaa ttgcatcact agtagatgga cctgcgttgt   240
attagctagt tggtgaggta acggctcacc aaggcgacga tacatagccg acctgagagg    300
gtgatcggcc acactgggac tgagacacg cccagactcc tacgggaggc agcagtaggg    360
aatcttcggc aatgggggca accctgaccg agcaacgccg cgtgagtgaa aaggttttc    420 ggatcgtaaa gctctgttgt aagagaagaa cgtgtgtgag agtggaaagt tcacacagtg   480
acggtaactt accagaaagg gacggctaac tacgtgccag cagccgcggt aatacgtagg   540
tcccgagcgt tgtccggatt tattgggcgt aaagcgagcg caggcggttt aataagtctg   600
aagttaaagg cagtggctta accattgttc gctttggaaa ctgttagact tgagtgcaga   660
aggggagagt ggaattccat gtgtagcggt gaaatgcgta gatatatgga ggaacaccgg   720
tggcgaaagc ggctctctgg tctgtaactg acgctgaggc tcgaaagcgt ggggagcaaa   780
caggattaga taccctggta gtccacgccg taaacgatga gtgctaggtg ttaggccctt   840
tccggggctt agtgccgcag ctaacgcatt aagcactccg cctggggagt acgaccgcaa   900
ggttgaaact caaaggaatt gacggggggcc cgcacaagcg gtggagcatg tggtttaatt  960
cgaagcaacg cgaagaacct taccaggtct tgacatcccg atgctattcc tagagatagg  1020
aagtttcttc ggaacatcgg tgacaggtgg tgcatggttg tcgtcagctc gtgtcgtgag  1080
atgttgggtt aagtcccgca acgagcgcaa ccctattgt tagttgccat cattaagttg   1140
ggcactctag cgagactgcc ggtaataaac cggaggaagg tggggatgac gtcaaatcat  1200
catgcccctt atgacctggg ctacacacgt gctacaatgg ttggtacaac gagtcgcgag  1260
tcggtgacgg caagcaaatc tcttaaagcc aatctcagtt cggattgtag ctgcaactc   1320
```

```
gcctacatga agtcggaatc gctagtaatc gcggatcagc acgccgcggt gaatacgttc    1380
ccgggccttg tacacaccgc ccgtcacacc acgagagttt gtacacccga agtcggtgag    1440
gtaccctttt acgagccagc cgcctaag                                       1468

<210> SEQ ID NO 10
<211> LENGTH: 1513
<212> TYPE: DNA
<213> ORGANISM: Streptococcus bovis

<400> SEQUENCE: 10
agagtttgat cctggctcag gacgaacgct ggcggcgtgc ctaatacatg caagtagaac      60
gctgaagact ttagcttgct aaagttggaa gagttgcgaa cgggtgagta acgcgtaggt     120
aacctgccta ctagcggggg ataactattg gaaacgatag ctaataccgc ataacagctt     180
ttaactcatg ttaggagctt gaaagatgca attgcttcac tagtagatgg acctgcgttg     240
tattagctag ttggtgaggt aacggctcac caaggcgacg atacatagcc gacctgagag     300
ggtgatcggc cacactggga ctgagacacg gcccagactc ctacgggagg cagcagtagg     360
gaatcttcgg caatggggggc aaccctgacc gagcaacgcc gcgtgagtga agaaggtttt     420
cggatcgtaa agctctgttg taagagaaga acgtgtgtga gagtggaaag ttcacacagt     480
gacggtaact taccagaaag ggacggctaa ctacgtgcca gcagccgcgg taatacgtag     540
gtcccgagcg ttgtccggat ttattgggcg taaagtgagc gcaggcggtt taataagtct     600
gaagttaaag gcagtggctt aaccattgtt cgctttggaa actgttagac ttgagtgcat     660 aggggggagag tggaattcca tgtgtagcgg tgaaatgcgt agatatatgg aggaacaccg     720
gtggcgaaag cggctctctg gtctgtaact gacgctgagg ctcgaaagcg tggggagcaa     780
acaggattag ataccctggt agtccacgcc gtaaacgatg agtgctaggt gttaggccct     840
ttccggggct tagtgccgca gctaacgcat taagcactcc gcctgggagt acgaccgca     900 aggttgaaac tcaaaggaat tgacgggggc cgcacaagcg gtggagcat gtggtttaat     960 tcgaagcaac gcgaagaacc ttaccaggtc ttgacatccc gatgctattc ctagagatag    1020
gaagtttctt cggaacatcg gtgacaggtg gtgcatggtt gtcgtcagct cgtgtcgtga    1080
gatgttgggt taagtcccgc aacgagcgca acccctattg ttagttgcca tcattaagtt    1140
gggcactcta gcgagactgc cggtaataaa ccggaggaag gtgggatga cgtcaaatca    1200 tcatgcccct tatgacctgg gctacacacg tgctacaatg gttggtacaa cgagtcgcga    1260
gtcggtgacg gcaagcaaat ctcttaaagc caatctcagt tcggattgta ggctgcaact    1320
cgcctacatg aagtcggaat cgctagtaat cgcggatcag cacgccgcgg tgaatacgtt    1380
cccgggcctt gtacacaccg cccgtcacac cacgagagtt tgtaacaccc gaagtcggtg    1440 aggtaaccctt ttaggagcca gccgcctaag gtgggataga tgattggggt gaagtcgtaa    1500
caaggtagcc gta                                                       1513

<210> SEQ ID NO 11
<211> LENGTH: 1500
<212> TYPE: DNA
<213> ORGANISM: Streptococcus bovis

<400> SEQUENCE: 11
tgatcctggc tcaggacgaa cgctggcggc gtgcctaata catgcaagta gaacgctgaa      60
gactttagct tgctaaagtt ggaagagttg cgaacgggtg agtaacgcgt aggtaacctg     120
```

```
cctactagcg ggggataact attggaaacg atagctaata ccgcataaca gcatttaacc    180
catgttagat gcttgaaagg agcaattgct tcactagtag atggacctgc gttgtattag    240
ctagttggtg aggtaacggc tcaccaaggc gacgatacat agccgacctg agagggtgat    300
cggccacact gggactgaga cacggcccag actcctacgg gaggcagcag tagggaatct    360
tcggcaatgg gggcaaccct gaccgagcaa cgccgcgtga gtgaagaagg ttttcggatc    420
gtaaagctct gttgtaagag aagaacgtgt gtgagagtgg aaagttcaca cagtgacggt    480
aacttaccag aaagggacgg ctaactacgt gccagcagcc gcggtaatac gtaggtcccg    540
agcgttgtcc ggatttattg ggcgtaaagc gagcgcaggc ggtttaataa gtctgaagtt    600
aaaggcagtg gcttaaccat tgttcgcttt ggaaactgtt agacttgagt gcagaagggg    660
agagtggaat tccatgtgta gcggtgaaat gcgtagatat atggaggaac accggtggcg    720
aaagcggctc tctggtctgt aactgacgct gaggctcgaa agcgtgggga gcaaacagga    780
ttagataccc tggtagtcca cgccgtaaac gatgagtgct aggtgttagg ccctttccgg    840
ggcttagtgc cgcagctaac gcattaagca ctccgcctgg ggagtacgac cgcaaggttg    900
aaactcaaag gaattgacgg gggcccgcac aagcggtgga gcatgtggtt taattcgaag    960
caacccgagg aaccttacca ggtcttgaca tcccgatgct attcctagag ataggaagtt   1020
tcttcggaac atcggtgaca ggtggtgcat ggttgtcgtc agctcgtgtc gtgagatgtt   1080
gggttaagtc ccgcaacgag cgcaaccccct attgttagtt gccatcatta agttgggcac   1140
tctagcgaga ctgccggtaa taaaccggag gaaggtgggg atgacgtcaa atcatcatgc   1200
cccttatgac ctgggctaca cacgtgctac aatggttggt acaacgagtc gcgagtcggt   1260
gacggcaagc aaatctctta aagccaatct cagttcggat tgtaggctgc aactcgccta   1320
catgaagtcg gaatcgctag taatcgcgga tcagcacgcc gcggtgaata cgttcccggg   1380
ccttgtacac accgcccgtc acaccacgag agtttgtaac acccgaagtc ggtgaggtaa   1440
ccttttagga gccagccgcc taaggtggga tagatgattg gggtgaagtc gtaacaaggt   1500
```

<210> SEQ ID NO 12
<211> LENGTH: 1457
<212> TYPE: DNA
<213> ORGANISM: Streptococcus bovis
<400> SEQUENCE: 12

```
agcaagtaga acgctgaaga ccttagcttg ctaaagttgg aagagttgcg aacgggtgag     60
taacgcgtag gtaacctgcc tactagcggg ggataactat tggaaacgat agctaatacc    120
gcataacagc atttaacaca tgttagatgc ttgaaaggag caattgcttc actagtagat    180
ggacctgcgt tgtattagct agttggtgag gtaacggctc accaaggcga cgatacatag    240
ccgacctgag ggtgatcg gccacactgg gactgagaca cggcccagac tcctacggga    300
ggcagcagta gggaatcttc ggcaatgggg caaccctga ccgagcaacg ccgcgtgagt    360
gaagaaggtt ttcggatcgt aaagctctgt tgtaagagaa gaacgtgtgt gagagtggaa    420
agttcacaca gtgacggtaa cttaccagaa agggacggct aactacgtgc cagcagccgc    480
ggtaatacgt aggtcccgag cgttgtccgg atttattggg cgttaagcga gcgcaggcgg    540
tttaataagt ctgaagttaa aggcagtggc ttaaccattg ttcgctttgg aaactgttag    600
acttgagtgc agaaggggag agtggaattc catgtgtagc ggtgaaatgc gtagatatat    660
ggaggaacac cggtggcgaa agcggctctc tggtctgtaa ctgacgctga ggctcgaaag    720
cgtggggagc aaacaggatt agataccctg gtagtccacg ccgtaaacga tgagtgctag    780
```

```
gtgttaggcc ctttccgggg cttagtgccg cagctaacgc attaagcact ccgcctgggg    840
agtacgaccg caaggttgaa actcaaagga attgacgggg cccgcacaa gcggtggagc    900 atgtggttta attcgaagca accgcaagaa ccttaccagg tcttgacatc ccgatgctat    960
tcttagagat agggtttctc ttcggaacat cggtgacagg tggtgcatgg ttgtcgtcag   1020
ctcgtgttgt gagatgttgg gttaagtccc gcaaccagcc caaccccctat tgttagttgc   1080 catcataagg ttgggcacct tagcgagact gccggtaata aaccgaagga aggtggggat   1140
gacgtcaaat catcatgccc cttatgacct gggctacaca cgtgctacaa tggttggtac   1200
aacgagtcgc gagtcggtga cggcaagcaa atctcttaaa gccaatctca gttcggattg   1260
taggctgcaa ctcgcctaca tgaagtcgga atcgctagta atcgcggatc agcacgccgc   1320
ggtgaatacg ttcccgggcc ttgtacacac cgcccgtcac accacgagag tttgtaacac   1380
ccgaagtcgg tgaggtaacc ttttaggagc cagccgccta aggtgggata gatgattggg   1440
gtgaagtcgt aacaagg                                                  1457

<210> SEQ ID NO 13
<211> LENGTH: 1540
<212> TYPE: DNA
<213> ORGANISM: Streptococcus bovis

<400> SEQUENCE: 13
gagtttgatc ctggctcagg acgaacgctg gcggcgtgcc taatacatgc aagtagaacg     60
ctgaagactt tagcttgcta aagttggaag agttgcgaac gggtgagtaa cgcgtaggta    120
acctgcctac tagcgggggga taactattgg aaacgatagc taataccgca taacagcatt    180
taacacatgt tagatgcttg aaaggagcaa ttgcttcact agtagatgga cctgcgttgt    240
attagctagt tggtgaggta agcggctcac caaggcgacg atacatagcc gacctgagag    300
ggtgatcggc cacactggga ctgagacacg gcccagactc ctacgggagg cagcagtagg    360
gaatcttcgg caatggggc aaccctgacc gagcaacgcc gcgtgagtga agaaggtttt    420
cggatcgtaa agctctgttg taagagaaga acgtgtgtga gagtggaaag ttcacacagt    480
gacggtaact taccagaaag ggacggctaa ctacgtgcca gcagccgcgg taatacgtag    540
gtcccgagcg ttgtccggat ttattgggcg taaagcgagc gcaggcggtt taataagtct    600
gaagttaaag gcagtggctt aaccattgtt cgctttggaa actgttagac ttgagtgcag    660
aaggggagag tggaattcca tgtgtagcgg tgaaatgcgt agatatatgg aggaacaccg    720
gtggcgaaag cggctctctg gtctgtaact gacgctgagg ctcgaaagcg tggggagcaa    780
acaggattag ataccctggt agtccacgcc gtaaacgatg agtgctaggt gttaggccct    840
ttccggggct tagtgccgca gctaacgcat taagcactcc gcctggggag tacgaccgca    900
aggttgaaac tcaaaggaat tgacgggggc ccgcacaagc ggtggagcat gtggtttaat    960
tcgaagcaac gcgaagaacc ttaccaggtc ttgacatccc gatgctattc ctagagatag   1020
gaagtttctt cggaacatcg tgacaggtg tgcatggtt gtcgtcagct cgtgtcgtga    1080
gatgttgggt taagtcccgc aacgagcgca accctattg ttagttgcca tcattaagtt   1140
gggcactcta gcgagactgc cggtaataaa ccggaggaag gtggggatga cgtcaaatca   1200
tcatgcccct tatgacctgg gctacacacg tgctacaatg gttggtacaa cgagtcgcga   1260
gtcggtgacg gcaagcaaat ctcttaaagc caatctcagt tcggattgta ggctgcaact   1320
cgcctacatg aagtcggaat cgctagtaat cgcggatcag cacgccgcgg tgaatacgtt   1380
```

-continued

```
cccgggcctt gtacacaccg cccgtcacac cacgagagtt tgtaacaccc gaagtcggtg    1440
aggtaacctt ttggagccag ccgcctaagg tgggatagat gattggggtg aagtcgtaac    1500
aaggtagccg tatcggaagg tgcggctgga tcacctcctt                         1540
```

<210> SEQ ID NO 14
<211> LENGTH: 1539
<212> TYPE: DNA
<213> ORGANISM: Streptococcus bovis

<400> SEQUENCE: 14

```
gagtttgatc ctggctcagg acgaacgctg gcggcgtgcc taatacatgc aagtagaacg      60
ctgaagactt tagcttgcta aagttggaag agttgcgaac gggtgagtaa cgcgtaggta     120
acctgcctac tagcggggga taactattgg aaacgatagc taataccgca taacagcatt     180
taacacatgt tagatgcttg aaaggagcaa ttgcttcact agtagatgga cctgcgttgt     240
attagctagt tggtgaggta acggctcacc aaggcgacga tacatagccg acctgagagg     300
gtgatcggcc acactgggac tgagacacgg cccagactcc tacgggaggc agcagtaggg     360
aatcttcggc aatgggggca accctgaccg agcaacgccg cgtgagtgaa gaaggttttc     420
ggatcgtaaa gctctgttgt aagagaagaa cgtgtgtgag agtggaaagt tcacacagtg     480
acggtaactt accagaaagg gacggctaac tacgtgccag cagccgcggt aatacgtagg     540
tcccgagcgt tgtccggatt tattgggcgt aaagcgagcg caggcggttt aataagtctg     600
aagttaaagg cagtggctta accattgttc gctttggaaa ctgttagact tgagtgcaga     660
aggggagagt ggaattccat gtgtagcggt gaaatgcgta gatatatgga ggaacaccgg     720
tggcgaaagc ggctctctgg tctgtaactg acgctgaggc tcgaaagcgt ggggagcaaa     780
caggattaga taccctggta gtccacgccg taaacgatga gtgctaggtg ttaggccctt     840
tccgggcttt agtgccgcag ctaacgcatt aagcactccg cctggggagt acgaccgcaa     900
ggttgaaact caaaggaatt gacggggggcc cgcacaagcg gtggagcatg tggtttaatt     960
cgaagcaacg cgaagaacct taccaggtct tgacatcccg atgctattcc tagagatagg    1020
aagtttcttc ggaacatcgg tgacaggtgg tgcatggttg tcgtcagctc gtgtcgtgag    1080
atgttgggtt aagtcccgca acgagcgcaa cccctattgt tagttgccat cattaagttg    1140
ggcactctag cgagactgcc ggtaataaac cggaggaagg tggggatgac gtcaaatcat    1200
catgcccctt atgacctggg ctacacacgt gctacaatgg ttggtacaac gagtcgcgag    1260
tcggtgacgg caagcaaatc tcttaaagcc aatctcagtt cggattgtag gctgcaactc    1320
gcctacatga agtcggaatc gctagtaatc gcggatcagc acgccgcggt gaatacgttc    1380
ccgggccttg tacacaccgc ccgtcacacc acgagagttt gtaacacccg aagtcggtga    1440
ggtaaccttt tggagccagc cgcctaaggt gggatagatg attggggtga agtcgtaaca    1500
aggtagccgt atcggaaggt gcggctggat caccctcctt                          1539
```

<210> SEQ ID NO 15
<211> LENGTH: 1539
<212> TYPE: DNA
<213> ORGANISM: Streptococcus bovis

<400> SEQUENCE: 15

```
gagtttgatc ctggctcagg acgaacgctg gcggcgtgcc taatacatgc aagtagaacg      60
ctgaagactt tagcttgcta aagttggaag agttgcgaac gggtgagtaa cgcgtaggta     120
acctgcctac tagcggggga taactattgg aaacgatagc taataccgca taacagcatt     180
```

-continued

| | |
|---|---|
| taacacatgt tagatgcttg aaaggagcaa ttgcttcact agtagatgga cctgcgttgt | 240 |
| attagctagt tggtgaggta acggctcacc aaggcgacga tacatagccg acctgagagg | 300 |
| gtgatcggcc acactgggac tgagacacgg cccagactcc tacgggaggc agcagtaggg | 360 |
| aatcttcggc aatgggggca accctgaccg agcaacgccg cgtgagtgaa gaaggttttc | 420 |
| ggatcgtaaa gctctgttgt aagagaagaa cgtgtgtgac agtggaaagt tcacacagtg | 480 |
| acggtaactt accagaaagg gacggctaac tacgtgccag cagccgcggt aatacgtagg | 540 |
| tcccgagcgt tgtccggatt tattgggcgt aaagcgagcg caggcggttt aataagtctg | 600 |
| aagttaaagg cagtggctta accattgttc gctttggaaa ctgttagact tgagtgcaga | 660 |
| aggggagagt ggaattccat gtgtagcggt gaaatgcgta gatatatgga ggaacaccgg | 720 |
| tggcgaaagc ggctctctgg tctgtaactg acgctgaggc tcgaaagcgt ggggagcaaa | 780 |
| caggattaga taccctggta gtccacgccg taaacgatga gtgctaggtg ttaggccctt | 840 |
| tccggggctt agtgccgcag ctaacgcatt aagcactccg cctggggagt acgaccgcaa | 900 |
| ggttgaaact caaaggaatt gacggggggcc cgcacaagcg gtggagcatg tggtttaatt | 960 |
| cgaagcaacg cgaagaacct taccaggtct tgacatcccg atgctattcc tagagatagg | 1020 |
| aagtttcttc ggaacatcgg tgacaggtgg tgcatggttg tcgtcagctc gtgtcgtgag | 1080 |
| atgttgggtt aagtcccgca acgagcgcaa cccctattgt tagttgccat cattaagttg | 1140 |
| ggcactctag cgagactgcc ggtaataaac cggaggaagg tggggatgac gtcaaatcat | 1200 |
| catgcccctt atgacctggg ctacacacgt gctacaatgg ttggtacaac gagtcgcgag | 1260 |
| tcggtgacgg caagcaaatc tcttaaagcc aatctcagtt cggattgtag ctgcaactc | 1320 |
| gcctacatga agtcggaatc gctagtaatc gcggatcagc acgccgcggt gaatacgttc | 1380 |
| ccgggccttg tacaccgc ccgtcacacc acgagagttt gtaacacccg aagtcggtga | 1440 |
| ggtaaccttt tggagccagc cgcctaaggt gggatagatg attggggtga agtcgtaaca | 1500 |
| aggtagccgt atcggaaggt gcggctggat cacctccttt | 1539 |

<210> SEQ ID NO 16
<211> LENGTH: 1481
<212> TYPE: DNA
<213> ORGANISM: Streptococcus bovis

<400> SEQUENCE: 16

| | |
|---|---|
| ctggcggcgt gcctaataca tgcaagtgga acgcatgatt gataccggag cttgctccac | 60 |
| cattaatcat gagtcgcgaa cgggtgagta acgcgtaggt aacctacctc atagcggggg | 120 |
| ataactattg gaaacgatag ctaataccgc ataacagtat ttatcgcatg gtaaatgctt | 180 |
| gaaaggagca actgcttcac tatgagatgg acctgcgttg tattagctag ttggtggggt | 240 |
| aacggctcac caaggcatcg atacatagcc gacctgagag ggtgatcggc cacactggga | 300 |
| ctgagacacg gcccagactc ctacgggagg cagcagtagg gaatcttcgg caatgggggg | 360 |
| aaccctgacc gagcaacgcc gcgtgagtga agaaggtttt cggatcgtaa agctctgttg | 420 |
| taagagaaga acgtgtgtga gagtggaaag ttcacacagt gacggtaact taccagaaag | 480 |
| ggacggctaa ctacgtgcca gcagccgcgg taatacgtag gtcccgagcg ttgtccggat | 540 |
| ttattgggcg taaagcgagc gcaggcggtt tgataagtct gaagtaaaag gctgtggctt | 600 |
| aaccatagta tgctttggaa actgtcaaac ttgagtgcag aaggggagag tggaattcca | 660 |
| tgtgtagcgg tgaaatgcgt agatatatgg aggaacaccg gtggcgaaag cggctctctg | 720 |

-continued

```
gtctgtaact gacgctgagg ctcgaaagcg tggggagcaa acaggattag atacctggt      780 agtccacgcc gtaaacgatg agtgctaggt gttgggtcct ttccgggact cagtgccgta     840
gctaacgcat taagcactcc gcctggggag tacgaccgca aggttgaaac tcaaaggaat     900 tgacggggc ccgcacaagc ggtggagcat gtggtttaat tcgaagcaac gcgaagaacc     960
ttaccaggtc ttgacatccc agtgaccgtc ctagagatag gattttctt cggaacactg    1020 gagacaggtg gtgcatggtt gtcgtcagct cgtgtcgtga gatgttgggt taagtcccgc    1080
aacgagcgca acccctattg ttagttgcca tcattaagtt gggcactcta gcgagactgc    1140
cggtaataaa ccgaggaag gtggggatga cgtcaaatca tcatgcccct tatgacctgg     1200
gctacacacg tgctacaatg gctggtacaa cgagtcgcaa gtcggtgacg acaagctaat    1260
ctcttaaagc cagtctcagt tcggattgta ggctgcaact cgcctacatg aagtcggaat    1320
cgctagtaat cgcggatcag cacgccgcgg tgaatacgtt cccgggcctt gtacacaccg    1380
cccgtcacac cacgagagtt gtaacaccc gaagtcggtg aggtaaccat ttggagccag     1440
ccgcctaagg tgggatagat gattggggtg aagtcgtaac a                       1481
```

<210> SEQ ID NO 17
<211> LENGTH: 1547
<212> TYPE: DNA
<213> ORGANISM: Streptococcus bovis

<400> SEQUENCE: 17

```
agagtttgat catggctcag gacgaacgct ggcggcgtgc ctaatacatg caagtggaac      60
gcatgattga taccggagct tgctccacca ttaatcatga gtcgcgaacg ggtgagtaac     120
gcgtaggtaa cctacctcat agcgggggat aactattgga aacgatagct aataccgcat    180
aacagtattt atcgcatggt aaatgcttga aaggagcaac tgcttcacta tgagatggac    240
ctgcgttgta ttagctagtt ggtggggtaa cggctcacca aggcatcgat acatagccga    300
cctgagaggg tgatcggcca cactgggact gagacacggc ccagactcct acgggaggca    360
gcagtaggga atcttcggca atgggggaa ccctgaccga gcaacgccgc gtgagtgaag    420
aaggttttcg gatcgtaaag ctctgttgta agagaagaac gtgtgtgaga gtggaaagtt    480
cacacagtga cggtaaccta ccagaaaggg acgctaact acgtgccagc agccgcggta    540
atacgtaggt cccgagcgtt gtccggattt attgggcgta aagcgagcgc aggcggtttg    600
ataagtctga agtaaaaggc tgtggcttaa ccatggtatg ctttggaaac tgtcaaactt    660
gagtgcagaa ggggagagtg gaattccatg tgtagcggtg aaatgcgtag atatatggag    720
gaacaccggt ggcgaaagcg actctctggt ctgtaactga cgctgaggct cgaaagcgtg    780
aggagcaaac aggattagat accctggtag tccacgccgt aaacgatgag tgctaggtgt    840
tgggtccttt ccgggactca gtgccgtagc taacgcatta agcactccgc ctggggagta    900
cgaccgcaag gttgaaactc aaaggaattg acggggccc gcacaagcgg tggagcatgt    960
ggtttaattc gaagcaacgc gaagaacctt accaggtctt gacatcccag tgaccgtcct   1020
agagatagga tttttcttcg gaacactgga gacaggtggt gcatggttgt cgtcagctcg   1080
tgtcgtgaga gttggttaa gtcccgcagc gagcgcaacc cctattgtta gttgccatca   1140
ttcagttggg cactctagcg agactgccgg taataaaccg gaggaaggtg gggatgacgt   1200
caaatcatca tgcccttat gacctgggct acacacgtgc tacaatggct ggtacaacga    1260
gtcgcaagtc ggtggcgaca agctaatctc ttaaagccag tctcagttcg gattgtaggc   1320
tgcaactcgc ctacatgaag tcggaatcgc tagtaatcgc ggatcagcac gccgcggtga   1380
```

```
atacgttccc gggccttgta cacaccgccc gtcacaccac gagagtttgt aacacccgaa    1440
gtcggtgagg taaccatttg agccagccg cctaaggtgg gatagatgat tggggtgaag     1500
tcgtaacaag gtagccgtat cggaaggtgc ggctggatca cctcctt                  1547
```

<210> SEQ ID NO 18
<211> LENGTH: 1541
<212> TYPE: DNA
<213> ORGANISM: Streptococcus bovis

<400> SEQUENCE: 18

```
agagtttgat cctggctcag gacgaacgct ggcggcgtgc ctaatacatg caagtagaac    60
gctgaagact ttagcttgct aaagttggaa gagttgcgaa cgggtgagta acgcgtaggt    120
aacctgccta ctagcggggg ataactattg gaaacgatag ctaataccgc ataacagcat    180
ttaacacatg ttagatgctt gaaaggagca attgcttcac tagtagatgg acctgcgttg    240
tattagctag ttggtgaggt aacggctcac caaggcgacg atacatagcc gacctgagag    300
ggtgatcggc cacactggga ctgagacacg gcccagactc ctacgggagg cagcagtagg    360
gaatcttcgg caatggggc aaccctgacc gagcaacgcc gcgtgagtga agaaggtttt    420
cggatcgtaa agctctgttg taagagaaga acgtgtgtga gagtggaaag ttcacacagt    480
gacggtaact taccagaaag ggacggctaa ctacgtgcca gcagccgcgg taatacgtag    540
gtcccgagcg ttgtccggat ttattgggcg taaagcgagc gcaggcggtt taataagtct    600
gaagttaaag gcagtggctt aaccattgtt cgctttggaa actgttagac ttgagtgcag    660
aaggggagag tggaattcca tgtgtagcgg tgaaatgcgt agatatatgg aggaacaccg    720
gtggcgaaag cggctctctg gtctgtaact gacgctgagg ctcgaaagcg tggggagcaa    780
acaggattag ataccctggt agtccacgcc gtaaacgatg agtgctaggt gttaggccct    840
ttccggggct tagtgccgca gctaacgcat taagcactcc gcctgggag tacgaccgca    900 aggttgaaac tcaaaggaat tgacggggc ccgcacaagc ggtggagcat gtggtttaat    960
tcgaagcaac gcgaagaacc ttaccaggtc ttgacatccc gatgctattc ctagagatag    1020
gaagtttctt cggaacatcg gtgacaggtg gtgcatggtt gtcgtcagct cgtgtcgtga    1080
gatgttgggt taagtcccgc aacgagcgca accctattg ttagttgcca tcattaagtt    1140
gggcactcta gcgagactgc cgtaataaa ccggaggaag gtgggatga cgtcaaatca    1200 tcatgcccct tatgacctgg gctacacacg tgctacaatg gttggtacaa cgagtcgcga    1260
gtcggtgacg gcaagcaaat ctcttaaagc caatctcagt tcggattgta ggctgcaact    1320
cgcctacatg aagtcggaat cgctagtaat cgcggatcag cacgccgcgg tgaatacgtt    1380
cccgggcctt gtacacaccg cccgtcacac cacgagagtt tgtaacaccc gaagtcggtg    1440 aggtaaccctt ttaggagcca gccgcctaag gtgggataga tgattggggt gaagtcgtaa    1500
caaggtagcc gtatcggaag gtgcggctgg atcacctcct t                         1541
```

<210> SEQ ID NO 19
<211> LENGTH: 1541
<212> TYPE: DNA
<213> ORGANISM: Streptococcus bovis

<400> SEQUENCE: 19

```
agagtttgat cctggctcag gacgaacgct ggcggcgtgc ctaatacatg caagtagaac    60
gctgactact ttagcttgct agagtagaag gagttgcgaa cgggtgagta acgcgtaggt    120
```

```
aacctgccta ctagcggggg ataactattg gaaacgatag ctaataccgc ataacagtgt    180
ttaacacatg ttagatgctt gaaagatgca aatgcatcac tagtagatgg acctgcgttg    240
tattagctag ttggtggggt aacggcctac caaggcgacg atacatagcc gacctgagag    300
ggtgatcggc cacactggga ctgagacacg gcccagactc ctacgggagg cagcagtagg    360
gaatcttcgg caatggggc  aaccctgacc gagcaacgcc gcgtgagtga agaaggtttt    420
cggatcgtaa agctctgttg taagagaaga acgtgtgtga gagtggaaag ttcacacagt    480
gacggtaact taccagaaag ggacggctaa ctacgtgcca gcagccgcgg taatacgtag    540
gtcccgagcg ttgtccggat ttattgggcg taaagcgagc gcaggcggtt taataagtct    600
gaagttaaag gcagtggctt aaccattgtt cgctttggaa actgttaaac ttgagtgcag    660
aaggggagag tggaattcca tgtgtagcgg tgaaatgcgt agatatatgg aggaacaccg    720
gtggcgaaag cggctctctg gtctgtaact gacgctgagg ctcgaaagcg tggggagcaa    780
acaggattag ataccctggt agtccacgcc gtaaacgatg agtgctaggt gttaggccct    840
ttccggggct tagtgccgca gctaacgcat taagcactcc gcctggggag tacgaccgca    900
aggttgaaac tcaaaggaat tgacgggggc ccgcacaagc ggtggagcat gtggtttaat    960
tcgaagcaac gcgaagaacc ttaccaggtc ttgacatccc gatgctattt ctagagatag   1020
aaagtttctt cggaacatcg tgacaggtg  gtgcatggtt gtcgtcagct cgtgtcgtga   1080
gatgttgggt taagtcccgc aacgagcgca accctattg  ttagttgcca tcattcagtt   1140
gggcactcta gcgagactgc cggtaataaa ccggaggaag gtggggatga cgtcaaatca   1200
tcatgcccct tatgacctgg gctacacacg tgctacaatg gttggtacaa cgagtcgcaa   1260
gtcggtgacg gcaagcaaat ctcttaaagc caatctcagt tcggattgta ggctgcaact   1320
cgcctacatg aagtcggaat cgctagtaat cgcggatcag cacgccgcgg tgaatacgtt   1380
cccgggcctt gtacacaccg cccgtcacac cacgagagtt tgtaacaccc gaagtcggtg   1440
aggtaacctt ttaggagcca gccgcctaag gtgggataga tgattggggt gaagtcgtaa   1500
caaggtagcc gtatcggaag gtgcggctgg atcacctcct t                       1541
```

<210> SEQ ID NO 20
<211> LENGTH: 1558
<212> TYPE: DNA
<213> ORGANISM: Streptococcus intermedius

<400> SEQUENCE: 20

```
tttgatcctg gttcaggacg aacgctggcg gcgtgcctaa tacatgcaag tagaacgcac     60
aggatgcacc gtagtttact acaccgtatt ctgtgagttg cgaacgggtg agtaacgcgt    120
aggtaacctg cctggtagcg ggggataact attggaaacg atagctaata ccgcataaga    180
acatttactg catggtagat gttaaaagg  tgcaaatgca tcactaccag atggacctgc    240
gttgtattag ctagtaggtg aggtaacggc tcacctaggc gacgatacat agccgacctg    300
agagggtgat cggccacact gggactgaga cacggcccag actcctacgg gaggcagcag    360
tagggaatct tcggcaatgg ggggaaccct gaccgagcaa cgccgcgtga gtgaagaagg    420
ttttcggatc gtaaagctct gttgttaagg aagaacgagt gtgagaatgg aaagttcata    480
ctgtgacggt acttaaccag aaagggacgg ctaactacgt gccagcagcc gcggtaatac    540
gtaggtcccg agcgttgtcc ggatttattg ggcgtaaagc gagcgcaggc ggttagataa    600
gtctgaagtt aaaggcagtg gctcaaccat tgtaggcttt ggaaactgtt aacttgagt     660
gcagaagggg agagtggaat tccatgtgta gcggtgaaat gcgtagatat atggaggaac    720
```

-continued

```
accggtggcg aaagcggctc tctggtctgt aactgacgct gaggctcgaa agcgtgggga    780
gcgaacagga ttagataccc tggtagtcca cgccgtaaac gatgagtgct aggtgttagg    840
tcctttccgg gacttagtgc cgcagctaac gcattaagca ctccgcctgg ggagtacgac    900
cgcaaggttg aaactcaaag gaattgacgg gggcccgcac aagcggtgga gcatgtggtt    960
taattcgaag caacgcgaag aaccttacca ggtcttgaca tcccgatgcc cgctctagag   1020
atagagcttt acttcggtac atcggtgaca ggtggtgcat ggttgtcgtc agctcgtgtc   1080
gtgagatgtt gggttaagtc cgcaacgag cgcaacccctt attgttagtt gccatcattc   1140
agttgggcac tctagcgaga ctgccggtaa taaaccggag gaaggtgggg atgacgtcaa   1200
atcatcatgc cccttatgac ctgggctaca cacgtgctac aatggctggt acaacgagtc   1260
gcaagccggt gacggcaagc taatctctga agccagtct cagttcggat tgtaggctgc   1320
aactcgccta catgaagtcg gaatcgctag taatcgcgga tcagcacgcc gcggtgaata   1380
cgttcccggg ccttgtacac accgcccgtc acaccacgag agtttgtaac acccgaagtc   1440
ggtgaggtaa ccgtaaggag ccagccgcct aaggtgggat agatgattgg ggtgaagtcg   1500
taacaaggta gccgtatcgg aaggtgcggc tggatcaccct ccttggtcat agctgttt    1558
```

<210> SEQ ID NO 21
<211> LENGTH: 1568
<212> TYPE: DNA
<213> ORGANISM: Streptococcus mitis

<400> SEQUENCE: 21

```
acaacagagt ttgatcctgg ctcaggacga acgctggcgg cgtgcctaat acatgcaagt     60
agaacgctga aggaggagct tgcttctctg gatgagttgc gaacgggtga gtaacgcgta    120
ggtaacctgc ctggtagcgg gggataaacta ttggaaacga tagctaatac cgcataagag    180
tagatgttgc atgacatttg cttaaaaggt gcaaatgcat cactaccaga tggacctgcg    240
ttgtattagc tagttggtgg ggtaacggct caccaaggcg acgatacata gccgacctga    300
gagggtgatc ggccacactg gactgagaca cggcccaga ctcctacggg aggcagcagt    360
agggaatctt cggcaatgga cggaagtctg accgagcaac gccgcgtgag tgaagaaggt    420
tttcggatcg taaagctctg ttgtaagaga agaacgagtg tgagagtgga aagttcacac    480
tgtgacggta tcttaccaga aagggacggc taactacgtg ccagcagccg cggtaatacg    540
taggtcccga gcgttgtccg gatttattgg gcgtaaagcg agcgcaggcg gttagataag    600
tctgaagtta aaggctgtgg cttaaccata gtacgctttg gaaactgttt aacttgagtg    660
caagagggga gagtggaatt ccatgtgtag cggtgaaatg cgtagatata tggaggaaca    720
ccggtggcga aagcggctct ctggcttgta actgacgctg aggctcgaaa gcgtggggag    780
caaacaggat tagataccct ggtagtccac gccgtaaacg atgagtgcta ggtgttagac    840
cctttccggg gtttagtgcc gcagctaacg cattaagcac tccgcctggg gagtacgacc    900
gcaaggttga aactcaaagg aattgacggg ggcccgcaca agcggtggag catgtggttt    960
aattcgaagc aacgcgaaga accttaccag gtcttgacat ccctctgacc gctctagaga   1020
tagagttttc cttcgggaca gaggtgacag gtggtgcatg gttgtcgtca gctcgtgtcg   1080
tgagatgttg ggttaagtcc cgcaacgagc gcaacccta ttgttagttg ccatcattca   1140
gttgggcact ctagcgagac tgccggtaat aaaccggagg aaggtgggga tgacgtcaaa   1200
tcatcatgcc ccttatgacc tgggctacac acgtgctaca atggctggta caacgagtcg   1260
```

```
caagccggtg acggcaagct aatctcttaa agccagtctc agttcggatt gtaggctgca    1320
actcgcctac atgaagtcgg aatcgctagt aatcgcggat cagcacgccg cggtgaatac    1380
gttcccgggc cttgtacaca ccgcccgtca caccacgaga gtttgtaaca cccgaagtcg    1440
gtgaggtaac cgtaaggagc cagccgccta aggtgggata gatgattggg gtgaagtcgt    1500
aacaaggtag ccgtatcgga aggtgcggct ggatcacctc cttaagcttg gatccccggt    1560
accgagct                                                              1568

<210> SEQ ID NO 22
<211> LENGTH: 1568
<212> TYPE: DNA
<213> ORGANISM: Streptococcus mitis

<400> SEQUENCE: 22
acaacagagt ttgatcctgg ctcaggacga acgctggcgg cgtgcctaat acatgcaagt      60
agaacgctga aggaggagct tgcttctctg gatgagttgc gaacgggtga gtaacgcgta     120
ggtaacctgc ctggtagcgg gggataacta ttggaaacga tagctaatac cgcataagag     180
tagatgttgc atgacatttg cttaaaaggt gcaaatgcat cactaccaga tggacctgcg     240
ttgtattagc tagttggtgg ggtaacggct caccaaggcg acgatacata gccgacctga     300
gagggtgatc ggccacactg ggactgagac acggcccaga ctcctacggg aggcagcagt     360
agggaatctt cggcaatgga cggaagtctg accgagcaac gccgcgtgag tgaagaaggt     420
tttcggatcg taaagctctg ttgtaagaga gaacgagtg tgagagtgga agttcacac       480 tgtgacggta tcttaccaga aagggacggc taactacgtg ccagcagccg cggtaatacg     540
taggtcccga gcgttgtccg gatttattgg gcgtaaagcg agcgcaggcg gttagataag     600
tctgaagtta aaggctgtgg cttaaccata gtacgctttg gaaactgttt aacttgagtg     660
caagagggga gagtggaatt ccatgtgtag cggtgaaatg cgtagatata tggaggaaca     720
ccggtggcga aagcggctct ctggcttgta actgacgctg aggctcgaaa gcgtggggag     780
caaacaggat tagataccct ggtagtccac gccgtaaacg atgagtgcta ggtgttagac     840
cctttccggg gtttagtgcc gcagctaacg cattaagcac tccgcctggg gagtacgacc     900
gcaaggttga aactcaaagg aattgacggg ggcccgcaca gcggtggag catgtggttt     960 aattcgaagc aacgcgaaga accttaccag gtcttgacat ccctctgacc gctctagaga    1020
tagagttttc cttcgggaca gaggtgacag gtggtgcatg gttgtcgtca gctcgtgtcg    1080
tgagatgttg ggttaagtcc cgcaacgagc gcaaccccta ttgttagttg ccatcattca    1140
gttgggcact ctagcgagac tgccggtaat aaaccggagg aaggtgggga tgacgtcaaa    1200
tcatcatgcc ccttatgacc tgggctacac acgtgctaca atggctggta caacgagtcg    1260
caagccggtg acggcaagct aatctcttaa agccagtctc agttcggatt gtaggctgca    1320
actcgcctac atgaagtcgg aatcgctagt aatcgcggat cagcacgccg cggtgaatac    1380
gttcccgggc cttgtacaca ccgcccgtca caccacgaga gtttgtaaca cccgaagtcg    1440
gtgaggtaac cgtaaggagc cagccgccta aggtgggata gatgattggg gtgaagtcgt    1500
aacaaggtag ccgtatcgga aggtgcggct ggatcacctc cttaagcttg gatccccggt    1560
accgagct                                                              1568

<210> SEQ ID NO 23
<211> LENGTH: 1454
<212> TYPE: DNA
<213> ORGANISM: Streptococcus mitis
```

<400> SEQUENCE: 23

```
cgctggcggc gtgcctaata catgcaagta gaacgctgaa ggaggagctt gcttctctgg      60
atgagttgcg aacgggtgag taacgcgtag gtaacctgcc tggtagcggg ggataactat     120
tggaaacgat agctaatacc gcataagagt agatgttgca tgacatttgc ttaaaaggtg     180
caattgcatc actaccagat ggacctgcgt tgtattagct agttggtggg gtaacggctc     240
accaaggcga cgatacatag ccgacctgag agggtgatcg ccacactgg gactgagaca     300
cggcccagac tcctacggga ggcagcagta gggaatcttc ggcaatggac ggaagtctga     360
ccgagcaacg ccgcgtgagt gaagaaggtt ttcggatcgt aaagctctgt tgtaagagaa     420
gaacgagtgt gagagtggaa agttcacact gtgacggtat cttaccagaa agggacggct     480
aactacgtgc cagcagccgc ggtaatacgt aggtcccgag cgttgtccgg atttattggg     540
cgtaaagcga gcgcaggcgg ttagataagt ctgaagttaa aggctgtggc ttaaccatag     600
tacgctttgg aaactgttta acttgagtgc aagaggggag agtggaattc catgtgtagc     660
ggtgaaatgc gtagatatat ggaggaacac cggtggcgaa agcggctctc tggcttgtaa     720
ctgacgctga ggctcgaaag cgtggggagc aaacaggatt agataccctg gtagtccacg     780
ccgtaaacga tgagtgctag gtgttagacc ctttccgggg tttagtgccg cagctaacgc     840
attaagcact ccgcctgggg agtacgaccg caaggttgaa actcaaagga attgacgggg     900
gcccgcacaa gcggtggagc atgtggttta attcgaagca acgcgaagaa ccttaccagg     960
tcttgacatc cctctgaccg ctctagagat agagttttcc ttcgggacag aggtgacagg    1020
tggtgcatgg ttgtcgtcag ctcgtgtcgt gagatgttgg gttaagtccc gcaacgagcg    1080
caaccctat tgttagttgc catcattag ttgggcactc tagcgagact gccggtaata    1140
aaccggagga aggtggggat gacgtcaaat catcatgccc cttatgacct gggctacaca    1200
cgtgctacaa tggctggtac aacgagtcgc aagccggtga cggcaagcta atctcttaaa    1260
gccagtctca gttcggattg taggctgcaa ctcgcctaca tgaagtcgga atcgctagta    1320
atcgcggatc agcacgccgc ggtgaatacg ttcccgggcc ttgtacacac cgcccgtcac    1380
accacgagag tttgtaacac ccgaagtcgg tgaggtaacc gtaaggagcc agccgcctaa    1440
ggtttgatag atga                                                     1454
```

<210> SEQ ID NO 24
<211> LENGTH: 1377
<212> TYPE: DNA
<213> ORGANISM: Streptococcus mitis

<400> SEQUENCE: 24

```
gagctgctac accatagact atgagttgcg aacgggtgag taacgcgtag gtaacctgcc      60
tggtagcggg ggataactat tggaaacgat agctaatacc gcataatatt aattattgca     120
tgataattaa ttgaaaggtg caattgcacc actaccagat ggacctgcgt tgtattagct     180
agtaggtgag gtaacggctc acctaggcga cgatacatag ccgacctgag agggtgatcg     240
gccacactgg gactgagaca cggcccagac tcctacggga ggcagcagta gggaatcttc     300
ggcaatggac gaaagtctga ccgagcaacg ccgcgtgagt gaagaaggtt ttcggatcgt     360
aaagctctgt tgtaagagaa gaacgggtgt gagagtggaa agttcacact gtgacggtat     420
cttaccagaa agggacggct aactacgtgc cagcagccgc ggtaatacgt aggtcccgag     480
cgttgtccgg atttattggg cgtaaagcga gcgcaggcgg ttagataagt ctgaagttaa     540
```

```
aggctgtggc ttaaccatag tacgctttgg aaactgttta acttgagtgc agaaggggag    600
agtggaattc catgtgtagc ggtgaaatgc gtagatatat ggaggaacac cggtggcgaa    660
agcggctctc tggtctgtaa ctgacgctga ggctcgaaag cgtggggagc gaacaggatt    720
agataccctg gtagtccacg ccgtaaacga tgagtgctag gtgttaggcc ctttccgggg    780
cttagtgccg cagctaacgc attaagcact ccgcctgggg agtacgaccg caaggttgaa    840
actcaaagga attgacgggg gcccgcacaa gcggtggagc atgtggttta attcgaagca    900
acgcgaagaa ccttaccagg tcttgacatc ccgatgcccg ctctagagat agagttttac    960
ttcggtacat cggtgacagg tggtgcatgg ttgtcgtcag ctcgtgtcgt gagatgttgg   1020
gttaagtccc gcaacgagcg caaccccctat tgttagttgc catcattcag ttgggcactc   1080
tagcgagact gccggtaata aaccggagga aggtggggat gacgtcaaat catcatgccc   1140
cttatgacct gggctacaca cgtgctacaa tggctggtac aacgagtcgc aagtcggtga   1200
cggcaagcta atctcttaaa gccagtctca gttcggattg taggctgcaa ctcgcctaca   1260
tgaagtcgga atcgctagta atcgcggatc agcacgccgc ggtgaatacg ttcccgggct   1320
ttgtacacac cgcccgtcac accacgagag tttgtaacac ccgaagttgg tgaggta     1377

<210> SEQ ID NO 25
<211> LENGTH: 1520
<212> TYPE: DNA
<213> ORGANISM: Streptococcus mitis

<400> SEQUENCE: 25
ttttgagttt gatcctggct caggacgaac gctggcggcg tgcctaatac atgcaagtag     60
aacgctgaag gaggagcttg cttctccgga tgagttgcga cgggtgagt aacgcgtagg    120 taacctgcct ggtagcgggg gataactatt ggaaacgata gctaataccg cataagagta    180
gatgttgcat gacatttgct aaaaggtgc aattgcatca ctaccagatg gacctgcgtt    240
gtattagcta gttggtgggg taacggctca ccaaggcgac gatacatagc cgacctgaga    300
gggtgatcgg ccacactggg actgagacac ggcccagact cctacgggag gcagcagtag    360
ggaatcttcg gcaatggacg gaagtctgac cgagcaacgc cgcgtgagtg aagaaggttt    420
tcggatcgta aagctctgtt gtaagagaag aacgagtgtg agagtggaaa gttcacactg    480
tgacggtatc ttaccagaaa gggacggcta actacgtgcc agcagccgcg gtaatacgta    540
ggtcccgagc gttgtccgga tttattgggc gtaaagcgag cgcaggcggt tagataagtc    600
tgaagttaaa ggctgtggct taaccatagt acgctttgga aactgtttaa cttgagtgca    660
agaggggaga gtggaattcc atgtgtagcg gtgaaatgcg tagatatatg gaggaacacc    720
ggtggcgaaa gcggctctct ggcttgtaac tgacgctgag gctcgaaagc gtggggagca    780
aacaggatta gataccctgg tagtccacgc cgtaaacgat gagtgctagg tgttagaccc    840
tttccggggt ttagtgccgc agctaacgca ttaagcactc cgcctgggga gtacgaccgc    900
aaggttgaaa ctcaaaggaa ttgacggggg cccgcacaag cggtggagca tgtggtttaa    960
ttcgaagcaa cgcgaagaac cttaccaggt cttgacatcc ctctgaccgc tctagagata   1020
gagttttcct tcgggacaga ggtgacaggt ggtgcatggt tgtcgtcagc tcgtgtcgtg   1080
agatgttggg ttaagtcccg caacgagcgc aaccccctatt gttagttgcc atcatttagt   1140
tgggcactct agcgagactg ccggtaataa accggaggaa ggtggggatg acgtcaaatc   1200
atcatgcccc ttatgacctg gctacacac gtgctacaat ggctggtaca acgagtcgca   1260
agccggtgac ggcaagctaa tctcttaaag ccagtctcag ttcggattgt aggctgcaac   1320
```

```
tcgcctacat gaagtcggaa tcgctagtaa tcgcggatca gcacgccgcg gtgaatacgt    1380
tcccgggcct tgtacacacc gcccgtcaca ccacgagagt ttgtaacacc cgaagtcggt    1440
gaggtaacct tttaggagcc agccgcctaa ggtgggatag atgattgggg tgaagtcgta    1500
acaagtcagc cgtttgggaa                                                1520
```

<210> SEQ ID NO 26
<211> LENGTH: 1406
<212> TYPE: DNA
<213> ORGANISM: Streptococcus mitis

<400> SEQUENCE: 26

```
gctcaggacg aacgctggcg gcgtgcctaa tacatgcaag tagaacgctg aaggaggagc      60
ttgcttctct ggatgagttg cgaacgggtg agtaacgcgt aggtaacctg cctggtagcg     120
ggggataact attggaaacg atagctaata ccgcataaga gtagatgttg catgacattt     180
gcttaaaagg tgcaattgca tcactaccag atggacctgc gttgtattag ctagttggtg     240
aggtaacggc tcaccaaggc aacgatacat agccgacctg agagggtgat cggccacact     300
gggactgaga cacggcccag actcctacgg gaggcagcag tagggaatct tcggcaatgg     360
acggaagtct gaccgagcaa cgccgcgtga gtgaagaagg ttttcggatc gtaaagctct     420
gttgtaagag aagaacgagt gtgagagtgg aaagttcaca ctgtgacggt atcttaccag     480
aaagggacgg ctaactacgt gccagcagcc gcggtaatac gtaggtcccg agcgttgtcc     540
ggatttattg ggcgtaaagc gagcgcaggc ggttagataa gtctgaagtt aaaggctgtg     600
gcttaaccat agtacgcttt ggaaactgtt aacttgagt gcaagagggg agagtggaat      660
tccatgtgta gcggtgaaat gcgtagatat atggaggaac accggtggcg aaagcggctc     720
tctggcttgt aactgacgct gaggctcgaa agcgtgggga gcaaacagga ttagataccc     780
tggtagtcca cgccgtaaac gatgagtgct aggtgttaga ccctttccgg ggtttagtgc     840
cgcagctaac gcattaagca ctccgcctgg ggagtacgac cgcaaggttg aaactcaaag     900
gaattgacgg gggcccgcac aagcggtgga gcatgtggtt taattcgaag caacgcgaag     960
aaccttacca ggtcttgaca tccctctgac cgctctagag atagagtttt ccttcgggac    1020
agaggtgaca ggtggtgcat ggttgtcgtc agctcgtgtc gtgagatgtt gggttaagtc    1080
ccgcaacgag cgcaacccct attgttagtt gccatcattc agttgggcac tctagcgaga    1140
ctgccggtaa taaccggag gaaggtgggg atgacgtcaa atcatcatgc cccttatgac      1200
ctgggctaca cacgtgctac aatggctggt acaacgagtc gcaagccggt gacggcaagc    1260
taatctctta aagccagtct cagttcggat tgtaggctgc aactcgccta catgaagtcg    1320
gaatcgctag taatcgcgga tcagcacgcc gcggtgaata cgttcccggg ccttgtacac    1380
accgcccgtc acaccacgag agtttg                                         1406
```

<210> SEQ ID NO 27
<211> LENGTH: 1430
<212> TYPE: DNA
<213> ORGANISM: Streptococcus mitis

<400> SEQUENCE: 27

```
aggacgaacg ctggcggcgt gcctaataca tgcaagtaga acgctgaaga gaggagcttg      60
ctcttcttgg atgagttgcg aacgggtgag taacgcgtag gtaacctgcc tggtagcggg     120
ggataactat tggaaacgat agctaatacc gcataaaatg gattatcgca tgataatcca     180
```

```
ttgaaaggtg caaatgcatc actaccagat ggacctgcgt tgtattagct agttggtggg      240
gtaacggctc accaaggcga cgatacatag ccgacctgag agggtgatcg gccacactgg      300
gactgagaca cggcccagac tcctacggga ggcagcagta gggaatcttc ggcaatggac      360
ggaagtctga ccgagcaacg ccgcgtgagt gaagaaggtt ttcggatcgt aaagctctgt      420
tgtaagagaa gaacgagtgt gagagtggaa agttcacact gtgacggtat cttaccagaa      480
agggacggct aactacgtgc cagcagccgc ggtaatacga aggtcccgag cgttgtccgg      540
atttattggg cgtaaagcga gcgcaggcgg ttagataagt ctgaagttaa aggctgtggc      600
ttaaccatag tacgctttgg aaactgttta acttgagtgc aagaggggag agtggaattc      660
catgtgtagc ggtgaaatgc gtagatatat ggaggaacac cggtggcgaa agcggctctc      720
tggcttgtaa ctgacgctga ggctcgaaag cgtggggagc aaacaggatt agataccctg      780
gtagtccacg ccgtaaacga tgagtgctag gtgttagacc ctttccgggg tttagtgccg      840
cagctaacgc attaagcact ccgcctgggg agtacgaccg caaggttgaa actcaaagga      900
attgacgggg gcccgcacaa gcggtggagc atgtggttta attcgaagca acgcgaagaa      960
ccttaccagg tcttgacatc cctctgatcg ctctagagat agagttttcc ttcgggacag     1020
aggtgacagg tggtgcatgg ttgtcgtcag ctcgtgtcgt gagatgttgg gttaagtccc     1080
gcaacgagcg caaccoctat tgttagttgc catcatttag ttgggcactc tagcgagact     1140
gccggtaata accggagga aggtggggat gacgtcaaat catcatgccc cttatgacct     1200
gggctacaca cgtgctacaa tggctggtac aacgagtcgc aagccggtga cggcaagcta     1260
atctcttaaa gccagtctca gttcggattg taggctgcaa ctcgcctaca tgaagtcgga     1320
atcgctagta atcgcggatc agcacgccgc ggtgaatacg ttcccgggcc ttgtacacac     1380
cgcccgtcac accacgagag tttgtaacac ccgaagtcgg tgaggtaacc               1430
```

```
<210> SEQ ID NO 28
<211> LENGTH: 1428
<212> TYPE: DNA
<213> ORGANISM: Streptococcus mitis

<400> SEQUENCE: 28
aggacgaacg ctggcggcgt gcctaataca tgcaagtaga acgctgaagg aggagcttgc       60
ttctctggat gagttgcgaa cgggtgagta acgcgtaggt aacctgcctg gtagcggggg      120
ataactattg gaaacgatag ctaataccgc ataaaattga ttattgcatg atagtcaatt      180
aaaaggtgca attgcatcac taccagatgg acctgcgttg tattagctag ttggtggggt      240
aacggctcac caaggcaacg atacatagcc gacctgagag ggtgatcggc cacactggga      300
ctgagacacg cccagactc ctacgggagg cagcaggagg gaatcttcgg caatggacgg      360
aagtctgacc gagcaacgcc gcgtgagtga agaaggtttt cggatcgtaa agctctgttg      420
taagagaaga cgagtgtga gagtggaaag ttcacactgt gacggtatct accagaaag      480 gacggctaa ctacgtgcca gcagccgcgg taatacgtag gtcccgagcg ttgtccggat      540
ttattgggcg taaagcgagc gcaggcggtt agataagtct gaagttaaag ctgtggctt      600 aaccatagta cgctttggaa actgtttaac ttgagtgcaa gagggagag tggaattcca      660 tgtgtagcg tgaaatgcgt agatatatg aggaacaccg gtggcgaaag cggctctctg      720
gcttgtaact gacgctgagg ctcgaaagcg tggggagcaa acaggattag ataccctgt      780 agtccacgcc gtaaacgatg agtgctaggt gttagaccct tccggggtt tagtgccgca      840 gctaacgcat taagcactcc gcctggggag tacgaccgca aggttgaaac tcaaaggaat      900
```

-continued

```
tgacggggc  ccgcacaagc  ggtggagcat  gtggtttaat  tcgaagcaac  gcgaagaacc    960
ttaccaggtc  ttgacatccc  tctgaccgct  ctagagatag  agttttcctt  cgggacagag   1020
gtgacaggtg  gtgcatggtt  gtcgtcagct  cgtgtcgtga  gatgttgggt  taagtcccgc   1080
aacgagcgca  accccctattg ttagttgcca  tcattcagtt  gggcactcta  gcgagactgc   1140
cggtaataaa  ccgaggaag   gtggggatga  cgtcaaatca  tcatgcccct  tatgacctgg   1200
gctacacacg  tgctacaatg  gctggtacaa  cgagtcgcaa  gccggtgacg  gcaagctaat   1260
ctcttaaagc  cagtctcagt  tcggattgta  ggctgcaact  cgcctacatg  aagtcggaat   1320
cgctagtaat  cgcggatcag  cacgccgcgg  tgaatacgtt  cccgggcctt  gtacacaccg   1380
cccgtcacac  cacgagagtt  tgtaacaccc  gaagtcggtg  aggtaacc                 1428
```

```
<210> SEQ ID NO 29
<211> LENGTH: 1430
<212> TYPE: DNA
<213> ORGANISM: Streptococcus mitis

<400> SEQUENCE: 29
```

```
aggatgaacg  ctggcggcgt  gcctaataca  tgcaagtaga  acgctgaagc  ttggtgcttg     60
caccgagcgg  atgagttgcg  aacgggtgag  taacgcgtag  gtaacctgcc  tcttagcggg    120
ggataactat  tggaaacgat  agctaatacc  gcataaaagt  cgatatcgca  tgatattgat    180
ttgaaaggtg  caaatgcatc  actaagagat  ggacctgcgt  tgtattagct  agttggtgag    240
gtaacggctc  accaaggcga  cgatacatag  ccgacctgag  agggtgatcg  ccacactgg     300 gactgagaca  cggcccagac  tcctacggga  ggcagcagta  gggaatcttc  ggcaatgggg    360
gcaaccctga  ccgagcaacg  ccgcgtgagt  gaagaaggtt  ttcggatcgt  aaagctctgt    420
tgtaagagaa  gaacgagtgt  gagagtggaa  agttcacact  gtgacggtaa  cttaccagaa    480
agggacggct  aactacgtgc  cagcagccgc  ggtaatacg   aggtcccgag  cgttatccgg    540
atttattggg  cgtaaagcga  gcgcaggcgg  ttagataagt  ctgaagttaa  aggctgtggc    600
ttaaccatag  tacgctttgg  aaactgttta  acttgagtgc  agaaggggag  agtggaattc    660
catgtgtagc  ggtgaaatgc  gtagatatat  ggaggaacac  cggtggcgaa  agcggctctc    720
tggtctgtaa  ctgacgctga  ggctcgaaag  cgtggggagc  aaacaggatt  agataccctg    780
gtagtccacg  ccgtaaacga  tgagtgctag  gtgttgggtc  ctttccggga  ctcagtgccg    840
cagctaacgc  attaagcact  ccgcctgggg  agtacgaccg  caaggttgaa  actcaaagga    900
attgacgggg  gcccgcacaa  gcggtggagc  atgtggttta  attcgaagca  acgcgaagaa    960
ccttaccagg  tcttgacatc  cctctgaccg  ctctagagat  agagttttcc  ttcgggacag   1020
aggtgacagg  tggtgcatgg  ttgtcgtcag  ctcgtgtcgt  gagatgttgg  gttaagtccc   1080
gcaacgagcg  caacccctat  tgttagttgc  catcattgag  ttgggcactc  tagcgagact   1140
gccggtaata  aaccggagga  aggtggggat  gacgtcaaat  catcatgccc  cttatgacct   1200
gggctacaca  cgtgctacaa  tggctggtac  aacgagtcgc  gagtcggtga  cggcaagcta   1260
atctcttaaa  gccagtctca  gttcggattg  taggctgcaa  ctcgcctaca  tgaagtcgga   1320
atcgctagta  atcgcggatc  agcacgtcgc  ggtgaatacg  ttcccgggcc  ttgtacacac   1380
cgcccgtcac  accacgagag  tttgtaacac  ccgaagtcgg  tgaggtaacc                1430
```

```
<210> SEQ ID NO 30
<211> LENGTH: 1540
<212> TYPE: DNA
```

<213> ORGANISM: Streptococcus mitis

<400> SEQUENCE: 30

| | | | | | |
|---|---|---|---|---|---|
| tggagagttt | gatcctggct | caggacgaac | gctggcggcg | tgcctaatac | atgcaagtag | 60 |
| aacgctgaag | gaggagcttg | cttctctgga | tgagttgcga | acgggtgagt | aacgcgtagg | 120 |
| taacctgcct | ggtagcgggg | gataactatt | ggaaacgata | gctaataccg | cataagagta | 180 |
| gatgttgcat | gacatttgct | taaaaggtgc | aattgcatca | ctaccagatg | gacctgcgtt | 240 |
| gtattagcta | gttggtgggg | taacggctca | ccaaggcgac | gatacatagc | cgacctgaga | 300 |
| gggtgatcgg | ccacactggg | actgagacac | ggcccagact | cctacgggag | gcagcagtag | 360 |
| ggaatcttcg | gcaatggacg | gaagtctgac | cgagcaacgc | cgcgtgagtg | aagaaggttt | 420 |
| tcggatcgta | aagctctgtt | gtaagagaag | aacgagtgtg | agagtggaaa | gttcacactg | 480 |
| tgacggtatc | ttaccagaaa | gggacggcta | actacgtgcc | agcagccgcg | gtaatacgta | 540 |
| ggtcccgagc | gttgtccgga | tttattgggc | gtaaagcgag | cgcaggcggt | tagataagtc | 600 |
| tgaagttaaa | ggctgtggct | taaccatagt | acgctttgga | aactgtttaa | cttgagtgca | 660 |
| agaggggaga | gtggaattcc | atgtgtagcg | gtgaaatgcg | tagatatatg | gaggaacacc | 720 |
| ggtggcgaaa | gcggctctct | ggcttgtaac | tgacgctgag | gctcgaaagc | gtggggagca | 780 |
| aacaggatta | gataccctgg | tagtccacgc | cgtaaacgat | gagtgctagg | tgttagaccc | 840 |
| tttccggggt | ttagtgccgc | agctaacgca | ttaagcactc | cgcctgggga | gtacgaccgc | 900 |
| aaggttgaaa | ctcaaaggaa | ttgacggggg | cccgcacaag | cggtggagca | tgtggtttaa | 960 |
| ttcgaagcaa | cgcgaagaac | cttaccaggt | cttgacatcc | ctctgaccgc | tctagagata | 1020 |
| gagctttcct | tcgggacaga | ggtgacaggt | ggtgcatggt | tgtcgtcagc | tcgtgtcgtg | 1080 |
| agatgttggg | ttaagtcccg | caacgagcgc | aaccccctatt | gttagttgcc | atcattcagt | 1140 |
| tgggcactct | agcgagactg | ccggtaataa | accggaggaa | ggtggggatg | acgtcaaatc | 1200 |
| atcatgcccc | ttatgacctg | ggctacacac | gtgctacaat | ggctggtaca | acgagtcgca | 1260 |
| agccggtgac | ggcaagctaa | tctcttaaag | ccagtctcag | ttcggattgt | aggctgcaac | 1320 |
| tcgcctacat | gaagtcggaa | tcgctagtaa | tcgcggatca | gcacgccgcg | gtgaatacgt | 1380 |
| tcccgggcct | tgtacacacc | gcccgtcaca | ccacgagagt | ttgtaacacc | cgaagtcggt | 1440 |
| gaggtaacct | tttaggagcc | agccgcctaa | ggtgggatag | atgattgggg | tgaagtcgta | 1500 |
| acaaggtagc | cgtatcggaa | ggtgcggctg | gatcacctcc | | | 1540 |

<210> SEQ ID NO 31
<211> LENGTH: 1460
<212> TYPE: DNA
<213> ORGANISM: Streptococcus oralis

<400> SEQUENCE: 31

| | | | | | |
|---|---|---|---|---|---|
| tttttgattt | gatcctggct | caggacgaac | gctggcggcg | tgcctaatac | atgcaagtag | 60 |
| aacgctgaag | cttggtgctt | gcaccgagcg | gatgagttgc | gaacgggtga | gtaacgcgta | 120 |
| ggtaacctgc | ctggtagcgg | gggataacta | ttggaaacga | tagctaatac | cgcataagag | 180 |
| tagatgttgc | atgacattta | cttaaaaggt | gcaattgcat | cactaccaga | tggacctgcg | 240 |
| ttgtattagc | tagttggtga | ggtaacggct | caccaaggca | acgatacata | gccgacctga | 300 |
| gagggtgatc | ggccacactg | ggactgagac | acggcccaga | ctcctacggg | aggcagcagt | 360 |
| agggaatctt | cggcaatgga | cggaagtctg | accgagcaac | gccgcgtgag | tgaagaaggt | 420 |
| tttcggatcg | taaagctctg | ttgtaagaga | agaacgagtg | tgagagtgga | aagttcacac | 480 |

```
tgtgacggta tcttaccaga aagggacggc taactacgtg ccagcagccg cggtaatacg      540
taggtcccga gcgttgtccg gatttattgg gcgtaaagcg agcgcaggcg gttagataag      600
tctgaagtta aaggctgtgg cttaaccata gtacgctttg gaaactgttt aacttgagtg      660
caagagggga gagtggaatt ccatgtgtag cggtgaaatg cgtagatata tggaggaaca      720
ccggtggcga aagcggctct ctggcttgta actgacgctg aggctcgaaa gcgtggggag      780
caaacaggat tagataccct ggtagtccac gccgtaaacg atgagtgcta ggtgttagac      840
cctttccggg gtttagtgcc gcagctaacg cattaagcac tccgcctggg gagtacgacc      900
gcaaggttga aactcaaagg aattgacggg ggcccgcaca agcggtggag catgtggttt      960
aattcgaagc aacgcgaaga accttaccag gtcttgacat ccctctgacc gctctagaga     1020
tagagttttc cttcgggaca gaggtgacag gtggtgcatg gttgtcgtca gctcgtgtcg     1080
tgagatgttg ggttaagtcc cgcaacgagc gcaaccccta ttgttagttg ccatcattca     1140
gttgggcact ctagcgagac tgccggtaat aaaccggagg aaggtgggga tgacgtcaaa     1200
tcatcatgcc ccttatgacc tgggctacac acgtgctaca atggctggta caacgagtcg     1260
caagccggtg acggcaagct aatctcttaa agccagtctc agttcggatt gtaggctgca     1320
actcgcctac atgaagtcgg aatcgctagt aatcgcggat cagcacgccg cggtgaatac     1380
gttcccgggc cttgtacaca ccgcccgtca caccacgaga gtttgtaaca cccgaagtcg     1440
gtgaggtaac ctttaggag                                                 1460

<210> SEQ ID NO 32
<211> LENGTH: 1428
<212> TYPE: DNA
<213> ORGANISM: Streptococcus oralis

<400> SEQUENCE: 32
aggacgaacg ctggcggcgt gcctaataca tgcaagtaga acgctgaagg aggagcttgc       60
tcttctggat gagttgcgaa cgggtgagta acgcgtaggt aacctgcctg gtagcgggg      120 ataactattg gaaacgatag ctaataccgc ataagagtag atgttgcatg acatttgctt      180
aaaaggtgca attgcatcac taccagatgg acctgcgttg tattagctag ttggtgaggt      240
aacggctcac caaggcaacg atacatagcc gacctgagag ggtgatcggc cacactggga      300
ctgagacacg gcccagactc ctacgggagg cagcagtagg gaatcttcgg caatggacgg      360
aagtctgacc gagcaacgcc gcgtgagtga agaaggtttt cggatcgtaa agctctgttg      420
taagagaaga acgagtgtga gagtggaaag ttcacactgt gacggtatct taccagaaag      480
ggacggctaa ctacgtgcca gcagccgcgg taatacgtag gtcccgagcg ttgtccggat      540
ttattgggcg taaagcgagc gcaggcggtt agataagtct gaagttaaag ctgtggctt      600 aaccatagta cgctttggaa actgtttaac ttgagtgcaa gaggggagag tggaattcca      660
tgtgtagcgg tgaaatgcgt agatatatgg aggaacaccg gtggcgaaag cggctctctg      720
gcttgtaact gacgctgagg ctcgaaagcg tggggagcaa acaggattag ataccctggt      780
agtccacgcc gtaaacgatg agtgctaggt gttagaccct tccggggtt tagtgccgca      840 gctaacgcat taagcactcc gcctggggag tacgaccgca aggttgaaac tcaaaggaat      900 tgacggggc ccgcacaagc ggtggagcat gtggtttaat tcgaagcaac gcgaagaacc      960
ttaccaggtc ttgacatccc tctgaccgct ctagagatag agttttcctt cgggacagag     1020
gtgacaggtg tgcatggtt gtcgtcagct cgtgtcgtga gatgttgggt taagtcccgc     1080
```

```
aacgagcgca accoctattg ttagttgcca tcattcagtt gggcactcta gcgagactgc   1140
cggtaataaa ccggaggaag gtggggatga cgtcaaatca tcatgcccct tatgacctgg   1200
gctacacacg tgctacaatg gctggtacaa cgagtcgcaa gccggtgacg gcaagctaat   1260
ctcttaaagc cagtctcagt tcggattgta ggctgcaact cgcctacatg aagtcggaat   1320
cgctagtaat cgcggatcag cacgccgcgg tgaatacgtt cccgggcctt gtacacaccg   1380
cccgtcacac cacgagagtt tgtaacaccc gaagtcggtg aggtaacc                1428
```

<210> SEQ ID NO 33
<211> LENGTH: 1428
<212> TYPE: DNA
<213> ORGANISM: Streptococcus oralis

<400> SEQUENCE: 33

```
aggacgaacg ctggcggcgt gcctaataca tgcaagtaga acgctgaagg aggagcttgc     60
ttctccggat gagttgcgaa cgggtgagta acgcgtaggt aacctgcctg gtagcggggg    120
ataactattg gaaacgatag ctaataccgc ataacagtag atattgcatg atatctgctt    180
gaaaggtgca attgcatcac taccagatgg acctgcgttg tattagctag ttggtgaggt    240
aacggctcac caaggcgacg atacatagcc gacctgagag ggtgatcggc cacactggga    300
ctgagacacg gcccagactc ctacgggagg cagcagtagg gaatcttcgg caatggacgg    360
aagtctgacc gagcaacgcc gcgtgagtga agaaggtttt cggatcgtaa agctctgttg    420
taagagaaga acgagtgtga gagtggaaag ttcacactgt gacggtatct taccagaaag    480
ggacggctaa ctacgtgcca gcagccgcgg taatacgtag gtcccgagcg ttgtccggat    540
ttattgggcg taaagcgagc gcaggcggtt agataagtct gaagttaaag gctgtggctt    600
aaccatagta cgctttggaa actgtttaac ttgagtgcaa gaggggagag tggaattcca    660
tgtgtagcgg tgaaatgcgt agatatatgg aggaacaccg gtggcgaaag cggctctctg    720
gcttgtaact gacgctgagg ctcgaaagcg tggggagcaa acaggattag ataccctggt    780
agtccacgcc gtaaacgatg agtgctaggt gttagaccct ttccgggggtt tagtgccgca    840 gctaacgcat taagcactcc gcctggggag tacgaccgca aggttgaaac tcaaaggaat    900 tgacggggc ccgcacaagc ggtggagcat gtggtttaat tcgaagcaac gcgaagaacc    960
ttaccaggtc ttgacatccc tctgaccact ctagagatag agttttcctt cgggacagag   1020
gtgacaggtg gtgcatggtt gtcgtcagct cgtgtcgtga gatgttgggt taagtcccgc   1080
aacgagcgca accoctattg ttagttgcca tcattcagtt gggcactcta gcgagactgc   1140
cggtaataaa ccggaggaag gtggggatga cgtcaaatca tcatgcccct tatgacctgg   1200
gctacacacg tgctacaatg gctggtacaa cgagtcgcaa gtcggtgacg gcaagctaat   1260
ctcttaaagc cagtctcagt tcggattgta ggctgcaact cgcctacatg aagtcggaat   1320
cgctagtaat cgcggatcag cacgccgcgg tgaatacgtt cccgggcctt gtacacaccg   1380
cccgtcacac cacgagagtt tgtaacaccc gaagtcggtg aggtaacc                1428
```

<210> SEQ ID NO 34
<211> LENGTH: 1471
<212> TYPE: DNA
<213> ORGANISM: Streptococcus oralis

<400> SEQUENCE: 34

```
gacgaacgct ggcggcgtgc ctaatacatg caagtagaac gctgaagctt ggtgcttgca     60
ccgagcggat gagttgcgaa cgggtgagta acgcgtaggt aacctgcctg gtagcggggg    120
```

-continued

| | |
|---|---|
| ataactattg gaaacgatag ctaataccgc ataagagtag atgttgcatg acatttactt | 180 |
| aaaaggtgca attgcatcac taccagatgg acctgcgttg tattagctag ttggtgaggt | 240 |
| aacggctcac caaggcaacg atacatagcc gacctgagag ggtgatcggc cacactggga | 300 |
| ctgagacacg gcccagactc ctacgggagg cagcagtagg gaatcttcgg caatggacgg | 360 |
| aagtctgacc gagcaacgcc gcgtgagtga agaaggtttt cggatcgtaa agctctgttg | 420 |
| taagagaaga acgagtgtga gagtggaaag ttcacactgt gacggtatct taccagaaag | 480 |
| ggacggctaa ctacgtgcca gcagccgcgg taatacgtag gtcccgagcg ttgtccggat | 540 |
| ttattgggcg taaagcgagc gcaggcggtt agataagtct gaagttaaag gctgtggctt | 600 |
| aaccatagta cgctttggaa actgtttaac ttgagtgcaa gaggggagag tggaattcca | 660 |
| tgtgtagcgg tgaaatgcgt agatatatgg aggaacaccg gtggcgaaag cggctctctg | 720 |
| gcttgtaact gacgctgagg ctcgaaagcg tggggagcaa acaggattag ataccctggt | 780 |
| agtccacgcc gtaaacgatg agtgctaggt gttagaccct tccggggtt tagtgccgca | 840 |
| gctaacgcat taagcactcc gcctggggag tacgaccgca aggttgaaac tcaaaggaat | 900 |
| tgacggggc ccgcacaagc ggtggagcat gtggtttaat tcgaagcaac gcgaagaacc | 960 |
| ttaccaggtc ttgacatccc tctgaccgct ctagagatag agttttcctt cgggacagag | 1020 |
| gtgacaggtg gtgcatggtt gtcgtcagct cgtgtcgtga gatgttgggt taagtcccgc | 1080 |
| aacgagcgca accccctattg ttagttgcca tcattcagtt gggcactcta gcgagactgc | 1140 |
| cggtaataaa ccggaggaag gtggggatga cgtcaaatca tcatgcccct tatgacctgg | 1200 |
| gctacacacg tgctacaatg gctggtacaa cgagtcgcaa gccggtgacg gcaagctaat | 1260 |
| ctcttaaagc cagtctcagt tcggattgta ggctgcaact cgcctacatg aagtcggaat | 1320 |
| cgctagtaat cgcggatcag cacgccgcgg tgaatacgtt cccgggcctt gtacacaccg | 1380 |
| cccgtcacac cacgagagtt tgtaacaccc gaagtcggtg aggtaacctt ttaggagcca | 1440 |
| gccgcctaag gtgggataga tgattggggt g | 1471 |

<210> SEQ ID NO 35
<211> LENGTH: 1486
<212> TYPE: DNA
<213> ORGANISM: Streptococcus pneumoniae

<400> SEQUENCE: 35

| | |
|---|---|
| ctggcggcgt gcctaataca tgcaagtaca acgctgaagg aggagcttgc ttctctggat | 60 |
| gagttgcgaa cgggtgagta acgcgtaggt aacctgcctg gtagcggggg ataactattg | 120 |
| gaaacgatag ctaataccgc ataagagtag atgttgcatg acatttactt aaaaggtgca | 180 |
| aatgcatcac taccagatgg acctgcgttg tattagctag ttggtgggt aacggctcac | 240 |
| caaggcgacg atacatagcc gacctgagag ggtgatcggc cacactggga ctgagacacg | 300 |
| gcccagactc ctacgggagg cagcagtagg gaatcttcgg caatggacgg aagtctgacc | 360 |
| gagcaacgcc gcgtgagtga agaaggtttt cggatcgtaa agctctgttg taagagaaga | 420 |
| acgagtgtga gagtggaaag ttcacactgt gacggtatct taccagaaag ggacggctaa | 480 |
| ctacgtgcca gcagccgcgg taatacgtag gtcccgagcg ttgtccggat ttattgggcg | 540 |
| taaagcgagc gcaggcggtt agataagtct gaagttaaag gctgtggctt aaccatagta | 600 |
| cgctttggaa actgtttaac ttgagtgcaa gaggggagag tggaattcca tgtgtagcgg | 660 |
| tgaaatgcgt agatatatgg aggaacaccg gtggcgaaag cggctctctg gcttgtaact | 720 |

```
gacgctgagg ctcgaaagcg tggggagcaa acaggattag atacccctggt agtccacgcc    780 gtaaacgatg agtgctaggt gttagaccct ttccggggtt tagtgccgca gctaacgcat    840
taagcactcc gcctggggag tacgaccgca aggttgaaac tcaaaggaat tgacgggggc    900
ccgcacaagc ggtggagcat gtggtttaat tcgaagcaac gcgaagaacc ttaccaggtc    960
ttgacatccc tctgaccact ctagagatag agttttcctt cgggacagag gtgacaggtg   1020
gtgcatggtt gtcgtcagct cgtgtcgtga gatgttgggt taagtcccgc aacgagcgca   1080 accccctattg ttagttgcca tcatttagtt gggcactcta gcgagactgc cggtaataaa  1140
ccggaggaag gtggggatga cgtcaaatca tcatgcccct tatgacctgg gctacacacg   1200
tgctacaatg gctggtacaa cgagtcgcaa gccggtgacg gcaagctaat ctcttaaagc   1260
cagtctcagt tcggattgta ggctgcaact cgcctacatg aagtcggaat cgctagtaat   1320
cgcggatcag cacgccgcgg tgaatacgtt cccgggcctt gtacacaccg cccgtcacac   1380
cacgagagtt tgtaacaccc gaagtcggtg aggtaaccgt aaggagccag ccgcctaagg   1440
tgggatagat gattggggtg aagtcgtaac aaggagccga tcgaag                  1486

<210> SEQ ID NO 36
<211> LENGTH: 1416
<212> TYPE: DNA
<213> ORGANISM: Streptococcus pneumoniae

<400> SEQUENCE: 36
cctaatacat gcaagtagaa cgctgaagga aggagcttgc ttctcttgga tgagttgcga     60
acgggtgagt aacgcgtagg taacctgcct ggtagcgggg gataactatt ggaaacgata    120
gctaataccg cataagagta gatgttgcat gacatttgct aaaaggtgc acttgcatca     180 ctaccagatg gacctgcgtt gtattagcta gttggtgggg taacggctca ccaaggcgac    240
gatacatagc cgacctgaga gggtgatcgg ccacactggg actgagacac ggcccagact    300
cctacgggag gcagcagtag ggaatcttcg gcaatggacg gaagtctgac cgagcaacgc    360
cgcgtgagtg aagaaggttt tcggatcgta aagctctgtt gtaagagaag aacgagtgtg    420
agagtggaaa gttcacactg tgacggtatc ttaccagaaa gggacggcta actacgtgcc    480
agcagccgcg gtaatacgta ggtcccgagc gttgtccgga tttattgggc gtaaagcgag    540
cgcaggcggt tagataagtc tgaagttaaa ggctgtggct taaccatagt aggctttgga    600
aactgtttaa cttgagtgca agaggggaga gtggaattcc atgtgtagcg gtgaaatgcg    660
tagatatatg gaggaacacc ggtggcgaaa gcggctctct ggcttgtaac tgacgctgag    720
gctcgaaagc gtggggagca acaggattag ataccctgg tagtccacgc tgtaaacgat    780
gagtgctagg tgttagaccc tttccggggt ttagtgccgt agctaacgca ttaagcactc    840
cgcctgggga gtacgaccgc aaggttgaaa ctcaaaggaa ttgacggggg cccgcacaag    900
cggtggagca tgtggtttaa ttcgaagcaa cgcgaagaac cttaccaggt cttgacatcc    960
ctctgacgac tctagagata gagttttcct tcgggacaga ggtgacaggt ggtgcatggt   1020
tgtcgtcagc tcgtgtcgtg agatgttggg ttaagtcccg caacgagcgc aaccccctatt  1080 gttagttgcc atcatttagt tgggcactct agcgagactg ccggtaataa accggaggaa   1140 ggtgggggatg acgtcaaatc atcatgcccc ttatgacctg gctacacac gtgctacaat   1200 ggctggtaca acgagtcgca agccggtgac ggcaagctaa tctcttaaag ccagtctcag   1260
ttcggattgt aggctgcaac tcgcctacat gaagtcggaa tcgctagtaa tcgcggatca   1320
gcacgccgcg gtgaatacgt tcccgggcct tgtacacacc gcccgtcaca ccacgagagt  1380
```

```
ttgtaacacc cgaagtcggt gaggtaacct tttagg                              1416

<210> SEQ ID NO 37
<211> LENGTH: 1514
<212> TYPE: DNA
<213> ORGANISM: Streptococcus pneumoniae

<400> SEQUENCE: 37
gtttgatcct ggctcaggac gaacgctggc ggcgtgccta atacatgcaa gtagaacgct    60
gaaggaggag cttgcttctc tggatgagtt gcgaacgggt gagtaacgcg taggtaacct   120
gcctggtagc gggggataac tattggaaac gatagctaat accgcataag agtggatgtt   180
gcatgacatt tgcttaaaag gtgcacttgc atcactacca gatggacctg cgttgtatta   240
gctagttggt ggggtaacgg ctcaccaagg cgacgataca tagccgacct gagagggtga   300
tcggccacac tgggactgag acacggccca gactcctacg ggaggcagca gtagggaatc   360
ttcggcaatg gacggaagtc tgaccgagca acgccgcgtg agtgaagaag gttttcggat   420
cgtaaagctc tgttgtaaga agaacgagt tgtgagagtg gaaagttcac actgtgacgg   480
tatcttacca gaaagggacg ctaactacg tgccagcagc cgcggtaata cgtaggtccc   540
gagcgttgtc cggatttatt gggcgtaaag cgagcgcagg cggttagata gtctgaagt   600 taaaggctgt ggcttaacca tagtaggctt tggaaactgt ttaacttgag tgcaagaggg   660
gagagtggaa ttccatgtgt agcggtgaaa tgcgtagata tatggaggaa caccggtggc   720
gaaagcggct ctctggcttg taactgacgc tgaggctcga aagcgtgggg agcaaacagg   780
attagatacc ctggtagtcc acgctgtaaa cgatgagtgc taggtgttag accctttccg   840
gggtttagtg ccgtagctaa cgcattaagc actccgcctg gggagtacga ccgcaaggtt   900
gaaactcaaa ggaattgacg ggggcccgca caagcggtgg agcatgtggt ttaattcgaa   960
gcaacgcgaa gaaccttacc aggtcttgac atccctctga ccgctctaga gatagagttt  1020
tccttcggga cagaggtgac aggtggtgca tggttgtcgt cagctcgtgt cgtgagatgt  1080
tgggttaagt cccgcaacga gcgcaacccc tattgttagt tgccatcatt cagttgggca  1140
ctctagcgag actgccggta taaaccggag gaaggtggg gatgacgtca aatcatcatg  1200 cccttatga cctgggctac acacgtgcta caatggctgg tacaacgagt cgcaagccgg  1260
tgacggcaag ctaatctctt aaagccagtc tcagttcgga ttgtaggctg caactcgcct  1320
acatgaagtc ggaatcgcta gtaatcgcgg atcagcacgc cgcggtgaat acgttcccgg  1380
gccttgtaca caccgcccgt cacaccacga gagtttgtaa caccccgaagt cggtgaggta  1440 accgtaagga ccagccgcc taaggtggga tagatgattg gggtgaagtc gtaacaaggt   1500
agccgtatcg gaag                                                    1514

<210> SEQ ID NO 38
<211> LENGTH: 1514
<212> TYPE: DNA
<213> ORGANISM: Streptococcus pneumoniae

<400> SEQUENCE: 38
gtttgatcct ggctcaggac gaacgctggc ggcgtgccta atacatgcaa gtagaacgct    60
gaaggaggag cttgcttctc tggatgagtt gcgaacgggt gagtaacgcg taggtaacct   120
gcctggtagc gggggataac tattggaaac gatagctaat accgcataag agtggatgtt   180
gcatgacatt tgcttaaaag gtgcacttgc atcactacca gatggacctg cgttgtatta   240
```

```
gctagttggt ggggtaacgg ctcaccaagg cgacgataca tagccgacct gagagggtga    300
tcggccacac tgggactgag acacggccca gactcctacg ggaggcagca gtagggaatc    360
ttcggcaatg gacggaagtc tgaccgagca acgccgcgtg agtgaagaag gttttcggat    420
cgtaaagctc tgttgtaaga gaagaacgag tgtgagagtg aaagttcac actgtgacgg     480 tatcttacca gaaagggacg gctaactacg tgccagcagc cgcggtaata cgtaggtccc    540
gagcgttgtc cggatttatt gggcgtaaag cgagcgcagg cggttagata agtctgaagt    600
taaaggctgt ggcttaacca tagtaggctt tggaaactgt ttaacttgag tgcaagaggg    660
gagagtggaa ttccatgtgt agcggtgaaa tgcgtagata tatggaggaa caccggtggc    720
gaaagcggct ctctggcttg taactgacgc tgaggctcga aagcgtgggg agcaaacagg    780
attagatacc ctggtagtcc acgctgtaaa cgatgagtgc taggtgttag accctttccg    840
gggtttagtg ccgtagctaa cgcattaagc actccgcctg gggagtacga ccgcaaggtt    900
gaaactcaaa ggaattgacg ggggcccgca caagcggtgg agcatgtggt ttaattcgaa    960
gcaacgcgaa gaaccttacc aggtcttgac atccctctga ccgctctaga gatagagttt   1020
tccttcggga cagaggtgac aggtggtgca tggttgtcgt cagctcgtgt cgtgagatgt   1080
tgggttaagt cccgcaacga gcgcaacccc tattgttagt tgccatcatt cagttgggca   1140
ctctagcgag actgccggta ataaaccgga ggaaggtggg gatgacgtca aatcatcatg   1200 cccttatga cctgggctac acacgtgcta caatggctgg tacaacgagt cgcaagccgg   1260
tgacggcaag ctaatctctt aaagccagtc tcagttcgga ttgtaggctg caactcgcct   1320
acatgaagtc ggaatcgcta gtaatcgcgg atcagcacgc cgcggtgaat acgttcccgg   1380
gccttgtaca caccgcccgt cacaccacga gagtttgtaa cacccgaagt cggtgaggta   1440
accgtaagga gccagccgcc taaggtggga tagatgattg gggtgaagtc gtaacaaggt   1500
agccgtatcg gaag                                                     1514

<210> SEQ ID NO 39
<211> LENGTH: 1514
<212> TYPE: DNA
<213> ORGANISM: Streptococcus pneumoniae

<400> SEQUENCE: 39
gtttgatcct ggctcaggac gaacgctggc ggcgtgccta atacatgcaa gtagaacgct    60
gaaggaggag cttgcttctc tggatgagtt gcgaacgggt gagtaacgcg taggtaacct   120
gcctggtagc gggggataac tattggaaac gatagctaat accgcataag agtggatgtt   180
gcatgacatt tgcttaaaag gtgcacttgc atcactacca gatggacctg cgttgtatta   240
gctagttggt ggggtaacgg ctcaccaagg cgacgataca tagccgacct gagagggtga   300
tcggccacac tgggactgag acacggccca gactcctacg ggaggcagca gtagggaatc   360
ttcggcaatg gacggaagtc tgaccgagca acgccgcgtg agtgaagaag gttttcggat   420
cgtaaagctc tgttgtaaga gaagaacgag tgtgagagtg aaagttcac actgtgacgg    480 tatcttacca gaaagggacg gctaactacg tgccagcagc cgcggtaata cgtaggtccc   540
gagcgttgtc cggatttatt gggcgtaaag cgagcgcagg cggttagata agtctgaagt   600
taaaggctgt ggcttaacca tagtaggctt tggaaactgt ttaacttgag tgcaagaggg   660
gagagtggaa ttccatgtgt agcggtgaaa tgcgtagata tatggaggaa caccggtggc   720
gaaagcggct ctctggcttg taactgacgc tgaggctcga aagcgtgggg agcaaacagg   780
attagatacc ctggtagtcc acgctgtaaa cgatgagtgc taggtgttag accctttccg   840
```

-continued

```
gggtttagtg ccgtagctaa cgcattaagc actccgcctg gggagtacga ccgcaaggtt      900
gaaactcaaa ggaattgacg ggggcccgca caagcggtgg agcatgtggt ttaattcgaa      960
gcaacgcgaa gaaccttacc aggtcttgac atccctctga ccgctctaga gatagagttt     1020
tccttcggga cagaggtgac aggtggtgca tggttgtcgt cagctcgtgt cgtgagatgt     1080
tgggttaagt cccgcaacga gcgcaacccc tattgttagt tgccatcatt cagttgggca     1140
ctctagcgag actgccggta ataaaccgga ggaaggtggg gatgacgtca aatcatcatg     1200
ccccttatga cctgggctac acacgtgcta caatggctgg tacaacgagt cgcaagccgg     1260
tgacggcaag ctaatctctt aaagccagtc tcagttcgga ttgtaggctg caactcgcct     1320
acatgaagtc ggaatcgcta gtaatcgcgg atcagcacgc cgcggtgaat acgttcccgg     1380
gccttgtaca caccgcccgt cacaccacga gagtttgtaa cacccgaagt cggtgaggta     1440
accgtaagga ccagccgcc taaggtggga tagatgattg gggtgaagtc gtaacaaggt      1500
agccgtatcg gaag                                                       1514
```

<210> SEQ ID NO 40
<211> LENGTH: 1514
<212> TYPE: DNA
<213> ORGANISM: Streptococcus pneumoniae

<400> SEQUENCE: 40

```
gtttgatcct ggctcaggac gaacgctggc ggcgtgccta atacatgcaa gtagaacgct       60
gaaggaggag cttgcttctc tggatgagtt gcgaacgggt gagtaacgcg taggtaacct      120
gcctggtagc gggggataac tattggaaac gatagctaat accgcataag agtggatgtt      180
gcatgacatt tgcttaaaag gtgcacttgc atcactacca gatggacctg cgttgtatta      240
gctagttggt ggggtaacgg ctcaccaagg cgacgataca tagccgacct gagagggtga     300
tcggccacac tgggactgag acacggccca gactcctacg ggaggcagca gtagggaatc     360
ttcggcaatg gacggaagtc tgaccgagca acgccgcgtg agtgaagaag gttttcggat     420
cgtaaagctc tgttgtaaga agaacgagt tgtgagagtg gaaagttcac actgtgacgg      480
tatcttacca gaaagggacg gctaactacg tgccagcagc cgcggtaata cgtaggtccc     540
gagcgttgtc cggatttatt gggcgtaaag cgagcgcagg cggttagata agtctgaagt     600
taaaggctgt ggcttaacca tagtaggctt tggaaactgt ttaacttgag tgcaagaggg     660
gagagtggaa ttccatgtgt agcggtgaaa tgcgtagata tatggaggaa caccggtggc     720
gaaagcggct ctctggcttg taactgacgc tgaggctcga aagcgtgggg agcaaacagg     780
attagatacc ctggtagtcc acgctgtaaa cgatgagtgc taggtgttag acccttccg     840 gggtttagtg ccgtagctaa cgcattaagc actccgcctg gggagtacga ccgcaaggtt     900
gaaactcaaa ggaattgacg ggggcccgca caagcggtgg agcatgtggt ttaattcgaa     960
gcaacgcgaa gaaccttacc aggtcttgac atccctctga ccgctctaga gatagagttt    1020
tccttcggga cagaggtgac aggtggtgca tggttgtcgt cagctcgtgt cgtgagatgt    1080
tgggttaagt cccgcaacga gcgcaacccc tattgttagt tgccatcatt cagttgggca    1140
ctctagcgag actgccggta ataaaccgga ggaaggtggg gatgacgtca aatcatcatg    1200
ccccttatga cctgggctac acacgtgcta caatggctgg tacaacgagt cgcaagccgg    1260
tgacggcaag ctaatctctt aaagccagtc tcagttcgga ttgtaggctg caactcgcct    1320
acatgaagtc ggaatcgcta gtaatcgcgg atcagcacgc cgcggtgaat acgttcccgg    1380
```

```
gccttgtaca caccgcccgt cacaccacga gagtttgtaa cacccgaagt cggtgaggta    1440
accgtaagga gccagccgcc taaggtggga tagatgattg gggtgaagtc gtaacaaggt    1500
agccgtatcg gaag                                                     1514
```

<210> SEQ ID NO 41
<211> LENGTH: 1428
<212> TYPE: DNA
<213> ORGANISM: Streptococcus pneumoniae

<400> SEQUENCE: 41

```
aggacgaacg ctggcggcgt gcctaataca tgcaagtaga acgctgaagg aggagcttgc     60
ttctctggat gagttgcgaa cgggtgagta acgcgtaggt aacctgcctg gtagcggggg    120
ataactattg gaaacgatag ctaataccgc ataagagtag atgttgcatg acatttgctt    180
aaaaggtgca cttgcatcac taccagatgg acctgcgttg tattagctag ttggtggggt    240
aagggctcac caaggcgacg atacatagcc gacctgagag ggtgatcggc cacactggga    300
ctgagacacg gcccagactc ctacgggagg cagcagtagg gaatcttcgg caatggacgg    360
aagtctgacc gagcaacgcc gcgtgagtga agaaggtttt cggatcgtaa agctctgttg    420
taagagaaga acgagtgtga gagtggaaag ttcacactgt gacggtatct taccagaaag    480
ggacggctaa ctacgtgcca gcagccgcgg taatacgtag gtcccgagcg ttgtccggat    540
ttattgggcg taaagcgagc gcaggcggtt agataagtct gaagttaaag gctgtggctt    600
aaccatagta ggctttggaa actgtttaac ttgagtgcaa gaggggagag tggaattcca    660
tgtgtagcgg tgaaatgcgt agatatatgg aggaacaccg gtggcgaaag cggctctctg    720
gcttgtaact gacgctgagg ctcgaaagcg tggggagcaa acaggattag ataccctggt    780
agtccacgct gtaaacgatg agtgctaggt gttagaccct tccggggtt tagtgccgta    840 gctaacgcat taagcactcc gcctggggag tacgaccgca aggttgaaac tcaaaggaat    900
tgacgggggc ccgcacaagc ggtggagcat gtggtttaat tcgaagcaac gcgaagaacc    960
ttaccaggtc ttgacatccc tctgaccgct ctagagatag agttttcctt cgggacagag   1020
gtgacaggtg gtgcatggtt gtcgtcagct cgtgtcgtga gatgttgggt taagtcccgc   1080
aacgagcgca acccctattg ttagttgcca tcatttagtt gggcactcta gcgagactgc   1140
cggtaataaa ccggaggaag gtggggatga cgtcaaatca tcatgcccct tatgacctgg   1200
gctacacacg tgctacaatg gctggtacaa cgagtcgcaa gccggtgacg gcaagctaat   1260
ctcttaaagc cagtctcagt tcggattgta ggctgcaact cgcctacatg aagtcggaat   1320
cgctagtaat cgcggatcag cacgccgcgg tgaatacgtt cccgggcctt gtacacaccg   1380
cccgtcacac cacgagagtt tgtaacaccc gaagtcggtg aggtaacc                1428
```

<210> SEQ ID NO 42
<211> LENGTH: 1428
<212> TYPE: DNA
<213> ORGANISM: Streptococcus pneumoniae

<400> SEQUENCE: 42

```
aggacgaacg ctggcggcgt gcctaataca tgcaagtaga acgctgaagg aggagcttgc     60
ttctctggat gagttgcgaa cgggtgagta acgcgtaggt aacctgcctg gtagcggggg    120
ataactattg gaaacgatag ctaataccgc ataagagtag atgttgcatg acatttgctt    180
aaaaggtgca cttgcatcac taccagatgg acctgcgttg tattagctag ttggtggggt    240
aacggctcac caaggcgacg atacatagcc gacctgagag ggtgatcggc cacactggga    300
```

-continued

```
ctgagacacg gcccagactc ctacgggagg cagcagtagg gaatcttcgg caatggacgg      360
aagtctgacc gagcaacgcc gcgtgagtga agaaggtttt cggatcgtaa agctctgttg      420
taagagaaga acgagtgtga gagtggaaag ttcacactgt gacggtatct taccagaaag      480
ggacggctaa ctacgtgcca gcagccgcgg taatacgtag gtcccgagcg ttgtccggat      540
ttattgggcg taaagcgagc gcaggcggtt agataagtct gaagttaaag gctgtggctt      600
aaccatagta ggctttggaa actgtttaac ttgagtgcaa gaggggagag tggaattcca      660
tgtgtagcgg tgaaatgcgt agatatatgg aggaacaccg gtggcgaaag cggctctctg      720
gcttgtaact gacgctgagg ctcgaaagcg tggggagcaa acaggattag ataccctggt      780
agtccacgct gtaaacgatg agtgctaggt gttagaccct tccgggggtt tagtgccgta      840
gctaacgcat taagcactcc gcctggggag tacgaccgca aggttgaaac tcaaaggaat      900
tgacgggggc ccgcacaagc ggtggagcat gtggtttaat tcgaagcaac gcgaagaacc      960
ttaccaggtc ttgacatccc tctgaccgct ctagagatag agttttcctt cgggacagag     1020
gtgacaggtg gtgcatggtt gtcgtcagct cgtgtcgtga gatgttgggt taagtcccgc     1080
aacgagcgca acccctattg ttagttgcca tcatttagtt gggcactcta gcgagactgc     1140
cggtaataaa ccggaggaag gtggggatga cgtcaaatca tcatgcccct tatgacctgg     1200
gctacacacg tgctacaatg gctggtacaa cgagtcgcaa gccggtgacg gcaagctaat     1260
ctcttaaagc cagtctcagt tcggattgta ggctgcaact cgcctacatg aagtcggaat     1320
cgctagtaat cgcggatcag cacgccgcgg tgaatacgtt cccgggcctt gtacacaccg     1380
cccgtcacac cacgagagtt tgtaacaccc gaagtcggtg aggtaacc                  1428
```

<210> SEQ ID NO 43
<211> LENGTH: 1427
<212> TYPE: DNA
<213> ORGANISM: Streptococcus pneumoniae

<400> SEQUENCE: 43

```
aggacgaacg ctggcggcgt gcctaataca tgcaagtaga acgctgaagg aggagctgct       60
tctctggatg agttgcgaac gggtgagtaa cgcgtaggta acctgcctgg tagcggggga      120
taactattgg aaacgatagc taataccgca taagagtgga tgttcatga catttgctta      180 aaaggtgcac ttgcatcact accagatgga cctgcgttgt attagctagt tggtggggta      240
acggctcacc aaggcgacga tacatagccg acctgagagg gtgatcggcc acactgggac      300
tgagacacgg cccagactcc tacgggaggc agcagtaggg aatcttcggc aatggacgga      360
agtctgaccg agcaacgccg cgtgagtgaa gaaggttttc ggatcgtaaa gctctgttgt      420
aagagaagaa cgagtgtgag agtggaaagt tcacactgtg acggtatctt accagaaagg      480
gacggctaac tacgtgccag cagccgcggt aatacgtagg tcccgagcgt tgtccggatt      540
tattgggcgt aaagcgagcg caggcggtta gataagtctg aagttaaagg ctgtggctta      600
accatagtag gctttggaaa ctgtttaact tgagtgcaag aggggagagt ggaattccat      660
gtgtagcggt gaaatgcgta gatatatgga ggaacaccgg tggcgaaagc ggctctctgg      720
cttgtaactg acgctgaggc tcgaaagcgt ggggagcaaa caggattaga taccctggta      780
gtccacgctg taaacgatga gtgctaggtg ttagaccctt ccgggggttt agtgccgtag      840
ctaacgcatt aagcactccg cctggggagt acgaccgcaa ggttgaaact caaaggaatt      900
gacgggggcc gcacaagcg gtggagcatg tggtttaatt cgaagcaacg cgaagaacct      960
```

```
taccaggtct tgacatccct ctgaccgctc tagagataga gttttccttc gggacagagg    1020
tgacaggtgg tgcatggttg tcgtcagctc gtgtcgtgag atgttgggtt aagtcccgca    1080
acgagcgcaa ccctattgt tagttgccat catttagttg ggcactctag cgagactgcc    1140
ggtaataaac cggaggaagg tggggatgac gtcaaatcat catgccccctt atgacctggg   1200 ctacacacgt gctacaatgg ctggtacaac gagtcgcaag ccggtgacgg caagctaatc    1260
tcttaaagcc agtctcagtt cggattgtag gctgcaactc gcctacatga agtcggaatc    1320
gctagtaatc gcggatcagc acgccgcggt gaatacgttc ccgggccttg tacacaccgc    1380
ccgtcacacc acgagagttt gtaacacccg aagtcggtga ggtaacc                  1427
```

<210> SEQ ID NO 44
<211> LENGTH: 1468
<212> TYPE: DNA
<213> ORGANISM: Streptococcus pneumoniae

<400> SEQUENCE: 44

```
gacgaacgct ggcggcgtgc ctaatacatg caagtagaac gctgaaggag gagcttgctt    60
ctctggatga gttgcgaacg ggtgagtaac gcgtaggtaa cctgcctggt agcgggggat    120
aactattgga aacgatagct aataccgcat aagagtggat gttgcatgac atttgcttaa    180
aaggtgcact tgcatcacta ccagatggac ctgcgttgta ttagctagtt ggtgggtaa    240 cggctcacca aggcgacgat acatagccga cctgagaggg tgatcggcca cactgggact    300
gagacacggc ccagactcct acgggaggca gcagtaggga tcttcggca atggacggaa    360 gtctgaccga gcaacgccgc gtgagtgaag aaggttttcg gatcgtaaag ctctgttgta    420
agagaagaac gagtgtgaga gtggaaagtt cacactgtga cggtatctta ccagaaaggg    480
acggctaact acgtgccagc agccgcggta atacgtaggt cccgagcgtt gtccggattt    540
attgggcgta aagcgagcgc aggcggttag ataagtctga agttaaaggc tgtggcttaa    600
ccatagtagg ctttggaaac tgtttaactt gagtgcaaga ggggagagtg gaattccatg    660
tgtagcggtg aaatgcgtag atatatggag gaacaccggt ggcgaaagcg gctctctggc    720
ttgtaactga cgctgaggct cgaaagcgtg gggagcaaac aggattagat accctggtag    780
tccacgctgt aaacgatgag tgctaggtgt tagacccttt ccggggttta gtgccgtagc    840
taacgcatta agcactccgc ctggggagta cgaccgcaag gttgaaactc aaaggaattg    900 acggggggccc gcacaagcgg tggagcatgt ggtttaattc gaagcaacgc gaagaacctt    960
accaggtctt gacatccctc tgaccgctct agagatagag ttttccttcg ggacagaggt    1020
gacaggtggt gcatggttgt cgtcagctcg tgtcgtgaga tgttgggtta agtcccgcaa    1080
cgagcgcaac ccctattgtt agttgccatc attcagttgg gcactctagc gagactgccg    1140
gtaataaacc ggaggaaggt ggggatgacg tcaaatcatc atgccccctta tgacctgggc    1200 tacacacgtg ctacaatggc tggtacaacg agtcgcaagc cggtgacggc aagctaatct    1260
cttaaagcca gtctcagttc ggattgtagg ctgcaactcg cctacatgaa gtcggaatcg    1320
ctagtaatcg cggatcagca cgccgcggtg aatacgttcc cgggccttgt acacaccgcc    1380
cgtcacacca cgagagtttg taacacccga agtcggtgag gtaaccgtaa ggagccagcc    1440
gcctaaggtg ggatagatga ttggggtg                                       1468
```

<210> SEQ ID NO 45
<211> LENGTH: 1501
<212> TYPE: DNA
<213> ORGANISM: Streptococcus pyogenes

<400> SEQUENCE: 45

```
gacgaacgct ggcggcgtgc ctaatacatg caagtagaac gctgagaact ggtgcttgca      60
ccggttcaag gagttgcgaa cgggtgagta acgcgtaggt aacctacctc atagcggggg     120
ataactattg gaaacgatag ctaataccgc ataagagaga ctaacgcatg ttagtaattt     180
aaaaggggca attgctccac tatgagatgg acctgcgttg tattagctag ttggtgaggt     240
aaaggctcac caaggcgacg atacatagcc gacctgagag ggtgatcggc cacactggga     300
ctgagacacg gcccagactc ctacgggagg cagcagtagg gaatcttcgg caatgggggc     360
aaccctgacc gagcaacgcc gcgtgagtga agaaggtttt cggatcgtaa agctctgttg     420
ttagagaaga atgatggtgg gagtggaaaa tccaccaagt gacggtaact aaccagaaag     480
ggacggctaa ctacgtgcca gcagccgcgg taatacgtag gtcccgagcg ttgtccggat     540
ttattgggcg taaagcgagc gcaggcggtt ttttaagtct gaagttaaag gcattggctc     600
aaccaatgta cgctttggaa actggagaac ttgagtgcag aaggggagag tggaattcca     660
tgtgtagcgg tgaaatgcgt agatatatgg aggaacaccg gtggcgaaag cggctctctg     720
gtctgtaact gacgctgagg ctcgaaagcg tggggagcaa acaggattag ataccctggt     780
agtccacgcc gtaaacgatg agtgctaggt gttaggccct ttccggggct tagtgccgga     840
gctaacgcat taagcactcc gcctggggag tacgaccgca aggttgaaac tcaaaggaat     900
tgacggggc ccgcacaagc ggtggagcat gtggtttaat tcgaagcaac gcgaagaacc     960
ttaccaggtc ttgacatccc gatgcccgct ctagagatag agttttactt cggtacatcg    1020
gtgacaggtg gtgcatggtt gtcgtcagct cgtgtcgtga gatgttgggt taagtcccgc    1080
aacgagcgca accccctattg ttagttgcca tcattaagtt gggcactcta gcgagactgc    1140
cggtaataaa ccggaggaag gtggggatga cgtcaaatca tcatgcccct tatgacctgg    1200
gctacacacg tgctacaatg gttggtacaa cgagtcgcaa gccggtgacg gcaagctaat    1260
ctcttaaagc caatctcagt tcggattgta ggctgcaact cgcctacatg aagtcggaat    1320
cgctagtaat cgcggatcag cacgccgcgg tgaatacgtt cccgggcctt gtacacaccg    1380
cccgtcacac cacgagagtt tgtaacaccc gaagtcggtg aggtaaccta ttaggagcca    1440
gccgcctaag gtgggataga tgattggggt gaagtcgtaa caaggtagcc gtatcggaag    1500
g                                                                    1501
```

<210> SEQ ID NO 46
<211> LENGTH: 1335
<212> TYPE: DNA
<213> ORGANISM: Streptococcus pyogenes

<400> SEQUENCE: 46

```
gaacgggtga gtaacgcgta ggtaacctac ctcatagcgg gggataacta ttggaaacga      60
tagctaatac cgcataagag agactaacgc atgttagtaa tttaaaaggg gcaattgctc     120
cactatgaga tggaccctgcg ttgtattagc tagttggtga ggtaaaggct caccaaggcg     180
acgatacata gccgacctga gagggtgatc ggccacactg gactgagaca cggcccaga     240
ctcctacggg aggcagcagt agggaatctt cggcaatggg ggcaaccctg accgagcaac     300
gccgcgtgag tgaagaaggt tttcggatcg taaagctctg ttgttagaga agaatgatgg     360
tgggagtgga aaatccacca agtgacggta actaaccaga aagggacggc taactacgtg     420
ccagcagccg cggtaatacg taggtcccga gcgttgtccg gatttattgg gcgtaaagcg     480
```

-continued

```
agcgcaggcg gttttttaag tctgaagtta aaggcattgg ctcaaccaat gtacgctttg    540
gaaactggag aacttgagtg cagaagggga gagtggaatt ccatgtgtag cggtgaaatg    600
cgtagatata tggaggaaca ccggtggcga aagcggctct ctggtctgta actgacgctg    660
aggctcgaaa gcgtggggag caaacaggat tagataccct ggtagtccac gccgtaaacg    720
atgagtgcta ggtgttaggc cctttccggg gcttagtgcc ggagctaacg cattaagcac    780
tccgcctggg gagtacgacc gcaaggttga aactcaaagg aattgacggg ggcccgcaca    840
agcggtggag catgtggttt aattcgaagc aacgcgaaga accttaccag gtcttgacat    900
cccgatgccc gctctagaga tagagtttta cttcggtaca tcggtgacag gtggtgcatg    960
gttgtcgtca gctcgtgtcg tgagatgttg ggttaagtcc cgcaacgagc gcaaccccta   1020
ttgttagttg ccatcattaa gttgggcact ctagcgagac tgccggtaat aaaccggagg   1080
aaggtgggga tgacgtcaaa tcatcatgcc ccttatgacc tgggctacac acgtgctaca   1140
atggttggta caacgagtcg caagccggtg acggcaagct aatctcttaa agccaatctc   1200
agttcggatt gtaggctgca actcgcctac atgaagtcgg aatcgctagt aatcgcggat   1260
cagcacgccg cggtgaatac gttcccgggc cttgtacaca ccgcccgtca caccacgaga   1320
gtttgtaaca cccga                                                    1335
```

<210> SEQ ID NO 47
<211> LENGTH: 1335
<212> TYPE: DNA
<213> ORGANISM: Streptococcus pyogenes

<400> SEQUENCE: 47

```
gaacgggtga gtaacgcgta ggtaacctac ctcatagcgg gggataacta ttggaaacga    60
tagctaatac cgcataagag agactaacgc atgttagtaa tttaaaaggg gcaattgctc   120
cactatgaga tggacctgcg ttgtattagc tagttggtga ggtaaaggct caccaaggcg   180
acgatacata gccgacctga gagggtgatc ggccacactg ggactgagac acggcccaga   240
ctcctacggg aggcagcagt agggaatctt cggcaatggg ggcaaccctg accgagcaac   300
gccgcgtgag tgaagaaggt tttcggatcg taaagctctg ttgttagaga agaatgatgg   360
tgggagtgga aaatccacca agtgacggta actaaccaga aagggacggc taactacgtg   420
ccagcagccg cggtaatacg taggtcccga gcgttgtccg gatttattgg gcgtaaagcg   480
agcgcaggcg gttttttaag tctgaagtta aaggcattgg ctcaaccaat gtacgctttg    540
gaaactggag aacttgagtg cagaagggga gagtggaatt ccatgtgtag cggtgaaatg    600
cgtagatata tggaggaaca ccggtggcga aagcggctct ctggtctgta actgacgctg    660
aggctcgaaa gcgtggggag caaacaggat tagataccct ggtagtccac gccgtaaacg    720
atgagtgcta ggtgttaggc cctttccggg gcttagtgcc ggagctaacg cattaagcac    780
tccgcctggg gagtacgacc gcaaggttga aactcaaagg aattgacggg ggcccgcaca    840
agcggtggag catgtggttt aattcgaagc aacgcgaaga accttaccag gtcttgacat    900
cccgatgccc gctctagaga tagagtttta cttcggtaca tcggtgacag gtggtgcatg    960
gttgtcgtca gctcgtgtcg tgagatgttg ggttaagtcc cgcaacgagc gcaaccccta   1020
ttgttagttg ccatcattaa gttgggcact ctagcgagac tgccggtaat aaaccggagg   1080
aaggtgggga tgacgtcaaa tcatcatgcc ccttatgacc tgggctacac acgtgctaca   1140
atggttggta caacgagtcg caagccggtg acggcaagct aatctcttaa agccaatctc   1200
agttcggatt gtaggctgca actcgcctac atgaagtcgg aatcgctagt aatcgcggat   1260
```

-continued

| | |
|---|---|
| cagcacgccg cggtgaatac gttcccgggc cttgtacaca ccgcccgtca caccacgaga | 1320 |
| gtttgtaaca cccga | 1335 |

<210> SEQ ID NO 48
<211> LENGTH: 1335
<212> TYPE: DNA
<213> ORGANISM: Streptococcus pyogenes

<400> SEQUENCE: 48

| | |
|---|---|
| gaacgggtga gtaacgcgta ggtaacctac ctcatagcgg gggataacta ttggaaacga | 60 |
| tagctaatac cgcataagag agactaacgc atgttagtaa tttaaaaggg gcaattgctc | 120 |
| cactatgaga tggacctgcg ttgtattagc tagttggtga ggtaaaggct caccaaggcg | 180 |
| acgatacata gccgacctga gagggtgatc ggccacactg ggactgagac acggcccaga | 240 |
| ctcctacggg aggcagcagt agggaatctt cggcaatggg ggcaaccctg accgagcaac | 300 |
| gccgcgtgag tgaagaaggt tttcggatcg taaagctctg ttgttagaga agaatgatgg | 360 |
| tgggagtgga aaatccacca agtgacggta actaaccaga aagggacggc taactacgtg | 420 |
| ccagcagccg cggtaatacg taggtcccga gcgttgtccg gatttattgg gcgtaaagcg | 480 |
| agcgcaggcg gttttttaag tctgaagtta aaggcattgg ctcaaccaat gtacgctttg | 540 |
| gaaactggag aacttgagtg cagaagggga gagtggaatt ccatgtgtag cggtgaaatg | 600 |
| cgtagatata tggaggaaca ccggtggcga aagcggctct ctggtctgta actgacgctg | 660 |
| aggctcgaaa gcgtggggag caaacaggat tagataccct ggtagtccac gccgtaaacg | 720 |
| atgagtgcta ggtgttaggc cctttccggg gcttagtgcc ggagctaacg cattaagcac | 780 |
| tccgcctggg gagtacgacc gcaaggttga aactcaaagg aattgacggg ggcccgcaca | 840 |
| agcggtggag catgtggttt aattcgaagc aacgcgaaga accttaccag gtcttgacat | 900 |
| cccgatgccc gctctagaga tagagtttta cttcggtaca tcggtgacag gtggtgcatg | 960 |
| gttgtcgtca gctcgtgtcg tgagatgttg ggttaagtcc cgcaacgagc gcaacccta | 1020 |
| ttggtagttg ccatcattaa gttgggcact ctagcgagac tgccggtaat aaaccggagg | 1080 |
| aaggtgggga tgacgtcaaa tcatcatgcc ccttatgacc tgggctacac acgtgctaca | 1140 |
| atggttggta caacgagtcg caagccggtg acggcaagct aatctcttaa agccaatctc | 1200 |
| agttcggatt gtaggctgca actcgcctac atgaagtcgg aatcgctagt aatcgcggat | 1260 |
| cagcacgccg cggtgaatac gttcccgggc cttgtacaca ccgcccgtca caccacgaga | 1320 |
| gtttgtaaca cccga | 1335 |

<210> SEQ ID NO 49
<211> LENGTH: 1336
<212> TYPE: DNA
<213> ORGANISM: Streptococcus pyogenes

<400> SEQUENCE: 49

| | |
|---|---|
| gaacgggtga gtaacgcgta ggtaacctac ctcatagcgg gggataacta ttggaaacga | 60 |
| tagctaatac cgcataagag agactaacgc atgttagtaa tttaaaaggg gcaattgctc | 120 |
| cactatgaga tggacctgcg ttgtattagc tagttggtga ggtaaaggct caccaaggcg | 180 |
| acgatacata gccgacctga gagggtgatc ggccacactg ggactgagac acggcccaga | 240 |
| ctcctacggg aggcagcagt agggaatctt cggcaatggg ggcaaccctg accgagcaac | 300 |
| gccgcgtgag tgaagaaggt tttcggatc gtaaagctct gttgttagag aagaatgatg | 360 |

```
gtgggagtgg aaaatccacc aagtgacggt aactaaccag aaagggacgg ctaactacgt      420
gccagcagcc gcggtaatac gtaggtcccg agcgttgtcc ggatttattg ggcgtaaagc      480
gagcgcaggc ggtttttaa gtctgaagtt aaaggcattg gctcaaccaa tgtacgcttt      540
ggaaactgga gaacttgagt gcagaagggg agagtggaat tccatgtgta gcggtgaaat      600
gcgtagatat atggaggaac accggtggcg aaagcggctc tctggtctgt aactgacgct      660
gaggctcgaa agcgtgggga gcaaacagga ttagatacccc tggtagtcca cgccgtaaac      720
gatgagtgct aggtgttagg ccctttccgg gcttagtgc cggagctaac gcattaagca      780
ctccgcctgg ggagtacgac cgcaaggttg aaactcaaag gaattgacgg gggcccgcac      840
aagcggtgga gcatgtggtt taattcgaag caacgcgaag aaccttacca ggtcttgaca      900
tcccgatgcc cgctctagag atagagtttt acttcggtac atcggtgaca ggtggtgcat      960
ggttgtcgtc agctcgtgtc gtgagatgtt gggttaagtc ccgcaacgag cgcaaccccct    1020 attgttagtt gccatcatta gttgggcac tctagcgaga ctgccggtaa taaaccggag      1080
gaaggtgggg atgacgtcaa atcatcatgc cccttatgac ctgggctaca cacgtgctac     1140
aatggttggt acaacgagtc gcaagccggt gacggcaagc taatctctta aagccaatct     1200
cagttcggat tgtaggctgc aactcgccta catgaagtcg gaatcgctag taatcgcgga     1260
tcagcacgcc gcggtgaata cgttcccggg ccttgtacac accgcccgtc acaccacgag    1320
agtttgtaac acccga                                                     1336

<210> SEQ ID NO 50
<211> LENGTH: 1335
<212> TYPE: DNA
<213> ORGANISM: Streptococcus pyogenes

<400> SEQUENCE: 50
gaacgggtga gtaacgcgta ggtaacctac ctcatagcgg gggataacta ttggaaacga      60
tagctaatac cgcataagag agactaacgc atgttagtaa tttaaaaggg gcaattgctc     120
cactatgaga tggacctgcg ttgtattagc tagttggtga ggtaaaggct caccaaggcg     180
acgatacata gccgacctga gagggtgatc ggccacactg ggactgagac acggcccaga    240
ctcctacggg aggcagcagt agggaatctt cggcaatggg ggcaaccctg accgagcaac    300
gccgcgtgag tgaagaaggt tttcggatcg taaagctctg ttgttagaga agaatgatgg    360
tgggagtgga aaatccacca agtgacggta actaaccaga aagggacggc taactacgtg    420
ccagcagccg cggtaatacg taggtcccga gcgttgtccg gatttattgg gcgtaaagcg    480
agcgcaggcg gtttttaag tctgaagtta aaggcattgg ctcaaccaat gtacgctttg     540
gaaactggag aacttgagtg cagaagggga gagtggaatt ccatgtgtag cggtgaaatg    600
cgtagatata tggaggaaca ccggtggcga aagcggctct ctggtctgta actgacgctg    660
aggctcgaaa gcgtggggag caaacaggat tagataccct ggtagtccac gccgtaaacg    720
atgagtgcta ggtgttaggc cctttccggg cttagtgcc ggagctaacg cattaagcac     780
tccgcctggg gagtacgacc gcaaggttga aactcaaagg aattgacggg gcccgcaca    840 agcggtggag catgtggttt aattcgaagc aacgcgaaga accttaccag gtcttgacat    900
cccgatgccc gctctagaga tagagttta cttcggtaca tcggtgacag gtggtgcatg     960
gttgtcgtca gctcgtgtcg tgagatgttg ggttaagtcc cgcaacgagc gcaacccccta   1020 ttgttagttg ccatcattaa gttgggcact ctagcgagac tgccggtaat aaaccggagg    1080
aaggtgggga tgacgtcaaa tcatcatgcc ccttatgacc tgggctacac acgtgctaca    1140
```

```
atggttggta caacgagtcg caagccggtg acggcaagct aatctcttaa agccaatctc    1200
agttcggatt gtaggctgca actcgcctac atgaagtcgg aatcgctagt aatcgcggat    1260
cagcacgccg cggtgaatac gttcccgggc cttgtacaca ccgcccgtca caccacgaga    1320
gtttgtaaca cccga                                                    1335
```

<210> SEQ ID NO 51
<211> LENGTH: 1335
<212> TYPE: DNA
<213> ORGANISM: Streptococcus pyogenes

<400> SEQUENCE: 51

```
gaacgggtga gtaacgcgta ggtaacctac tcatagcgg gggataacta ttggaaacga      60
tagctaatac cgcataagag agactaacgc atgttagtaa tttaaaaggg gcaattgctc    120
cactatgaga tggacctgcg ttgtattagc tagttggtga ggtaaaggct caccaaggcg    180
acgatacata gccgacctga gagggtgatc ggccacactg ggactgagac acggcccaga    240
ctcctacggg aggcagcagt agggaatctt cggcaatggg ggcaaccctg accgagcaac    300
gccgcgtgag tgaagaaggt tttcggatcg taaagctctg ttgttagaga agaatgatgg    360
tgggagtgga aaatccacca gtgacggta actaaccaga aagggacggc taactacgtg    420
ccagcagccg cggtaatacg taggtcccga gcgttgtccg gatttattgg gcgtaaagcg    480
agcgcaggcg gtttttttaag tctgaagtta aaggcattgg ctcaaccaat gtacgctttg    540
gaaactggag aacttgagtg cagaagggga gagtggaatt ccatgtgtag cggtgaaatg    600
cgtagatata tggaggaaca ccggtggcga aagcggctct ctggtctgta actgacgctg    660
aggctcgaaa gcgtggggag caaacaggat tagatacccct ggtagtccac gccgtaaacg    720
atgagtgcta ggtgttaggc cctttccggg gcttagtgcc ggagctaacg cattaagcac    780
tccgcctggg gagtacgacc gcaaggttga aactcaaagg aattgacggg ggcccgcaca    840
agcggtggag catgtggttt aattcgaagc aacgcgaaga accttaccag gtcttgacat    900
cccgatgccc gctctagaga tagagtttta cttcggtaca tcggtgacag gtggtgcatg    960
gttgtcgtca gctcgtgtcg tgagatgttg ggttaagtcc cgcaacgagc gcaacccta    1020 ttgttagttg ccatcattaa gttgggcact ctagcgagac tgccggtaat aaaccggagg    1080
aaggtgggga tgacgtcaaa tcatcatgcc ccttatgacc tgggctacac acgtgctaca    1140
atggttggta caacgagtcg caagccggtg acggcaagct aatctcttaa agccaatctc    1200
agttcggatt gtaggctgca actcgcctac atgaagtcgg aatcgctagt aatcgcggat    1260
cagcacgccg cggtgaatac gttcccgggc cttgtacaca ccgcccgtca caccacgaga    1320
gtttgtaaca cccga                                                    1335
```

<210> SEQ ID NO 52
<211> LENGTH: 1393
<212> TYPE: DNA
<213> ORGANISM: Streptococcus pyogenes

<400> SEQUENCE: 52

```
agagtttgat cctggctcag gacgaacgct ggcggcgtgc ctaatacatg caagtagacg      60
aacgggtgag taacgcgtag gtaacctacc tcatagcggg ggataactat ggaaacgat    120 agctaatacc gcataagaga gactaacgca tgttagtaat ttaaaagggg caattgctcc    180
actatgagat ggacctgcgt tgtattagct agttggtgag gtaaaggctc accaaggcga    240
```

-continued

```
cgatacatag ccgacctgag agggtgatcg gccacactgg gactgagaca cggcccagac    300
tcctacggga ggcagcagta gggaatcttc ggcaatgggg caaccctga ccgagcaacg    360 ccgcgtgagt gaagaaggtt ttcggatcgt aaagctctgt tgttagagaa gaatgatggt    420
gggagtggaa aatccaccaa gtgacggtaa ctaaccagaa agggacggct aactacgtgc    480
cagcagccgc ggtaatacgt aggtcccgag cgttgtccgg atttattggg cgtaaagcga    540
gcgcaggcgg ttttttaagt ctgaagttaa aggcattggc tcaaccaatg tacgctttgg    600
aaactggaga acttgagtgc agaaggggag agtggaattc catgtgtagc ggtgaaatgc    660
gtagatatat ggaggaacac cggtggcgaa agcggctctc tggtctgtaa ctgacgctga    720
ggctcgaaag cgtggggagc aaacaggatt agatacctg gtagtccacg ccgtaaacga    780
tgagtgctag gtgttaggcc ctttccgggg cttagtgccg gagctaacgc attaagcact    840
ccgcctgggg agtacgaccg caaggttgaa actcaaagga attgacgggg cccgcacaa    900 gcggtggagc atgtggttta attcgaagca acgcgaagaa ccttaccagg tcttgacatc    960
ccgatgcccg ctctagagat agagttttac ttcggtacat cggtgacagg tggtgcatgg    1020
ttgtcgtcag ctcgtgtcgt gagatgttgg gttaagtccc gcaacgagcg caaccccta    1080 tgttagttgc catcattaag ttgggcactc tagcgagact gccggtaata accggagga    1140 aggtggggat gacgtcaaat catcatgccc cttatgacct gggctacaca cgtgctacaa    1200
tggttggtac aacgagtcgc aagccggtga cggcaagcta atctcttaaa gccaatctca    1260
gttcggattg taggctgcaa ctcgcctaca tgaagtcgga atcgctagta atcgcggatc    1320
agcacgccgc ggtgaatacg ttcccgggcc ttgtacacac cgcccgtcac accacgagag    1380
tttgtaacac ccg                                                      1393
```

<210> SEQ ID NO 53
<211> LENGTH: 1335
<212> TYPE: DNA
<213> ORGANISM: Streptococcus pyogenes

<400> SEQUENCE: 53

```
gaacgggtga gtaacgcgta ggtaacctac ctcatagcgg gggataacta ttggaaacga     60
tagctaatac cgcataagag agactaacgc atgttagtaa tttaaaaggg gcaattgctc    120
cactatgaga tggacctgcg ttgtattagc tagttggtga ggtaaaggct caccaaggcg    180
acgatacata gccgacctga gagggtgatc ggccacactg ggactgagac acggcccaga    240
ctcctacggg aggcagcagt agggaatctt cggcaatggg ggcaaccctg accgagcaac    300
gccgcgtgag tgaagaaggt tttcggatcg taaagctctg ttgttagaga agaatgatgg    360
tgggagtgga aaatccacca agtgacggta actaaccaga aagggacggc taactacgtg    420
ccagcagccg cggtaatacg taggtcccga gcgttgtccg gatttattgg gcgtaaagcg    480
agcgcaggcg gttttttaag tctgaagtta aaggcattgg ctcaaccaat gtacgctttg    540
gaaactggag aacttgagtg cagaagggga gagtggaatt ccatgtgtag cggtgaaatg    600
cgtagatata tggaggaaca ccagtggcga aagcggctct ctggtctgta actgacgctg    660
aggctcgaaa gcgtggggag caaacaggat tagataccct ggtagtccac gccgtaaacg    720
atgagtgcta ggtgttaggc cctttccggg gcttagtgcc ggagctaacg cattaagcac    780
tccgcctggg gagtacgacc gcaaggttga aactcaaagg aattgacggg gcccgcaca    840 agcggtggag catgtggttt aattcgaagc aacgcgaaga accttaccag gtcttgacat    900
cccgatgccc gctctagaga tagagttttta cttcggtaca tcggtgacag gtggtgcatg    960
```

-continued

```
gttgtcgtca gctcgtgtcg tgagatgttg ggttaagtcc cgcaacgagc gcaacccta      1020 ttgttagttg ccatcattaa gttgggcact ctagcgagac tgccggtaat aaaccggagg    1080
aaggtgggga tgacgtcaaa tcatcatgcc cctatgacc tgggctacac acgtgctaca     1140
atggttggta caacgagtcg caagccggtg acggcaagct aatctcttaa agccaatctc    1200
agttcggatt gtaggctgca actcgcctac atgaagtcgg aatcgctagt aatcgcggat    1260
cagcacgccg cggtgaatac gttcccgggc cttgtacaca ccgcccgtca caccacgaga    1320
gtttgtaaca cccga                                                     1335
```

<210> SEQ ID NO 54
<211> LENGTH: 1335
<212> TYPE: DNA
<213> ORGANISM: Streptococcus pyogenes

<400> SEQUENCE: 54

```
gaacgggtga gtaacgcgta ggtaacctac ctcatagcgg gggataacta ttggaaacga    60
tagctaatac cgcataagag agactaacgc atgttagtaa tttaaaaggg gcaattgctc    120
cactatgaga tggacctgcg ttgtattagc tagttggtga ggtaaaggct caccaaggcg    180
acgatacata gccgacctga gagggtgatc ggccacactg gactgagaca cggcccaga    240 ctcctacggg aggcagcagt agggaatctt cggcaatggg ggcaaccctg accgagcaac    300
gccgcgtgag tgaagaaggt tttcggatcg taaagctctg ttgttagaga agaatgatgg    360
tgggagtgga aaatccacca agtgacggta actaaccaga aagggacggc taactacgtg    420
ccagcagccg cggtaatacg taggtcccga gcgttgtccg gatttattgg gcgtaaagcg    480
agcgcaggcg gtttttaag tctgaagtta aaggcattgg ctcaaccaat gtacgctttg    540
gaaactggag aacttgagtg cagaagggga gagtggaatt ccatgtgtag cggtgaaatg    600
cgtagatata tggaggaaca ccagtggcga aagcggctct ctggtctgta actgacgctg    660
aggctcgaaa gcgtggggag caaacaggat tagataccct ggtagtccac gccgtaaacg    720
atgagtgcta ggtgttaggc cctttccggg gcttagtgcc ggagctaacg cattaagcac    780
tccgcctggg gagtacgacc gcaaggttga aactcaaagg aattgacggg ggcccgcaca    840
agcggtggag catgtggttt aattcgaagc aacgcgaaga accttaccag gtcttgacat    900
cccgatgccc gctctagaga tagagttttta cttcggtaca tcggtgacag gtggtgcatg    960
gttgtcgtca gctcgtgtcg tgagatgttg ggttaagtcc cgcaacgagc gcaacccta    1020 ttgttagttg ccatcattaa gttgggcact ctagcgagac tgccggtaat aaaccggagg    1080
aaggtgggga tgacgtcaaa tcatcatgcc cctatgacc tgggctacac acgtgctaca    1140
atggttggta caacgagtcg caagccggtg acggcaagct aatctcttaa agccaatctc   1200
agttcggatt gtaggctgca actcgcctac atgaagtcgg aatcgctagt aatcgcggat   1260
cagcacgccg cggtgaatac gttcccgggc cttgtacaca ccgcccgtca caccacgaga   1320
gtttgtaaca cccga                                                    1335
```

<210> SEQ ID NO 55
<211> LENGTH: 1335
<212> TYPE: DNA
<213> ORGANISM: Streptococcus pyogenes

<400> SEQUENCE: 55

```
gaacgggtga gtaacgcgta ggtaacctac ctcatagcgg gggataacta ttggaaacga    60
```

-continued

```
tagctaatac cgcataagag agactaacgc atgttagtaa tttaaaaggg gcaattgctc      120
cactatgaga tggacctgcg ttgtattagc tagttggtga ggtaaaggct caccaaggcg      180
acgatacata gccgacctga gagggtgatc ggccacactg ggactgagac acggcccaga      240
ctcctacggg aggcagcagt agggaatctt cggcaatggg ggcaaccctg accgagcaac      300
gccgcgtgag tgaagaaggt tttcggatcg taaagctctg ttgttagaga agaatgatgg      360
tgggagtgga aaatccacca agtgacggta actaaccaga aagggacggc taactacgtg      420
ccagcagccg cggtaatacg taggtcccga gcgttgtccg gatttattgg gcgtaaagcg      480
agcgcaggcg gtttttttaag tctgaagtta aaggcattgg ctcaaccaat gtacgctttg      540
gaaactggag aacttgagtg cagaagggga gagtggaatt ccatgtgtag cggtgaaatg      600
cgtagatata tggaggaaca ccagtggcga aagcggctct ctggtctgta actgacgctg      660
aggctcgaaa gcgtggggag caaacaggat tagatacccct ggtagtccac gccgtaaacg      720
atgagtgcta ggtgttaggc cctttccggg gcttagtgcc ggagctaacg cattaagcac      780
tccgcctggg gagtacgacc gcaaggttga aactcaaagg aattgacggg ggcccgcaca      840
agcggtggag catgtggttt aattcgaagc aacgcgaaga accttaccag gtcttgacat      900
cccgatgccc gctctagaga tagagtttta cttcggtaca tcggtgacag gtggtgcatg      960
gttgtcgtca gctcgtgtcg tgagatgttg ggttaagtcc cgcaacgagc gcaacccta     1020 ttgttagttg ccatcattaa gttgggcact ctagcgagac tgccggtaat aaaccggagg     1080 aaggtggggga tgacgtcaaa tcatcatgcc ccttatgacc tgggctacac acgtgctaca     1140
atggttggta caacgagtcg caagccggtg acggcaagct aatctcttaa agccaatctc     1200
agttcggatt gtaggctgca actcgcctac atgaagtcgg aatcgctagt aatcgcggat     1260
cagcacgccg cggtgaatac gttcccgggc cttgtacaca ccgcccgtca caccacgaga     1320
gtttgtaaca cccga                                                      1335
```

<210> SEQ ID NO 56
<211> LENGTH: 1335
<212> TYPE: DNA
<213> ORGANISM: Streptococcus pyogenes

<400> SEQUENCE: 56

```
gaacgggtga gtaacgcgta ggtaacctac ctcatagcgg gggataacta ttggaaacga       60
tagctaatac cgcataagag agactaacgc atgttagtaa tttaaaaggg gcaattgctc      120
cactatgaga tggacctgcg ttgtattagc tagttggtga ggtaaaggct caccaaggcg      180
acgatacata gccgacctga gagggtgatc ggccacactg ggactgagac acggcccaga      240
ctcctacggg aggcagcagt agggaatctt cggcaatggg ggcaaccctg accgagcaac      300
gccgcgtgag tgaagaaggt tttcggatcg taaagctctg ttgttagaga agaatgatgg      360
tgggagtgga aaatccacca agtgacggta actaaccaga aagggacggc taactacgtg      420
ccagcagccg cggtaatacg taggtcccga gcgttgtccg gatttattgg gcgtaaagcg      480
agcgcaggcg gtttttttaag tctgaagtta aaggcattgg ctcaaccaat gtacgctttg      540
gaaactggag aacttgagtg cagaagggga gagtggaatt ccatgtgtag cggtgaaatg      600
cgtagatata tggaggaaca ccagtggcga aagcggctct ctggtctgta actgacgctg      660
aggctcgaaa gcgtggggag caaacaggat tagatacccct ggtagtccac gccgtaaacg      720
atgagtgcta ggtgttaggc cctttccggg gcttagtgcc ggagctaacg cattaagcac      780
tccgcctggg gagtacgacc gcaaggttga aactcaaagg aattgacggg ggcccgcaca      840
```

-continued

```
agcggtggag catgtggttt aattcgaagc aacgcgaaga accttaccag gtcttgacat    900
cccgatgccc gctctagaga tagagtttta cttcggtaca tcggtgacag gtggtgcatg    960
gttgtcgtca gctcgtgtcg tgagatgttg ggttaagtcc cgcaacgagc gcaaccccta   1020
ttgttagttg ccatcattaa gttgggcact ctagcgagac tgccggtaat aaaccggagg   1080
aaggtgggga tgacgtcaaa tcatcatgcc ccttatgacc tgggctacac acgtgctaca   1140
atggttggta caacgagtcg caagccggtg acggcaagct aatctcttaa agccaatctc   1200
agttcggatt gtaggctgca actcgcctac atgaagtcgg aatcgctagt aatcgcggat   1260
cagcacgccg cggtgaatac gttcccgggc cttgtacaca ccgcccgtca caccacgaga   1320
gtttgtaaca cccga                                                   1335
```

<210> SEQ ID NO 57
<211> LENGTH: 1335
<212> TYPE: DNA
<213> ORGANISM: Streptococcus pyogenes

<400> SEQUENCE: 57

```
gaacgggtga gtaacgcgta ggtaacctac ctcatagcgg gggataacta ttggaaacga    60
tagctaatac cgcataagag agactaacgc atgttagtaa tttaaaaggg gcaattgctc   120
cactatgaga tggacctgcg ttgtattagc tagttggtga ggtaaaggct caccaaggcg   180
acgatacata gccgacctga gagggtgatc ggccacactg ggactgagac acggcccaga   240
ctcctacggg aggcagcagt agggaatctt cggcaatggg ggcaaccctg accgagcaac   300
gccgcgtgag tgaagaaggt tttcggatcg taaagctctg ttgttagaga agaatgatgg   360
tgggagtgga aaatccacca agtgacggta actaaccaga aagggacggc taactacgtg   420
ccagcagccg cggtaatacg taggtcccga gcgttgtccg gatttattgg gcgtaaagcg   480
agcgcaggcg gttttttaag tctgaagtta aaggcattgg ctcaaccaat gtacgctttg   540
gaaactggag aacttgagtg cagaagggga gagtggaatt ccatgtgtag cggtgaaatg   600
cgtagatata tggaggaaca ccagtggcga aagcggctct ctggtctgta actgacgctg   660
aggctcgaaa gcgtggggag caaacaggat tagataccct ggtagtccac gccgtaaacg   720
atgagtgcta ggtgttaggc cctttccggg gcttagtgcc ggagctaacg cattaagcac   780
tccgcctggg gagtacgacc gcaaggttga aactcaaagg aattgacggg ggcccgcaca   840
agcggtggag catgtggttt aattcgaagc aacgcgaaga accttaccag gtcttgacat    900
cccgatgccc gctctagaga tagagtttta cttcggtaca tcggtgacag gtggtgcatg    960
gttgtcgtca gctcgtgtcg tgagatgttg ggttaagtcc cgcaacgagc gcaaccccta   1020
ttgttagttg ccatcattaa gttgggcact ctagcgagac tgccggtaat aaaccggagg   1080
aaggtgggga tgacgtcaaa tcatcatgcc ccttatgacc tgggctacac acgtgctaca   1140
atggttggta caacgagtcg caagccggtg acggcaagct aatctcttaa agccaatctc   1200
agttcggatt gtaggctgca actcgcctac atgaagtcgg aatcgctagt aatcgcggat   1260
cagcacgccg cggtgaatac gttcccgggc cttgtacaca ccgcccgtca caccacgaga   1320
gtttgtaaca cccga                                                   1335
```

<210> SEQ ID NO 58
<211> LENGTH: 1335
<212> TYPE: DNA
<213> ORGANISM: Streptococcus pyogenes

<400> SEQUENCE: 58

```
gaacgggtga gtaacgcgta ggtaacctac ctcatagcgg gggataacta ttggaaacga      60
tagctaatac cgcataagag agactaacgc atgttagtaa tttaaaaggg gcaattgctc     120
cactatgaga tggacctgcg ttgtattagc tagttggtga ggtaaaggct caccaaggcg     180
acgatacata gccgacctga gagggtgatc ggccacactg ggactgagac acggcccaga    240
ctcctacggg aggcagcagt agggaatctt cggcaatggg ggcaaccctg accgagcaac    300
gccgcgtgag tgaagaaggt tttcggatcg taaagctctg ttgttagaga agaatgatgg    360
tgggagtgga aaatccacca agtgacggta actaaccaga aagggacggc taactacgtg    420
ccagcagccg cggtaatacg taggtcccga gcgttgtccg gatttattgg gcgtaaagcg    480
agcgcaggcg gtttttttaag tctgaagtta aaggcattgg ctcaaccaat gtacgctttg    540
gaaactggag aacttgagtg cagaaggga gagtggaatt ccatgtgtag cggtgaaatg    600
cgtagatata tggaggaaca ccagtggcga aagcggctct ctggtctgta actgacgctg    660
aggctcgaaa gcgtggggag caaacaggat tagataccct ggtagtccac gccgtaaacg    720
atgagtgcta ggtgttaggc cctttccggg gcttagtgcc ggagctaacg cattaagcac    780
tccgcctggg gagtacgacc gcaaggttga aactcaaagg aattgacggg ggcccgcaca    840
agcggtggag catgtggttt aattcgaagc aacgcgaaga accttaccag gtcttgacat    900
cccgatgccc gctctagaga tagagtttta cttcggtaca tcggtgacag gtggtgcatg    960
gttgtcgtca gctcgtgtcg tgagatgttg ggttaagtcc cgcaacgagc gcaacccta  1020
ttgttagttg ccatcattaa gttgggcact ctagcgagac tgccggtaat aaaccggagg   1080
aaggtgggga tgacgtcaaa tcatcatgcc ccttatgacc tgggctacac acgtgctaca   1140
atggttggta caacgagtcg caagccggtg acggcaagct aatctcttaa agccaatctc   1200
agttcggatt gtaggctgca actcgcctac atgaagtcgg aatcgctagt aatcgcggat   1260
cagcacgccg cggtgaatac gttcccgggc cttgtacaca ccgcccgtca caccacgaga   1320
gtttgtaaca cccga                                                    1335
```

<210> SEQ ID NO 59
<211> LENGTH: 1335
<212> TYPE: DNA
<213> ORGANISM: Streptococcus pyogenes

<400> SEQUENCE: 59

```
gaacgggtga gtaacgcgta ggtaacctac ctcatagcgg gggataacta ttggaaacga      60
tagctaatac cgcataagag agactaacgc atgttagtaa tttaaaaggg gcaattgctc     120
cactatgaga tggacctgcg ttgtattagc tagttggtga ggtaaaggct caccaaggcg    180
acgatacata gccgacctga gagggtgatc ggccacactg ggactgagac acggcccaga    240
ctcctacggg aggcagcagt agggaatctt cggcaatggg ggcaaccctg accgagcaac    300
gccgcgtgag tgaagaaggt tttcggatcg taaagctctg ttgttagaga agaatgatgg    360
tgggagtgga aaatccacca agtgacggta actaaccaga aagggacggc taactacgtg    420
ccagcagccg cggtaatacg taggtcccga gcgttgtccg gatttattgg gcgtaaagcg    480
agcgcaggcg gtttttttaag tctgaagtta aaggcattgg ctcaaccaat gtacgctttg    540
gaaactggag aacttgagtg cagaaggga gagtggaatt ccatgtgtag cggtgaaatg    600
cgtagatata tggaggaaca ccggtggcga aagcggctct ctggtctgta actgacgctg    660
aggctcgaaa gcgtggggag caaacaggat tagataccct ggtagtccac gccgtaaacg    720
```

```
atgagtgcta ggtgttaggc cctttccggg gcttagtgcc ggagctaacg cattaagcac        780
tccgcctggg gagtacgacc gcaaggttga aactcaaagg aattgacggg ggcccgcaca        840
agcggtggag catgtggttt aattcgaagc aacgcgaaga accttaccag gtcttgacat        900
cccgatgccc gctctagaga tagagtttta cttcggtaca tcggtgacag gtggtgcatg        960
gttgtcgtca gctcgtgtcg tgagatgttg ggttaagtcc cgcaacgagc gcaaccccta       1020
ttgttagttg ccatcattaa gttgggcact ctagcgagac tgccggtaat aaaccggagg       1080
aaggtgggga tgacgtcaaa tcatcatgcc ccttatgacc tgggctacac acgtgctaca       1140
atggttggta caacgagtcg caagccggtg acggcaagct aatctcttaa agccaatctc       1200
agttcggatt gtaggctgca actcgcctac atgaagtcgg aatcgctagt aatcgcggat       1260
cagcacgccg cggtgaatac gttcccgggc cttgtacaca ccgcccgtca caccacgaga       1320
gtttgtaaca cccga                                                        1335

<210> SEQ ID NO 60
<211> LENGTH: 1335
<212> TYPE: DNA
<213> ORGANISM: Streptococcus pyogenes

<400> SEQUENCE: 60
gaacgggtga gtaacgcgta ggtaacctac ctcatagcgg gggataacta ttggaaacga        60
tagctaatac cgcataagag agactaacgc atgttagtaa tttaaaaggg gcaattgctc       120
cactatgaga tggacctgcg ttgtattagc tagttggtga ggtaaaggct caccaaggcg       180
acgatacata gccgacctga gagggtgatc ggccacactg ggactgagac acggcccaga       240
ctcctacggg aggcagcagt agggaatctt cggcaatggg ggcaaccctg accgagcaac       300
gccgcgtgag tgaagaaggt tttcggatcg taaagctctg ttgttagaga agaatgatgg       360
tgggagtgga aaatccacca agtgacggta actaaccaga aagggacggc taactacgtg       420
ccagcagccg cggtaatacg taggtcccga gcgttgtccg gatttattgg gcgtaaagcg       480
agcgcaggcg gtttttttaag tctgaagtta aaggcattgg ctcaaccaat gtacgctttg       540
gaaactggag aacttgagtg cagaagggga gagtggaatt ccatgtgtag cggtgaaatg       600
cgtagatata tggaggaaca ccggtggcga aagcggctct ctggtctgta actgacgctg       660
aggctcgaaa gcgtggggag caaacaggat tagataccct ggtagtccac gccgtaaacg       720
atgagtgcta ggtgttaggc cctttccggg gcttagtgcc ggagctaacg cattaagcac       780
tccgcctggg gagtacgacc gcaaggttga aactcaaagg aattgacggg ggcccgcaca       840
agcggtggag catgtggttt aattcgaagc aacgcgaaga accttaccag gtcttgacat       900
cccgatgccc gctctagaga tagagtttta cttcggtaca tcggtgacag gtggtgcatg       960
gttgtcgtca gctcgtgtcg tgagatgttg ggttaagtcc cgcaacgagc gcaaccccta      1020
ttgttagttg ccatcattaa gttgggcact ctagcgagac tgccggtaat aaaccggagg      1080
aaggtgggga tgacgtcaaa tcatcatgcc ccttatgacc tgggctacac acgtgctaca      1140
atggttggta caacgagtcg caagccggtg acggcaagct aatctcttaa agccaatctc      1200
agttcggatt gtaggctgca actcgcctac atgaagtcgg aatcgctagt aatcgcggat      1260
cagcacgccg cggtgaatac gttcccgggc cttgtacaca ccgcccgtca caccacgaga      1320
gtttgtaaca cccga                                                       1335

<210> SEQ ID NO 61
```

<211> LENGTH: 1335
<212> TYPE: DNA
<213> ORGANISM: Streptococcus pyogenes

<400> SEQUENCE: 61

```
gaacgggtga gtaacgcgta ggtaacctac ctcatagcgg gggataacta ttggaaacga      60
tagctaatac cgcataagag agactaacgc atgttagtaa tttaaaaggg gcaattgctc     120
cactatgaga tggacctgcg ttgtattagc tagttggtga ggtaaaggct caccaaggcg     180
acgatacata gccgacctga gagggtgatc ggccacactg ggactgagac acggcccaga     240
ctcctacggg aggcagcagt agggaatctt cggcaatggg ggcaaccctg accgagcaac     300
gccgcgtgag tgaagaaggt tttcggatcg taaagctctg ttgttagaga agaatgatgg     360
tgggagtgga aaatccacca agtgacggta actaaccaga aagggacggc taactacgtg     420
ccagcagccg cggtaatacg taggtcccga gcgttgtccg gatttattgg gcgtaaagcg     480
agcgcaggcg gtttttttaag tctgaagtta aaggcattgg ctcaaccaat gtacgctttg     540
gaaactggag aacttgagtg cagaaggggga gagtggaatt ccatgtgtag cggtgaaatg     600
cgtagatata tggaggaaca ccggtggcga aagcggctct ctggtctgta actgacgctg     660
aggctcgaaa gcgtggggag caaacaggat tagataccct ggtagtccac gccgtaaacg     720
atgagtgcta ggtgttaggc cctttccggg gcttagtgcc ggagctaacg cattaagcac     780
tccgcctggg gagtacgacc gcaaggttga aactcaaagg aattgacggg ggcccgcaca     840
agcggtggag catgtggttt aattcgaagc aacgcgaaga accttaccag gtcttgacat     900
cccgatgccc gctctagaga tagagtttta cttcggtaca tcggtgacag gtggtgcatg     960
gttgtcgtca gctcgtgtcg tgagatgttg ggttaagtcc cgcaacgagc gcaaccccta    1020
ttgttagttg ccatcattaa gttgggcact ctagcgagac tgccggtaat aaaccggagg    1080
aaggtgggga tgacgtcaaa tcatcatgcc ccttatgacc tgggctacac acgtgctaca    1140
atggttggta caacgagtcg caagccggtg acggcaagct aatctcttaa agccaatctc    1200
agttcggatt gtaggctgca actcgcctac atgaagtcgg aatcgctagt aatcgcggat    1260
cagcacgccg cggtgaatac gttcccgggc cttgtacaca ccgcccgtca caccacgaga    1320
gtttgtaaca cccga                                                     1335
```

<210> SEQ ID NO 62
<211> LENGTH: 1335
<212> TYPE: DNA
<213> ORGANISM: Streptococcus pyogenes

<400> SEQUENCE: 62

```
gaacgggtga gtaacgcgta ggtaacctac ctcatagcgg gggataacta ttggaaacga      60
tagctaatac cgcataagag agactaacgc atgttagtaa tttaaaaggg gcaattgctc     120
cactatgaga tggacctgcg ttgtattagc tagttggtga ggtaaaggct caccaaggcg     180
acgatacata gccgacctga gagggtgatc ggccacactg ggactgagac acggcccaga     240
ctcctacggg aggcagcagt agggaatctt cggcaatggg ggcaaccctg accgagcaac     300
gccgcgtgag tgaagaaggt tttcggatcg taaagctctg ttgttagaga agaatgatgg     360
tgggagtgga aaatccacca agtgacggta actaaccaga aagggacggc taactacgtg     420
ccagcagccg cggtaatacg taggtcccga gcgttgtccg gatttattgg gcgtaaagcg     480
agcgcaggcg gtttttttaag tctgaagtta aaggcattgg ctcaaccaat gtacgctttg     540
gaaactggag aacttgagtg cagaaggggga gagtggaatt ccatgtgtag cggtgaaatg     600
```

-continued

```
cgtagatata tggaggaaca ccggtggcga aagcggctct ctggtctgta actgacgctg    660
aggctcgaaa gcgtggggag caaacaggat tagataccct ggtagtccac gccgtaaacg    720
atgagtgcta ggtgttaggc cctttccggg gcttagtgcc ggagctaacg cattaagcac    780
tccgcctggg gagtacgacc gcaaggttga aactcaaagg aattgacggg ggcccgcaca    840
agcggtggag catgtggttt aattcgaagc aacgcgaaga accttaccag gtcttgacat    900
cccgatgccc gctctagaga tagagttttta cttcggtaca tcggtgacag gtggtgcatg    960
gttgtcgtca gctcgtgtcg tgagatgttg ggttaagtcc cgcaacgagc gcaaccccta   1020
ttgttagttg ccatcattaa gttgggcact ctagcgagac tgccggtaat aaaccggagg   1080
aaggtgggga tgacgtcaaa tcatcatgcc ccttatgacc tgggctacac acgtgctaca   1140
atggttggta caacgagtcg caagccggtg acggcaagct aatctcttaa agccaatctc   1200
agttcggatt gtaggctgca actcgcctac atgaagtcgg aatcgctagt aatcgcggat   1260
cagcacgccg cggtgaatac gttcccgggc cttgtacaca ccgcccgtca caccacgaga   1320
gtttgtaaca cccga                                                    1335
```

<210> SEQ ID NO 63
<211> LENGTH: 1338
<212> TYPE: DNA
<213> ORGANISM: Streptococcus pyogenes

<400> SEQUENCE: 63

```
tgcgaacggg tgagtaacgc gtaggtaacc tacctcatag cggggataa ctattggaaa     60
cgatagctaa taccgcataa gagagactaa cgcatgttag taatttaaaa ggggcaattg    120
ctccactatg agatggacct gcgttgtatt agctagttgg tgaggtaaag gctcaccaag    180
gcgacgatac atagccgacc tgagagggtg atcggccaca ctgggactga cacggccc     240
agactcctac gggaggcagc agtagggaat cttcggcaat gggggcaacc ctgaccgagc    300
aacgccgcgt gagtgaagaa ggttttcgga tcgtaaagct ctgttgttag agaagaatga    360
tggtgggagt ggaaaatcca ccaagtgacg gtaactaacc agaaagggac ggctaactac    420
gtgccagcag ccgcggtaat acgtaggtcc cgagcgttgt ccggatttat tgggcgtaaa    480
gcgagcgcag gcggtttttt aagtctgaag ttaaaggcat tggctcaacc aatgtacgct    540
ttggaaactg gagaacttga gtgcagaagg ggagagtgga attccatgtg tagcggtgaa    600
atgcgtagat atatggagga acaccggtgg cgaaagcggc tctctggtct gtaactgacg    660
ctgaggctcg aaagcgtggg gagcaaacag gattagatac cctggtagtc cacgccgtaa    720
acgatgagtg ctaggtgtta ggccctttcc ggggcttagt gccggagcta acgcattaag    780
cactccgcct ggggagtacg accgcaaggt tgaaactcaa aggaattgac ggggcccgc    840
acaagcggtg gagcatgtgg tttaattcga agcaacgcga gaaccttac caggtcttga    900
catcccgatg cccgctctag agatagagtt ttacttcggt acatcggtga caggtggtgc    960
atggttgtcg tcagctcgtg tcgtgagatg ttgggttaag tcccgcaacg agcgcaaccc   1020
ctattgttag ttgccatcat taagttgggc actctagcga gactgccggt aataaaccgg   1080
aggaaggtgg ggatgacgtc aaatcatcat gccccttatg acctgggcta cacacgtgct   1140
acaatggttg gtacaacgag tcgcaagccg gtgacggcaa gctaatctct taaagccaat   1200
ctcagttcgg attgtaggct gcaactcgcc tacatgaagt cggaatcgct agtaatcgcg   1260
gatcagcacg ccgcggtgaa tacgttcccg ggccttgtac acaccgcccg tcacaccacg   1320
```

```
agagtttgta acacccga                                                  1338
```

<210> SEQ ID NO 64
<211> LENGTH: 1550
<212> TYPE: DNA
<213> ORGANISM: Streptococcus pyogenes

<400> SEQUENCE: 64

```
ttaaagagag tttgatcctg gctcaggacg aacgctggcg gcgtgcctaa tacatgcaag      60
tagaacgctg agaactggtg cttgcaccgg ttcaaggagt tgcgaacggg tgagtaacgc     120
gtaggtaacc tacctcatag cgggggataa ctattggaaa cgatagctaa taccgcataa     180
gagagactaa cgcatgttag taatttaaaa ggggcaattg ctccactatg agatggacct     240
gcgttgtatt agctagttgg tgaggtaaag gctcaccaag gcgacgatac atagccgacc     300
tgagagggtg atcggccaca ctgggactga gacacggccc agactcctac gggaggcagc     360
agtagggaat cttcggcaat gggggcaacc ctgaccgagc aacgccgcgt gagtgaagaa     420
ggttttcgga tcgtaaagct ctgttgttag agaagaatga tggtgggagt ggaaaatcca     480
ccaagtgacg gtaactaacc agaaagggac ggctaactac gtgccagcag ccgcggtaat     540
acgtaggtcc cgagcgttgt ccggatttat tgggcgtaaa gcgagcgcag gcggttttt      600
aagtctgaag ttaaaggcat tggctcaacc aatgtacgct ttggaaactg agaacttga     660
gtgcagaagg ggagagtgga attccatgtg tagcggtgaa atgcgtagat atatggagga     720
acaccggtgg cgaaagcggc tctctggtct gtaactgacg ctgaggctcg aaagcgtggg     780
gagcaaacag gattagatac cctggtagtc cacgccgtaa acgatgagtg ctaggtgtta     840
ggccctttcc ggggcttagt gccggagcta acgcattaag cactccgcct ggggagtacg     900
accgcaaggt tgaaactcaa aggaattgac ggggcccgc acaagcggtg gagcatgtgg      960
tttaattcga agcaacgcga agaaccttac caggtcttga catcccgatg cccgctctag    1020
agatagagtt ttacttcggt acatcggtga caggtggtgc atggttgtcg tcagctcgtg    1080
tcgtgagatg ttgggttaag tcccgcaacg agcgcaaccc ctattgttag ttgccatcat    1140
taagttgggc actctagcga gactgccggt aataaaccgg aggaaggtgg ggatgacgtc    1200
aaatcatcat gccccttatg acctgggcta cacacgtgct acaatggttg gtacaacgag    1260
tcgcaagtcg gtgacggcaa gctaatctct taaagccaat ctcagttcgg attgtaggct    1320
gcaactcgcc tacatgaagt cggaatcgct agtaatcgcg gatcagcacg ccgcggtgaa    1380
tacgttcccg ggccttgtac acaccgcccg tcacaccacg agagtttgta acacccgaag    1440
tcggtgaggt aacctattag gagccagccg cctaaggtgg gatagatgat tggggtgaag    1500
tcgtaacaag gtagccgtat cggaaggtgc ggctggatca cctcctttct              1550
```

<210> SEQ ID NO 65
<211> LENGTH: 1550
<212> TYPE: DNA
<213> ORGANISM: Streptococcus pyogenes

<400> SEQUENCE: 65

```
ttaaagagag tttgatcctg gctcaggacg aacgctggcg gcgtgcctaa tacatgcaag      60
tagaacgctg agaactggtg cttgcaccgg ttcaaggagt tgcgaacggg tgagtaacgc     120
gtaggtaacc tacctcatag cgggggataa ctattggaaa cgatagctaa taccgcataa     180
gagagactaa cgcatgttag taatttaaaa ggggcaattg ctccactatg agatggacct     240
gcgttgtatt agctagttgg tgaggtaaag gctcaccaag gcgacgatac atagccgacc     300
```

```
tgagagggtg atcggccaca ctgggactga gacacggccc agactcctac gggaggcagc      360
agtagggaat cttcggcaat gggggcaacc ctgaccgagc aacgccgcgt gagtgaagaa      420
ggttttcgga tcgtaaagct ctgttgttag agaagaatga tggtgggagt ggaaaatcca      480
ccaagtgacg gtaactaacc agaaagggac ggctaactac gtgccagcag ccgcggtaat      540
acgtaggtcc cgagcgttgt ccggatttat tgggcgtaaa gcgagcgcag gcggtttttt      600
aagtctgaag ttaaaggcat tggctcaacc aatgtacgct ttggaaactg agaacttga       660 gtgcagaagg ggagagtgga attccatgtg tagcggtgaa atgcgtagat atatggagga     720
acaccggtgg cgaaagcggc tctctggtct gtaactgacg ctgaggctcg aaagcgtggg     780
gagcaaacag gattagatac cctggtagtc cacgccgtaa acgatgagtg ctaggtgtta    840
ggccctttcc ggggcttagt gccggagcta acgcattaag cactccgcct ggggagtacg     900
accgcaaggt tgaaactcaa aggaattgac ggggcccgc acaagcggtg gagcatgtgg      960
tttaattcga agcaacgcga gaaccttac caggtcttga catcccgatg cccgctctag     1020
agatagagtt ttacttcggt acatcggtga caggtggtgc atggttgtcg tcagctcgtg    1080
tcgtgagatg ttgggttaag tcccgcaacg agcgcaaccc ctattgttag ttgccatcat   1140
taagttgggc actctagcga gactgccggt aataaaccgg aggaaggtgg ggatgacgtc   1200
aaatcatcat gccccttatg acctgggcta cacacgtgct acaatggttg gtacaacgag   1260
tcgcaagtcg gtgacggcaa gctaatctct aaagccaat ctcagttcgg attgtaggct     1320
gcaactcgcc tacatgaagt cggaatcgct agtaatcgcg gatcagcacg ccgcggtgaa   1380
tacgttcccg ggccttgtac acaccgcccg tcacaccacg agagtttgta acacccgaag    1440
tcggtgaggt aacctattag gagccagccg cctaaggtgg gatagatgat tggggtgaag   1500
tcgtaacaag gtagccgtat cggaaggtgc ggctggatca cctcctttct                1550
```

<210> SEQ ID NO 66
<211> LENGTH: 1550
<212> TYPE: DNA
<213> ORGANISM: Streptococcus pyogenes

<400> SEQUENCE: 66

```
ttaaagagag tttgatcctg gctcaggacg aacgctggcg gcgtgcctaa tacatgcaag     60
tagaacgctg agaactggtg cttgcaccgg ttcaaggagt tgcgaacggg tgagtaacgc    120
gtaggtaacc tacctcatag cggggataa ctattggaaa cgatagctaa taccgcataa   180
gagagactaa cgcatgttag taatttaaaa ggggcaattg ctccactatg agatggacct    240
gcgttgtatt agctagttgg tgaggtaaag gctcaccaag gcgacgatac atagccgacc    300
tgagagggtg atcggccaca ctgggactga gacacggccc agactcctac gggaggcagc   360
agtagggaat cttcggcaat gggggcaacc ctgaccgagc aacgccgcgt gagtgaagaa    420
ggttttcgga tcgtaaagct ctgttgttag agaagaatga tggtgggagt ggaaaatcca    480
ccaagtgacg gtaactaacc agaaagggac ggctaactac gtgccagcag ccgcggtaat    540
acgtaggtcc cgagcgttgt ccggatttat tgggcgtaaa gcgagcgcag gcggtttttt    600
aagtctgaag ttaaaggcat tggctcaacc aatgtacgct ttggaaactg agaacttga     660 gtgcagaagg ggagagtgga attccatgtg tagcggtgaa atgcgtagat atatggagga   720
acaccggtgg cgaaagcggc tctctggtct gtaactgacg ctgaggctcg aaagcgtggg    780
gagcaaacag gattagatac cctggtagtc cacgccgtaa acgatgagtg ctaggtgtta    840
```

| ggcccttttcc | ggggcttagt | gccggagcta | acgcattaag | cactccgcct | ggggagtacg | 900 |

| accgcaaggt | tgaaactcaa | aggaattgac | ggggcccgc | acaagcggtg | gagcatgtgg | 960 |

| tttaattcga | agcaacgcga | agaaccttac | caggtcttga | catcccgatg | cccgctctag | 1020 |

| agatagagtt | ttacttcggt | acatcggtga | caggtggtgc | atggttgtcg | tcagctcgtg | 1080 |

| tcgtgagatg | ttgggttaag | tcccgcaacg | agcgcaaccc | ctattgttag | ttgccatcat | 1140 |

| taagttgggc | actctagcga | gactgccggt | aataaaccgg | aggaaggtgg | ggatgacgtc | 1200 |

| aaatcatcat | gccccttatg | acctgggcta | cacacgtgct | acaatggttg | gtacaacgag | 1260 |

| tcgcaagtcg | gtgacggcaa | gctaatctct | taaagccaat | ctcagttcgg | attgtaggct | 1320 |

| gcaactcgcc | tacatgaagt | cggaatcgct | agtaatcgcg | gatcagcacg | ccgcggtgaa | 1380 |

| tacgttcccg | ggccttgtac | acaccgcccg | tcacaccacg | agagtttgta | acacccgaag | 1440 |

| tcggtgaggt | aacctattag | gagccagccg | cctaaggtgg | gatagatgat | tggggtgaag | 1500 |

| tcgtaacaag | gtagccgtat | cggaaggtgc | ggctggatca | cctccttcct | | 1550 |

<210> SEQ ID NO 67
<211> LENGTH: 1550
<212> TYPE: DNA
<213> ORGANISM: Streptococcus pyogenes

<400> SEQUENCE: 67

| ttaaagagag | tttgatcctg | gctcaggacg | aacgctggcg | gcgtgcctaa | tacatgcaag | 60 |

| tagaacgctg | agaactggtg | cttgcaccgg | ttcaaggagt | tgcgaacggg | tgagtaacgc | 120 |

| gtaggtaacc | tacctcatag | cggggggataa | ctattggaaa | cgatagctaa | taccgcataa | 180 |

| gagagactaa | cgcatgttag | taattttaaaa | ggggcaattg | ctccactatg | agatggacct | 240 |

| gcgttgtatt | agctagttgg | tgaggtaaag | gctcaccaag | gcgacgatac | atagccgacc | 300 |

| tgagagggtg | atcggccaca | ctgggactga | gacacggccc | agactcctac | gggaggcagc | 360 |

| agtagggaat | cttcggcaat | ggggcaacc | ctgaccgagc | aacgccgcgt | gagtgaagaa | 420 |

| ggttttcgga | tcgtaaagct | ctgttgttag | agaagaatga | tagtgggagt | ggaaaatcca | 480 |

| ccaagtgacg | gtaactaacc | agaaagggac | ggctaactac | gtgccagcag | ccgcggtaat | 540 |

| acgtaggtcc | cgagcgttgt | ccggatttat | tgggcgtaaa | gcgagcgcag | gcggttttt | 600 |

| aagtctgaag | ttaaaggcat | tggctcaacc | aatgtacgct | ttggaaactg | gagaacttga | 660 |

| gtgcagaagg | ggagagtgga | attccatgtg | tagcggtgaa | atgcgtagat | atatggagga | 720 |

| acaccggtgg | cgaaagcggc | tctctggtct | gtaactgacg | ctgaggctcg | aaagcgtggg | 780 |

| gagcaaacag | gattagatac | cctggtagtc | cacgccgtaa | acgatgagtg | ctaggtgtta | 840 |

| ggccctttcc | ggggcttagt | gccggagcta | acgcattaag | cactccgcct | ggggagtacg | 900 |

| accgcaaggt | tgaaactcaa | aggaattgac | ggggcccgc | acaagcggtg | gagcatgtgg | 960 |

| tttaattcga | agcaacgcga | agaaccttac | caggtcttga | catcccgatg | cccgctctag | 1020 |

| agatagagtt | ttacttcggt | acatcggtga | caggtggtgc | atggttgtcg | tcagctcgtg | 1080 |

| tcgtgagatg | ttgggttaag | tcccgcaacg | agcgcaaccc | ctattgttag | ttgccatcat | 1140 |

| taagttgggc | actctagcga | gactgccggt | aataaaccgg | aggaaggtgg | ggatgacgtc | 1200 |

| aaatcatcat | gccccttatg | acctgggcta | cacacgtgct | acaatggttg | gtacaacgag | 1260 |

| tcgcaagtcg | gtgacggcaa | gctaatctct | taaagccaat | ctcagttcgg | attgtaggct | 1320 |

| gcaactcgcc | tacatgaagt | cggaatcgct | agtaatcgcg | gatcagcacg | ccgcggtgaa | 1380 |

| tacgttcccg | ggccttgtac | acaccgcccg | tcacaccacg | agagtttgta | acacccgaag | 1440 |

```
tcggtgaggt aacctattag gagccagccg cctaaggtgg gatagatgat tggggtgaag    1500
tcgtaacaag gtagccgtat cggaaggtgc ggctggatca cctcctttct              1550

<210> SEQ ID NO 68
<211> LENGTH: 1550
<212> TYPE: DNA
<213> ORGANISM: Streptococcus pyogenes

<400> SEQUENCE: 68
ttaaagagag tttgatcctg gctcaggacg aacgctggcg gcgtgcctaa tacatgcaag      60
tagaacgctg agaactggtg cttgcaccgg ttcaaggagt tgcgaacggg tgagtaacgc     120
gtaggtaacc tacctcatag cggggggataa ctattggaaa cgatagctaa taccgcataa    180
gagagactaa cgcatgttag taatttaaaa ggggcaattg ctccactatg agatggacct    240
gcgttgtatt agctagttgg tgaggtaaag gctcaccaag cgacgatac atagccgacc      300 tgagagggtg atcggccaca ctgggactga gacacggccc agactcctac gggaggcagc    360
agtagggaat cttcggcaat gggggcaacc ctgaccgagc aacgccgcgt gagtgaagaa    420
ggttttcgga tcgtaaagct ctgttgttag agaagaatga tggtgggagt ggaaaatcca    480
ccaagtgacg gtaactaacc agaaagggac ggctaactac gtgccagcag ccgcggtaat    540
acgtaggtcc cgagcgttgt ccggatttat tgggcgtaaa gcgagcgcag gcggtttttt    600
aagtctgaag ttaaaggcat tggctcaacc aatgtacgct ttggaaactg agaacttga    660 gtgcagaagg ggagagtgga attccatgtg tagcggtgaa atgcgtagat atatggagga    720
acaccggtgg cgaaagcggc tctctggtct gtaactgacg ctgaggctcg aaagcgtggg    780
gagcaaacag gattagatac cctggtagtc cacgccgtaa acgatgagtg ctaggtgtta    840
ggccctttcc gggcttagt gccggagcta acgcattaag cactccgcct ggggagtacg    900
accgcaaggt tgaaactcaa aggaattgac ggggcccgc acaagcggtg gagcatgtgg    960
tttaattcga agcaacgcga agaaccttac caggtcttga catcccgatg cccgctctag   1020
agatagagtt ttacttcggt acatcggtga caggtggtgc atggttgtcg tcagctcgtg   1080
tcgtgagatg ttgggttaag tcccgcaacg agcgcaaccc ctattgttag ttgccatcat   1140
taagttgggc actctagcga gactgccggt aataaaccgg aggaaggtgg ggatgacgtc   1200
aaatcatcat gccccttatg acctgggcta cacacgtgct acaatggttg gtacaacgag   1260
tcgcaagtcg gtgacggcaa gctaatctct taaagccaat ctcagttcgg attgtaggct   1320
gcaactcgcc tacatgaagt cggaatcgct agtaatcgcg gatcagcacg ccgcggtgaa   1380
tacgttcccg ggccttgtac acaccgcccg tcacaccacg agagtttgta acacccgaag   1440
tcggtgaggt aacctattag gagccagccg cctaaggtgg gatagatgat tggggtgaag   1500
tcgtaacaag gtagccgtat cggaaggtgc ggctggatca cctcctttct              1550

<210> SEQ ID NO 69
<211> LENGTH: 1550
<212> TYPE: DNA
<213> ORGANISM: Streptococcus pyogenes

<400> SEQUENCE: 69
ttaaagagag tttgatcctg gctcaggacg aacgctggcg gcgtgcctaa tacatgcaag      60
tagaacgctg agaactggtg cttgcaccgg ttcaaggagt tgcgaacggg tgagtaacgc     120
gtaggtaacc tacctcatag cggggggataa ctattggaaa cgatagctaa taccgcataa    180
```

-continued

```
gagagactaa cgcatgttag taatttaaaa ggggcaattg ctccactatg agatggacct      240
gcgttgtatt agctagttgg tgaggtaaag gctcaccaag gcgacgatac atagccgacc      300
tgagagggtg atcggccaca ctgggactga acacggccc agactcctac gggaggcagc      360
agtagggaat cttcggcaat gggggcaacc ctgaccgagc aacgccgcgt gagtgaagaa      420
ggttttcgga tcgtaaagct ctgttgttag agaagaatga tggtgggagt ggaaaatcca      480
ccaagtgacg gtaactaacc agaaagggac ggctaactac gtgccagcag ccgcggtaat      540
acgtaggtcc cgagcgttgt ccggatttat tgggcgtaaa gcgagcgcag gcggtttttt      600
aagtctgaag ttaaaggcat tggctcaacc aatgtacgct ttggaaactg agaacttga      660 gtgcagaagg ggagagtgga attccatgtg tagcggtgaa atgcgtagat atatggagga     720
acaccggtgg cgaaagcggc tctctggtct gtaactgacg ctgaggctcg aaagcgtggg     780
gagcaaacag gattagatac cctggtagtc cacgccgtaa acgatgagtg ctaggtgtta     840
ggccctttcc ggggcttagt gccggagcta acgcattaag cactccgcct ggggagtacg     900
accgcaaggt tgaaactcaa aggaattgac ggggcccgc acaagcggtg gagcatgtgg     960
tttaattcga agcaacgcga agaaccttac caggtcttga catcccgatg cccgctctag    1020
agatagagtt ttacttcggt acatcggtga caggtggtgc atggttgtcg tcagctcgtg    1080
tcgtgagatg ttgggttaag tcccgcaacg agcgcaaccc ctattgttag ttgccatcat    1140
taagttgggc actctagcga gactgccggt aataaaccgg aggaaggtgg ggatgacgtc    1200
aaatcatcat gccccttatg acctgggcta cacacgtgct acaatggttg gtacaacgag    1260
tcgcaagtcg gtgacggcaa gctaatctct taaagccaat ctcagttcgg attgtaggct    1320
gcaactcgcc tacatgaagt cggaatcgct agtaatcgcg gatcagcacg ccgcggtgaa    1380
tacgttcccg ggccttgtac acaccgcccg tcacaccacg agagtttgta acacccgaag    1440
tcggtgaggt aacctattag gagccagccg cctaaggtgg gatagatgat tggggtgaag    1500
tcgtaacaag gtagccgtat cggaaggtgc ggctggatca cctcctttct              1550
```

<210> SEQ ID NO 70
<211> LENGTH: 1546
<212> TYPE: DNA
<213> ORGANISM: Streptococcus salivarius

<400> SEQUENCE: 70

```
atgggagagt ttgatcctgg ctcaggacga acgctggcgg cgtgcctaat acatgcaagt      60
agaacgctga agagaggagc ttgctcttct tggatgagtt gcgaacgggt gagtaacgcg     120
taggtaacct gccttgtagc gggggataac tattggaaac gatagctaat accgcataac     180
aatggatgac acatgtcatt tatttgaaag ggcaattgc tccactacaa gatggacctg      240
cgttgtatta gctagtaggt gaggtaacgg ctcacctagg cgacgataca tagccgacct     300
gagagggtga tcggccacac tgggactgag acacggccca gactcctacg ggaggcagca    360
gtagggaatc ttcggcaatg ggggcaaccc tgaccgagca acgccgcgtg agtgaagaag    420
gttttcggat cgtaaagctc tgttgtaagt caagaacgag tgtgagagtg aaagttcac     480 actgtgacgg tagcttacca gaaagggacg gctaactacg tgccagcagc cgcggtaata    540
cgtaggtccc gagcgttgtc cggatttatt gggcgtaaag cgagcgcagg cggtttgata    600
agtctgaagt taaaggctgt ggctcaacca tagttcgctt tggaaactgt caaacttgag    660
tgcagaaggg gagagtggaa ttccatgtgt agcggtgaaa tgcgtagata tatggaggaa    720
caccggtggc gaaagcggct ctctggtctg taactgacgc tgaggctcga aagcgtgggg    780
```

```
agcgaacagg attagatacc ctggtagtcc acgccgtaaa cgatgagtgc taggtgttgg    840
atcctttccg ggattcagtg ccgcagctaa cgcattaagc actccgcctg gggagtacga    900
ccgcaaggtt gaaactcaaa ggaattgacg ggggcccgca caagcggtgg agcatgtggt    960
ttaattcgaa gcaacgcgaa gaaccttacc aggtcttgac atcccgatgc tatttctaga   1020
gatagaaagt tacttcggta catcggtgac aggtggtgca tggttgtcgt cagctcgtgt   1080
cgtgagatgt tgggttaagt cccgcaacga gcgcaacccc tattgttagt tgccatcatt   1140
cagttgggca ctctagcgag actgccggta ataaaccgga ggaaggtggg gatgacgtca   1200
aatcatcatg ccccttatga cctgggctac acacgtgcta caatggttgg tacaacgagt   1260
tgcgagtcgg tgacggcaag ctaatctctt aaagccaatc tcagttcgga ttgtaggctg   1320
caactcgcct acatgaagtc ggaatcgcta gtaatcgcgg atcagcacgc cgcggtgaat   1380
acgttcccgg gccttgtaca caccgcccgt cacaccacga gagtttgtaa cacccgaagt   1440
cggtgaggta acctttggga gccagccgcc taaggtggga tagatgattg gggtgaagtc   1500
gtaacaaggt agccgtatcg gaaggtgcgg ctggatcact cccttaa                 1546
```

<210> SEQ ID NO 71
<211> LENGTH: 1510
<212> TYPE: DNA
<213> ORGANISM: Streptococcus sanguis

<400> SEQUENCE: 71

```
agagtttgat catggctcag gacgaacgct ggcggcgtgc ctaatacatg caagtagaac     60
gctgaagaga ggagcttgct cttcttggat gagttgcgaa cgggtgagta acgcgtaggt    120
aacctgcctg gtagcggggg ataactattg gaaacgatag ctaataccgc ataaaattga    180
ttattgcatg ataattaatt gaaagatgca attgcatcac taccagatgg acctgcgttg    240
tattagctag ttggtgaggt aacggctcac caaggcgacg atacatagcc gacctgagag    300
ggtgatcggc cacactggga ctgagacacg gcccagactc ctacgggagg cagcagtagg    360
gaatcttcgg caatgggggg aaccctgacc gagcaacgcc gcgtgagtga agaaggtttt    420
cggatcgtaa agctctgttg taagagaaga cgggtgtgag agtggaaagt tcacactgt     480 gacggtatct taccagaaag ggacggctaa ctacgtgcca gcagccgcgg taatacgtag    540
gtcccgagcg ttgtccggat ttattgggcg taaagcgagc gcaggcggtt agataagtct    600
gaagttaaag gctgtggctt aaccatagta tgctttggaa actgtttaac ttgagtgcag    660
aaggggagag tggaattcca tgtgtagcgg tgaaatgcgt agatatatgg aggaacaccg    720
gtggcgaaag cggctctctg gtctgtaact gacgctgagg ctcgaaagcg tggggagcaa    780
acaggattag ataccctggt agtccacgcc gtaaacgatg agtgctaggt gttaggccct    840
ttccggggct tagtgccgca gctaacgcat taagcactcc gcctgggagt acgaccgca    900 aggttgaaac tcaaaggaat tgacgggggc cgcacaagc ggtggagcat gtggtttaat    960
tcgaagcaac gcgaagaacc ttaccaggtc ttgacatccc tctgaccgct ctagagatag   1020
agtttcttcg ggacagaggt gacaggtggt gcatggttgt cgtcagctcg tgtcgtgaga   1080
tgttgggtta agtcccgcaa cgagcgcaac ccctattgtt agttgccatc attcagttgg   1140
gcactctagc gagactgccg gtaataaacc ggaggaaggt ggggatgacg tcaaatcatc   1200 atgccccta tgacctgggc tacacacgtg ctacaatggc tggtacaacg agtcgcaagc   1260
cggtgacggc aagctaatct ctgaaagcca gtctcagttc ggattgtagg ctgcaactcg   1320
```

| | |
|---|---|
| cctacatgaa gtcggaatcg ctagtaatcg cgaatcagca cgccgcggtg aatacgttcc | 1380 |
| cgggccttgt acacaccgcc cgtcacacca cgagagtttg taacacccga agtcggtgag | 1440 |
| gtaaccgtaa ggagccagcc gcctaaggtg ggatagatga ttggggtgaa gtcgtaacaa | 1500 |
| ggtaaccgta | 1510 |

<210> SEQ ID NO 72
<211> LENGTH: 1358
<212> TYPE: DNA
<213> ORGANISM: Streptococcus sanguis

<400> SEQUENCE: 72

| | |
|---|---|
| cttgctcctc ttggatgagt tgcgaacggg tgagtaacgc gtaggtaacc tgcctggtag | 60 |
| cggggggataa ctattggaaa cgatagctaa taccgcataa aattgattat tgcatgataa | 120 |
| ttaattgaaa gatgcaattg catcactacc agatggacct gcgttgtatt agctagttgg | 180 |
| tgaggtaacg gctcaccaag gcgacgatac atagccgacc tgagagggtg atcggccaca | 240 |
| ctgggactga gacacggccc agactcctac gggaggcagc agtagggaat cttcggcaat | 300 |
| gggggggaacc ctgaccgagc aacgccgcgt gagtgaagaa ggttttcgga tcgtaaagct | 360 |
| ctgttgtaag agaagaacgg gtgtgagagt ggaaagttca cactgtgacg gtatcttacc | 420 |
| agaaagggac ggctaactac gtgccagcag ccgcggtaat acgtaggtcc cgagcgttgt | 480 |
| ccggatttat tgggcgtaaa gcgagcgcag gcggttagat aagtctgaag ttaaaggctg | 540 |
| tggcttaacc atagtatgct ttggaaactg tttaacttga gtgcagaagg ggagagtgga | 600 |
| attccatgtg tagcggtgaa atgcgtagat atatggagga acaccggtgg cgaaagcggc | 660 |
| tctctggtct gtaactgacg ctgaggctcg aaagcgtggg gagcaaacag gattagatac | 720 |
| ccttgtagtc cacgccgtaa acgatgagtg ctaggtgtta ggccctttcc ggggctcagt | 780 |
| gccgcagcta acgcattaag cactccgcct ggggagtacg accgcaaggt tgaaactcaa | 840 |
| aggaattgac gggggcccgc acaagcggtg gagcatgtgg tttaattcga gcaacgcga | 900 |
| ggaaccttac caggtcttga catccctatg accgctctag agatagagtt tctcttcgga | 960 |
| gcagaggtga caggtggtgc atggttgtcg tcagctcgtg tcgtgagatg ttgggttaag | 1020 |
| tcccgcaacg agcgcaaccc ctattgttag ttgccatcat tcagttgggc actctagcga | 1080 |
| gactgccggt aataaaccgg aggaaggtgg ggatgacgtc aaatcatcat gccccttatg | 1140 |
| acctgggcta cacacgtgct acaatggctg gtacaacgag tcgcaacgcg gtgacggcaa | 1200 |
| gctaatctct taaagccagt ctcagttcgg attgtaggct gcaactcgcc tacatgaagt | 1260 |
| cggaatcgct agtaatcgcg gatcagcacg ccgcggtgaa tacgttcccg ggccttgtac | 1320 |
| acaccgcccg tcacaccacg agagtttgta acacccga | 1358 |

<210> SEQ ID NO 73
<211> LENGTH: 1460
<212> TYPE: DNA
<213> ORGANISM: Streptococcus sanguis

<400> SEQUENCE: 73

| | |
|---|---|
| tgatcctggc tcaggacgaa cgctggcggc gtgcctaata catgcaagta gaacgctgaa | 60 |
| gagaggagct tgctcttctt ggatgagttg cgaacgggtg agtaacgcgt aggtaacctg | 120 |
| cctggtagcg ggggataact attggaaacg atagctaata ccgcataaaa ttgattattg | 180 |
| catgataatt aattgaaaga tgcaattgca tcactaccag atggacctgc gttgtattag | 240 |
| ctagttggtg aggtaacggc tcaccaaggc gacgatacat agccgacctg agagggtgat | 300 |

| | |
|---|---|
| cggccacact gggactgaga cacggcccag actcctacgg gaggcagcag tagggaatct | 360 |
| tcggcaatgg ggggaaccct gaccgagcaa cgccgcgtga gtgaagaagg ttttcggatc | 420 |
| gtaaagctct gttgtaagag aagaacgggt gtgagagtgg aaagttcaca ctgtgacggt | 480 |
| atcttaccag aaagggacgg ctaactacgt gccagcagcc gcggtaatac gtaggtcccg | 540 |
| agcgttgtcc ggatttattg ggcgtaaagc gagcgcaggc ggttagataa gtctgaagtt | 600 |
| aaaggctgtg gcttaaccat agtatgcttt ggaaactgtt aacttgagt gcagaagggg | 660 |
| agagtggaat ccatgtgta gcggtgaaat gcgtagatat atggaggaac accggtggcg | 720 |
| aaagcggctc tctggtctgt aactgacgct gaggctcgaa agcgtgggga gcaaacagga | 780 |
| ttagataccc tggtagtcca cgccgtaaac gatgagtgct aggtgttagg ccctttccgg | 840 |
| ggcttagtgc cgcagctaac gcattaagca ctccgcctgg ggagtacgac cgcaaggttg | 900 |
| aaactcaaag gaattgacgg gggcccgcac aagcggtgga gcatgtggtt taattcgaag | 960 |
| caacgcgaag aaccttacca ggtcttgaca tccctctgac cgctctagag atagagtttt | 1020 |
| ccttcgggac agaggtgaca ggtggtgcat ggttgtcgtc agctcgtgtc gtgagatgtt | 1080 |
| gggttaagtc ccgcaacgag cgcaaccct attgttagtt gccatcattc agttgggcac | 1140 |
| tctagcgaga ctgccggtaa taaaccggag gaaggtgggg atgacgtcaa atcatcatgc | 1200 |
| cccttatgac ctgggctaca cacgtgctac aatggctggt acaacgagtc gcaagccggt | 1260 |
| gacggcaagc taatctctga aagccagtct cagttcggat tgtaggctgc aactcgccta | 1320 |
| catgaagtcg gaatcgctag taatcgcgga tcagcacgcc gcggtgaata cgttcccggg | 1380 |
| ccttgtacac accgcccgtc acaccacgag agtttgtaac acccgaagtc ggtgaggtaa | 1440 |
| ccgtaaggag ccagccgcct | 1460 |

<210> SEQ ID NO 74
<211> LENGTH: 1430
<212> TYPE: DNA
<213> ORGANISM: Streptococcus sanguis

<400> SEQUENCE: 74

| | |
|---|---|
| aggacgaacg ctggcggcgt gcctaataca tgcaaagtag aacgctgaag gaggagcttg | 60 |
| ctctttccgg atgagttgcg aacgggtgag taacgcgtag gtaacctgcc tggtagcggg | 120 |
| ggataactat tggaaacgat agctaatacc gcataacagt agatattgca tgatatctgc | 180 |
| ttgaaaggtg caattgcacc actaccagat ggacctgcgt tgtattagct agttggtgag | 240 |
| gtaacggctc accaaggcga cgatacatag ccgacctgag agggtgatcg ccacactgg | 300 |
| gactgagaca cggcccagac tcctacggga ggcagcagta gggaatcttc ggcaatggac | 360 |
| ggaagtctga ccgagcaacg ccgcgtgagt gaagaaggtt ttcggatcgt aaagctctgt | 420 |
| tgtaagagaa gaacgagtgt gagagtggaa agttcacact gtgacggtat cttaccagaa | 480 |
| agggacggct aactacgtgc cagcagccgc ggtaatacgt aggtcccgag cgttatccgg | 540 |
| atttattggg cgtaaagcga gcgcaggcgg ttagataagt ctgaagttaa aggctgtggc | 600 |
| ttaaccatag tacgctttgg aaactgttta acttgagtgc aagaggggag agtggaattc | 660 |
| catgtgtagc ggtgaaatgc gtagatatat ggaggaacac cggtggcgaa agcggctctc | 720 |
| tggcttgtaa ctgacgctga ggctcgaaag cgtgggagc aaacaggatt agataccctg | 780 |
| gtagtccacg ccgtaaacga tgagtgctag gtgttgggtc ctttccggga ctcagtgccg | 840 |
| cagctaacgc attaagcact ccgcctgggg agtacgaccg caaggttgaa actcaaagga | 900 |

```
attgacgggg gcccgcacaa gcggtggagc atgtggttta attcgaagca acgcgaagaa    960
ccttaccagg tcttgacatc cctctgaccg ctctagagat agagctttcc ttcgggacag   1020
aggtgacagg tggtgcatgg ttgtcgtcag ctcgtgtcgt gagatgttgg gttaagtccc   1080
gcaacgagcg caaccccctat tgttagttgc catcattcag ttgggcactc tagcgagact   1140
gccggtaata accggagga aggtggggat gacgtcaaat catcatgccc cttatgacct    1200
gggctacaca cgtgctacaa tggctggtac aacgagtcgc aagtcggtga cggcaagcta   1260
atctcttaaa gccagtctca gttcggattg taggctgcaa ctcgcctaca tgaagtcgga   1320
atcgctagta atcgcggatc agcacgccgc ggtgaatacg ttcccgggcc ttgtacacac   1380
cgcccgtcac accacgagag tttgtaacac ccgaagtcgg tgaggtaacc              1430
```

<210> SEQ ID NO 75
<211> LENGTH: 1428
<212> TYPE: DNA
<213> ORGANISM: Streptococcus sanguis

<400> SEQUENCE: 75

```
aggacgaacg ctggcggcgt gcctaataca tgcaagtaga acgctgaagg aggagcttgc     60
ttctctggat gagttgcgaa cgggtgagta acgcgtaggt aacctgcctg gtagcggggg    120
ataactattg gaaacgatag ctaataccgc ataatagtag atgttgcatg acatttgctt    180
aaaaggtgca attgcatcac taccagatgg acctgcgttg tattagctag ttggtgaggt    240
aacggctcac caaggcgacg atacatagcc gacctgagag ggtgatcggc cacactggga    300
ctgagacacg gcccagactc ctacgggagg cagcagtagg gaatcttcgg caatggacgg    360
aagtctgacc gagcaacgcc gcgtgagtga agaaggtttt cggatcgtaa agctctgttg    420
taagagaaga acgagtgtga gagtggaaag ttcacactgt gacggtatct taccagaaag    480
ggacggctaa ctacgtgcca gcagccgcgg taatacgtag gtcccgagcg ttgtccggat    540
ttattgggcg taaagcgagc gcaggcggtt agataagtct gaagttaaag gctgtggctt    600
aaccatagta cgctttggaa actgtttaac ttgagtgcaa gagggagag tggaattcca    660
tgtgtagcgg tgaaatgcgt agatatatgg aggaacaccg gtggcgaaag cggctctctg    720
gcttgtaact gacgctgagg ctcgaaagcg tggggagcaa acaggattag ataccctggt    780
agtccacgcc gtaaacgatg agtgctaggt gttagaccct tccggggtt tagtgccgca    840
gctaacgcat taagcactcc gcctggggag tacgaccgca aggttgaaac tcaaaggaat    900
tgacggggcc ccgcacaagc ggtggagcat gtggtttaat tcgaagcaac gcgaagaacc    960
ttaccaggtc ttgacatccc tctgaccgct ctagagatag agttttcctt cgggacagag   1020
gtgacaggtg gtgcatggtt gtcgtcagct cgtgtcgtga gatgtgggt taagtcccgc   1080
aacgagcgca acccctattg ttagttgcca tcattcagtt gggcactcta gcgagactgc   1140
cggtaataaa ccggaggaag gtggggatga cgtcaaatca tcatgcccct tatgacctgg   1200
gctacacacg tgctacaatg gctggtacaa cgagtcgcaa gccggtgacg gcaagctaat   1260
ctcttaaagc cagtctcagt tcggattgta ggctgcaact cgcctacatg aagtcggaat   1320
cgctagtaat cgcggatcag cacgccgcgg tgaatacgtt cccgggcctt gtacacaccg   1380
cccgtcacac cacgagagtt tgtaacaccc gaagtcggtg aggtaacc                1428
```

<210> SEQ ID NO 76
<211> LENGTH: 1508
<212> TYPE: DNA
<213> ORGANISM: Streptococcus sanguis

<400> SEQUENCE: 76

```
agagtttgat cctggctcag acgaacgctg gcggcgtgcc taatacatgc aagtagaacg      60
ctgaagagag gagcttgctc ttcttggatg agttgcgaac gggtgagtaa cgcgtaggta     120
acctgcctgg tagcggggga taactattgg aaacgatagc taataccgca tgatattaat    180
tatcgcatga taatcaattg aaagatgcaa ttgcatcact accagatgga cctgcgttgt     240
attagctagt tggtgaggta acggctcacc aaggcgacga tacatagccg acctgagagg    300
gtgatcggcc acactgggac tgagacacgg cccagactcc tacgggaggc agcagtaggg    360
aatcttcggc aatgggggga accctgaccg agcaacgccg cgtgagtgaa gaaggttttc    420
ggatcgtaaa gctctgttgt aagagaagaa cgggtgtgag agtggaaagt tcacactgtg    480
acggtatctt accagaaagg gacggctaac tacgtgccag cagccgcggt aatacgtagg    540
tcccgagcgt tgtccggatt tattgggcgt aaagcgagcg caggcggtta dataagtctg    600
aagttaaagg ctgtggctta accatagtat gctttggaaa ctgtttaact tgggtgcaga    660
aggggagagt ggaattccat gtgtagcggt gaaatgcgta gatatatgga ggaacaccgg    720
tggcgaaagc ggctctctgg tctgtaactg acgctgaggc tcgaaagcgt ggggagcaaa    780
caggattaga taccctggta gtccacgccg taaacgatga gtgctaggtg ttaggcccct    840
tccgggcctt agtgccgcag ctaacgcatt aagcactccg cctggggagt acgaccgcaa    900
ggttgaaact caaaggaatt gacggggggcc cgcacaagcg gtggagcatg tggttttaatt    960
cgaagcaacg cgaagaacct taccaggtct tgacatccct ctgaccgctc tagagataga   1020
gttttccttc gggacagaga tgacaggtgg tgcatggttg tcgtcagctc gtgtcgtgag   1080
atgttgggtc aagtcccgca acgagcgcaa cccctattgt tagttgccat cattgagttg   1140
ggcactctag cgagactgcc ggtaataaac cggaggaagg tggggatgac gtcaaatcat   1200
catgcccctt atgacctggg ctacacacgt gctacaatgg ctggtacaac gagtcgcaag   1260
ccggtgacgg caagctaatc tctgaaagcc agtctcagtt cggattgtag ctgcaactc    1320
gcctacatga agtcggaatc gctagtaatc gcggatcagc acgccgcggt gaatacgttc   1380
ccgggccttg tacaccgcc cgtcacacc acgagagttt gtaacacccg aagtcggtga   1440
ggtaaccgta aggagccagc cgcctaaggt gggatagatg attggggtga agtcgtaaca   1500
aggtaacc                                                            1508
```

<210> SEQ ID NO 77
<211> LENGTH: 1538
<212> TYPE: DNA
<213> ORGANISM: Streptococcus vestibularis

<400> SEQUENCE: 77

```
atgggagagt tgatcctgg ctcaggacga acgctggcgg cgtgcctaat acatgcaagt      60
agaacgctga agaggagc ttgctcttct tggatgagtt gcgaacgggt gagtaacgcg     120
taggtaacct gccttgtagc gggggataac tattggaaac gatagctaat accgcataac    180
aataggtgac acatgtcatt tatttgaaag gggcaattgc tccactacaa gatggacctg     240
cgttgtatta gctagtaggt gaggtaacgg ctcacctagg cgacgataca tagccgacct    300
gagagggtga tcgccacac tgggactgag acacggccca gactcctacg ggaggcagca     360
gtagggaatc ttcggcaatg ggggcaaccc tgaccgagca acgccgcgtg agtgaagaag    420
gttttcggat cgtaaagctc tgttgtaagt caagaacgag tgtgagagtg gaaagttcac    480
```

-continued

```
actgtgacgg tagcttacca gaagggacgg ctaactacgt gccagcagcc gcggtaatac      540
gtaggtcccg agcgttgtcc ggatttattg ggcgtaaagc gagcgcaggc ggtttgataa      600
gtctgaagtt aaaggctgtg gctcaaccat agttcgcttt ggaaactgtc aaacttgagt      660
gcagaagggg agagtggaat tccatgtgta gcggtgaaat gcgtagatat atggaggaac      720
accggtggcg aaagcggctc tctggtctgt aactgacgct gaggctcgaa agcgtgggga      780
gcgaacagga ttagataccc tggtagtcca cgccgtaaac gatgagtgct aggtgttgga      840
tcctttccgg gattcagtgc cgcagctaac gcattaagca ctccgcctgg ggagtacgac      900
cgcaaggttg aaactcaaag gaattgacgg gggcccgcac aagcggtgga gcatgtggtt      960
taattcgaag caacgcgaag aaccttacca ggtcttgaca tcccgatgct atttctagag     1020
atagaaagtt acttcggtac atcggtgaca ggtggtgcat ggttgtcgtc agctcgtgtc     1080
gtgagatgtt gggttaagtc ccgcaacgag cgcaacccct attgttagtt gccatcattc     1140
agttgggcac tctagcgaga ctgccggtaa taaaccggag gaaggtgggg atgacgtcaa     1200
atcatcatgc cccttatgac ctgggctaca cacgtgctac aatggttggt acaacgagtt     1260
gcgagtcggt gacggcaagc taatctctta aagccaatct cagttcggat tgtaggctgc     1320
aactcgccta catgaagtcg gaatcgctag taatcgcgga tcagcacgcc gcggtgaata     1380
cgttcccggg ccttgtacac accgcccgtc acaccacgag agtttgtaac acccgaagtc     1440
ggtgaggtaa cctttggag ccagccgcct aaggtgggat agatgattgg ggtgaagtcg     1500
taacaaggta gccgtatcgg aaggtgcggc tggatcac                             1538
```

METHOD OF DESIGNING PRIMER AND PROBE SETS, PRIMER AND PROBE SET DESIGNED BY THE METHOD, KIT COMPRISING THE SETS, COMPUTER READABLE MEDIUM RECORDED THEREON PROGRAM TO EXECUTE THE METHOD, AND METHOD OF IDENTIFYING TARGET SEQUENCE USING THE SETS

This application claims the benefit of Korean Patent Application No. 2005-0019064, filed on Mar. 8, 2005, in the Korean Intellectual Property Office, the disclosure of which is incorporated herein in its entirety by reference.

BACKGROUND OF THE INVENTION

1. Field of the Invention

The present invention relates to a method of designing primer and probe sets for identification of a target sequence, primer and probe sets designed by the method, a kit comprising the sets, a computer readable medium recorded thereon a program to execute the method, and a method of identifying a target sequence using the sets.

2. Description of the Related Art

A microarray is a substrate on which polynucleotides are immobilized at fixed locations. Such a microarray is well known in the art and examples thereof can be found in, for example, U.S. Pat. Nos. 5,445,934 and 5,744,305. Also, it is known that the microarray is generally manufactured using photolithography. When using photolithography, the polynucleotide microarray can be manufactured by repeatedly exposing an energy source to a discrete known region on a substrate, in which a monomer protected by a removable group is coated, to remove the protecting group, and coupling the deprotected monomer with another monomer protected by the removable group. In this case, the polynucleotide immobilized on a microarray is synthesized by extending monomers of the polynucleotide one by one. Alternatively, when using a spotting method, a microarray is formed by immobilizing previously-synthesized polynucleotides at fixed locations. Such methods of manufacturing a microarray are disclosed in, for example, U.S. Pat. Nos. 5,744,305, 5,143,854, and 5,424,186. These documents related to microarrays and methods of manufacturing the same are incorporated herein in their entirety by reference.

A typical method of searching or identifying the genotype of a target sequence using a microarray includes amplifying the target sequence using a certain primer, applying the amplified target sequence to the microarray, hybridizing the amplified target sequence with a polynucleotide (also called "a probe", "a probe nucleic acid", or "a probe polynucleotide") which is immobilized on the microarray, washing the microarray to remove a non-specific reaction, and detecting a fluorescent signal due to the formation of a target sequence-probe hybrid. In the method of identifying a target sequence, the obtained results vary according to how to design the primer and probe. Thus, a method of efficiently designing a primer and a probe for identification of a target sequence is urgently required.

The conventional method of designing a primer and a probe is based on multiple sequence alignment. The multiple sequence alignment is to align three or more sequences which include mutation such as substitution, addition or deletion such that the number of identical base alignment is greatest. FIG. 2 is a schematic diagram of the conventional multiple sequence alignment. Referring to FIG. 2, after aligning target sequences such that the number of identical base alignment is maximum, common regions (a/c and e/g) are selected as primers and unique regions (b, d, h, f, i) are selected as probes to design primer and probe sets.

In the conventional method of designing primer and probe sets, since only a specific sequence which hybridizes with each target sequence but does not cross-hybridize with other sequences is selected as a probe, when the sequence homology between target sequences is high or the number of target sequences to be identified is large, a specific probe cannot be designed. Moreover, when a universal primer cannot be designed, an optimum primer for a subgroup cannot be directly proposed and a separate design method is required. Even though a primer and a probe can be designed, additional information for design is required and a processing rate is reduced.

For example, to identify species of bacteria in a sample, a primer and a probe have been designed using a 16S rRNA site, which is one of consensus sequences, on the basis of the multiple sequence alignment. That is, after aligning the 16S rRNA site according to the multiple sequence alignment, common sequences in the species are used as primers and unique sequences in the species are used as probes. Such a method can be used to identify several species of bacteria, but is limited in identification of many species of bacteria since the 16S rRNA site is highly conserved.

The inventors of the present invention found that primer and probe sets capable of rapidly and accurately identifying a number of target sequences can be readily designed by repeating an operation of preparing subsequence sets of target sequences and an operation of selecting two subsequence sets in which the number of subsequences having a high homology is greatest, and thus completed the present invention.

SUMMARY OF THE INVENTION

The present invention provides a method of designing primer and probe sets for identification of a target sequence by amplification and hybridization.

The present invention also provides primer and probe sets designed according to the method.

The present invention also provides a kit for identification of a target sequence, including the primer and probe sets.

The present invention also provides a computer readable medium recorded thereon a program to execute the method.

The present invention also provides a method of identifying a target sequence using the primer and probe sets.

According to one aspect of the present invention, there is provided a method of designing primer and probe sets for identification of a target sequence by amplification and hybridization, including: (a) preparing subsequence sets by cleaving a plurality of target sequences according to a predetermined criterion while sliding 1 bp by 1 bp so as to include all possible subsequences; (b) selecting two subsequence sets, in which the number of subsequences having homology greater than a predetermined level is greatest by comparing the subsequence sets; (c) selecting subsequences which have homology greater than a predetermined level in the two subsequence sets as a common subsequence set and selecting the remaining subsequences as probes; (d) repeatedly performing the operations (b) and (c) on the subsequence sets (excluding the two subsequence sets) and the common subsequence set until there are no subsequences having homology greater than a predetermined level between subsequence sets; and (e) selecting subsequences of common subsequence sets which contain no subsequences having homology greater than a predetermined level as primers.

In the method of designing primer and probe sets, the criterion in the operation (a) may be at least one selected from the group consisting of a base length, a hybridization melting point (Tm), a GC content, self-alignment, a mutation position, a repeating sequence level, and a base composition of at the 3' end.

In the method of designing primer and probe sets, the selecting of two subsequence sets in the operation (b) may be carried out considering thermodynamic characteristics and position information.

According to another aspect of the present invention, there is provided primer and probe sets designed using the method.

According to another aspect of the present invention, there is provided a microarray in which the probe set is immobilized on a substrate and a kit for identification of a target sequence, including the primer set.

The substrate may be coated with an active group selected from the group consisting of amino-silane, poly-L-lysine, and aldehyde.

The substrate may be a silicon wafer, glass, quartz, metal, or plastic.

According to another aspect of the present invention, there is provided a computer readable medium recorded thereon a program to execute the method.

According to another aspect of the present invention, there is provided a method of identifying a target sequence using the primer and probe sets.

The method of identifying a target sequence may include: amplifying a target sequence using the primer set; hybridizing the amplified target sequence with the probe set; washing and removing a non-specific reaction; and detecting a fluorescent signal due to hybrid formation.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

According to an embodiment of the present invention, there is provided a method of designing primer and probe sets for identification of a target sequence by amplification and hybridization.

Figure 1:
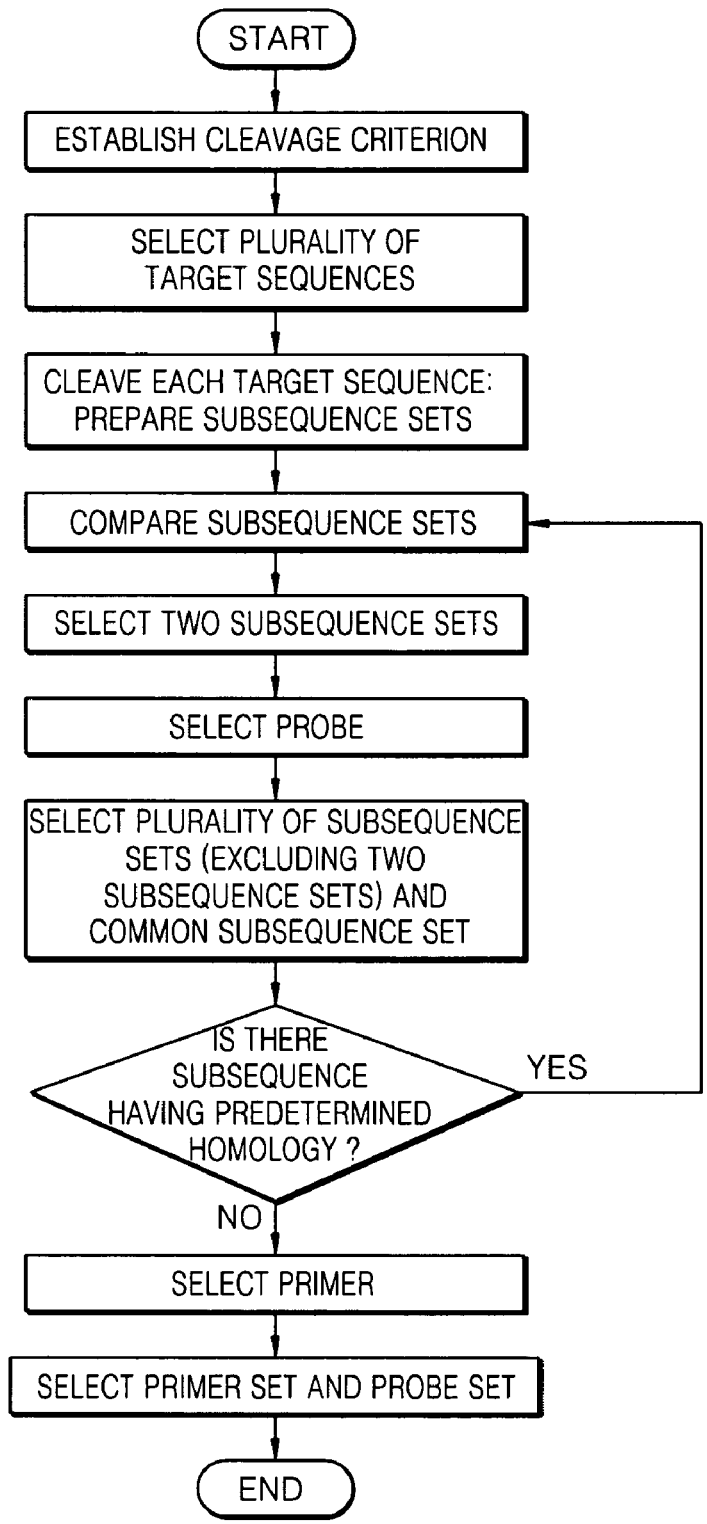
FIG. 1 is a flow chart of a method of designing primer and probe sets according to an embodiment of the present invention.
Figure 2:
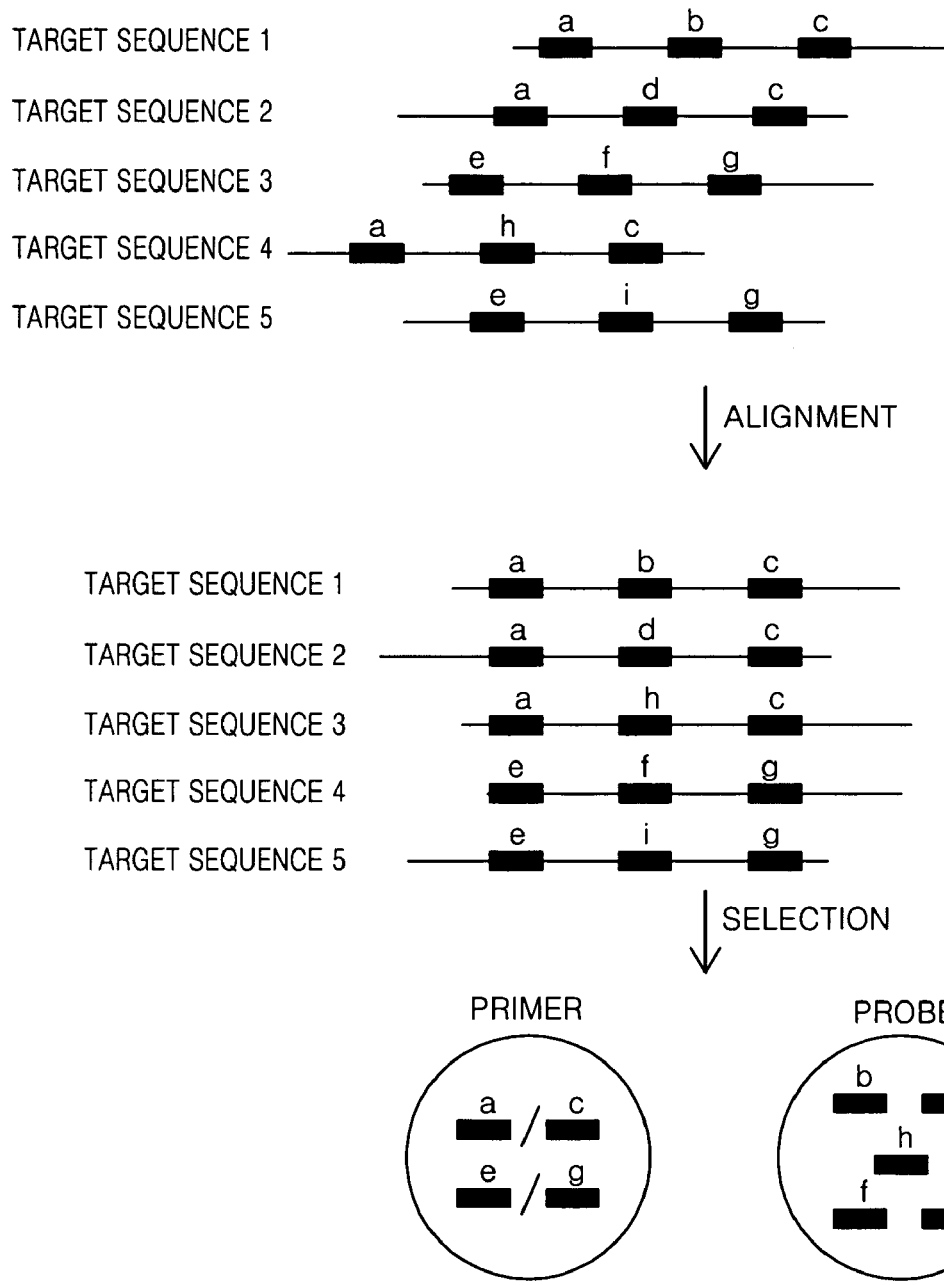
FIG. 2 is a schematic diagram of conventional multiple sequence alignment.

FIG. 1 is a flow chart illustrating a method of designing primer and probe sets according to an embodiment of the present invention.

A method of designing primer and probe sets according to an embodiment of the present invention includes an operation (a) of preparing subsequence sets by cleaving a plurality of target sequences according to a predetermined criterion while sliding 1 bp by 1 bp so as to include all possible subsequences.

As used herein, the term "target sequence" refers to a polynucleotide selected to be identified by binding to a probe. Examples of the target sequence include genome DNA, a DNA fragment cleaved by a restriction enzyme, and a PCR product. A genome DNA fragment obtained by amplifying a specific region of genome DNA using a specific primer through a polymerase chain reaction (PCR) is generally used. The method of the present embodiment is to design primer and probe sets which can be applied to two or more target sequences.

The predetermined criterion may be a typical criterion for selection of a primer or a probe. That is, the criterion may be at least one selected from the group consisting of a base length, a hybridization melting point (Tm), a GC content, self-alignment, a mutation position, a repeating sequence level, and a base composition at the 3' end. The predetermined criterion may be readily established according to experimental conditions using the primer or probe sets designed by the method of the present embodiment. For example, when a hybridization temperature is 72-76° C., a base sequence of 18-25 bp may be set. To design more effective primer and probe sets, the method may further include selecting a GC content of 30-70% and selecting primer and probe sets having G or C at the 3' end.

Figure 3:
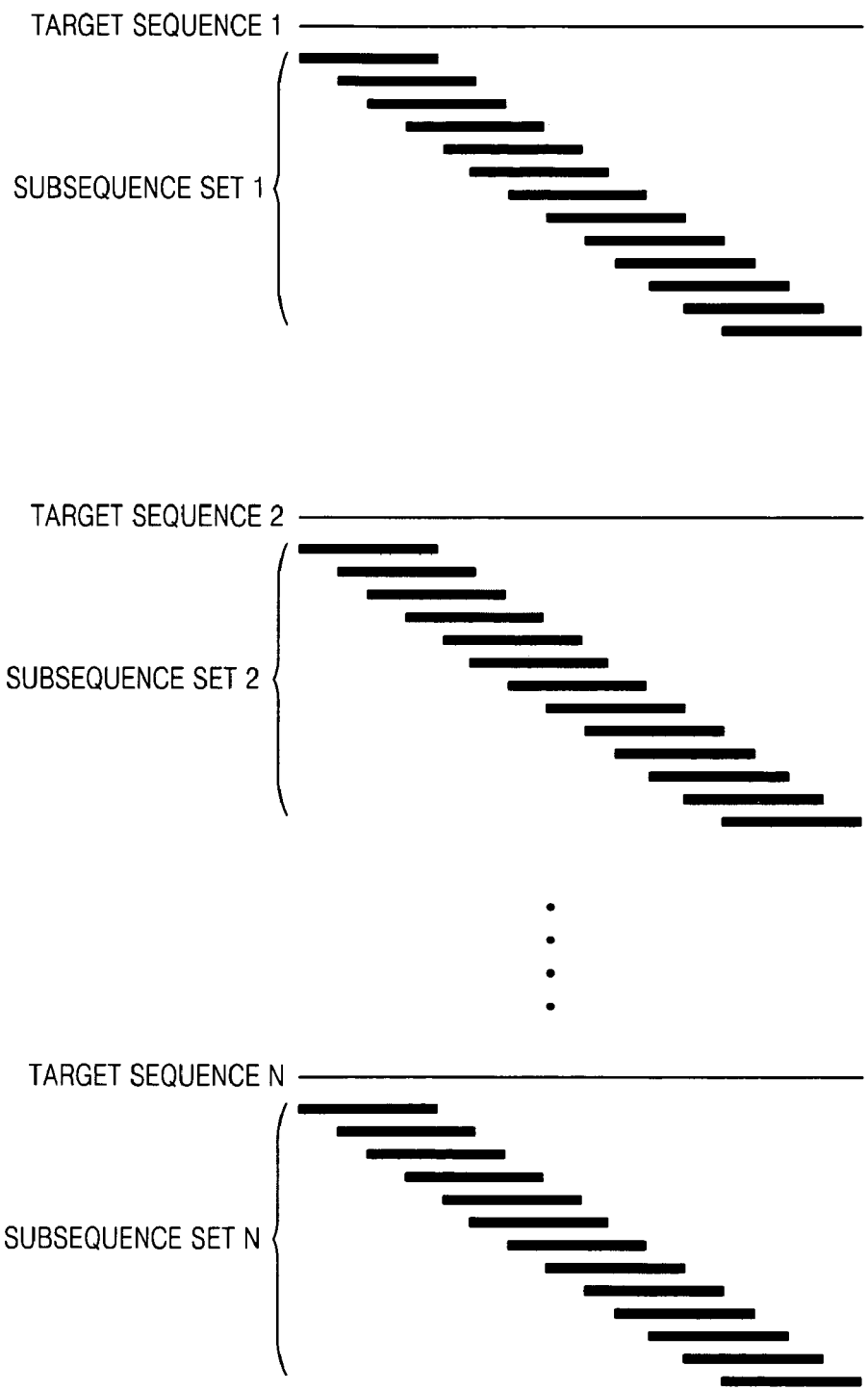
FIG. 3 is a schematic diagram of an operation of preparing a subsequence set in a method of designing primer and probe sets according to an embodiment of the present invention.

FIG. 3 is a schematic diagram of an operation of preparing subsequence sets in the method of designing primer and probe sets according to an embodiment of the present invention.

Referring to FIG. 3, each target sequence is cleaved while sliding 1 bp by 1 bp to prepare subsequence sets including a plurality of subsequences. In Examples of the present invention, a target sequence is cleaved such that each subsequence has a base length of 20 bp.

After preparing the subsequence sets, an operation (b) of selecting two subsequence sets which have the greatest number of subsequences having homology greater than a predetermined level by comparing the subsequence sets is performed.

The search of homology may be performed using a method known to those skilled in the art, for example, using a homology search program. Herein, homology greater than a predetermined level can be readily established by those skilled in the art according to experimental conditions, and thus, is not particularly restricted. When simply comparing homology of character string, the criterion of homology may vary according to a tolerance of mismatched character. Homology may be determined considering hybridization of 80% or greater. In addition to homology of character string itself, homology may be determined by free energy when hybridization is accomplished using a thermodynamic model such as a nearest-neighbor model.

The selection of two subsequence sets in the operation (b) may be performed considering thermodynamic characteristics and position information.

The thermodynamic characteristics are considered to determine a temperature at which hybridization occurs by predicting hybridization characteristics. When a collection of oligonucleotides which have an equal length is formed as in Examples of the present invention, accurate hybridization characteristics cannot be predicted using only the length. Thus, this process is necessary. Meanwhile, when a collection of oligonucleotides which have different lengths from each other is formed (for example, when Tm is set at 65° C. and a collection of similar oligonucleotides is formed, part having a high GC content is short and part having a low GC content is long), this process is not necessary.

The position information is considered to allow a probe to be placed between primers. That is, this process is required when determining actual primer and probe after identifying all relationships between sequence sets.

Next, an operation (c) of selecting subsequences which have homology greater than a predetermined level in the two subsequence sets as a common subsequence set and selecting the remaining subsequences as probes is performed.

Herein, the term "the common subsequence set" refers to a collection of polynucleotides including subsequences which have homology greater than a predetermined level among subsequences of the two selected subsequence sets (one subsequence set and one common subsequence set, or two common subsequence set, when this operation is repeated). For example, when each of the two subsequence sets includes 1000 subsequences and 900 pairs of subsequences have homology of 90% or greater, the 900 subsequences may be selected as a common sequence set (based on homology of 90% or greater) and each 100 subsequences having homology less than 90% may be selected as probes. Also, when 700 pairs of subsequences among 1000 pairs of subsequences have homology of 100%, the 700 subsequences may be selected as a common subsequence set (based on homology of 100%) and each 300 subsequences having homology less than 100% may be selected as probes.

All the probes may be used, but some of the probes may also be selected and used. In the method of the present embodiment, the probe may be selected using conventionally known methods. More specifically, a criterion for selecting a probe DNA is established in the same manner as the criterion for target sequence cleavage described above, DNA sequences which meet the criterion are selected, and the most preferable sequence is selected as the probe DNA after investigating whether the selected DNA sequences meets the above criterion and other requirements. That is, the most preferable one among the selected probes is selected as a probe sequence. Two or more probe DNAs can also be selected with respect to a target DNA as long as they can specifically bind to the target DNA.

Next, an operation (d) of repeatedly performing the operations (b) and (c) on the plurality subsequence sets (excluding the two subsequence sets) and the common subsequence set until there are no subsequences having homology greater than a predetermined level between subsequence sets is performed.

That is, the plurality subsequence sets in which the common subsequence set substitutes for the two selected subsequence sets are compared again to select two (common) subsequence sets which have the greatest number of subsequences having homology greater than a predetermined level. Then, subsequences having homology greater than a predetermined level among subsequences of the two (common) subsequence sets are selected as a common subsequence set and the remaining subsequences are selected as probes. These operations are repeated until there are no subsequences having homology greater than a predetermined level between (common) subsequence sets.

Subsequently, an operation (e) of selecting subsequences of common subsequence sets which contain no subsequences having homology greater than a predetermined level as primers is performed. When only one common subsequence set is remained after performing these operations, subsequences of the common subsequence set are selected as primers. In addition, when two or more common subsequence sets are remained, subsequences of each common subsequence set are selected as primers. All the primers may be used, but some of the primers may also be selected and used.

Figure 4:
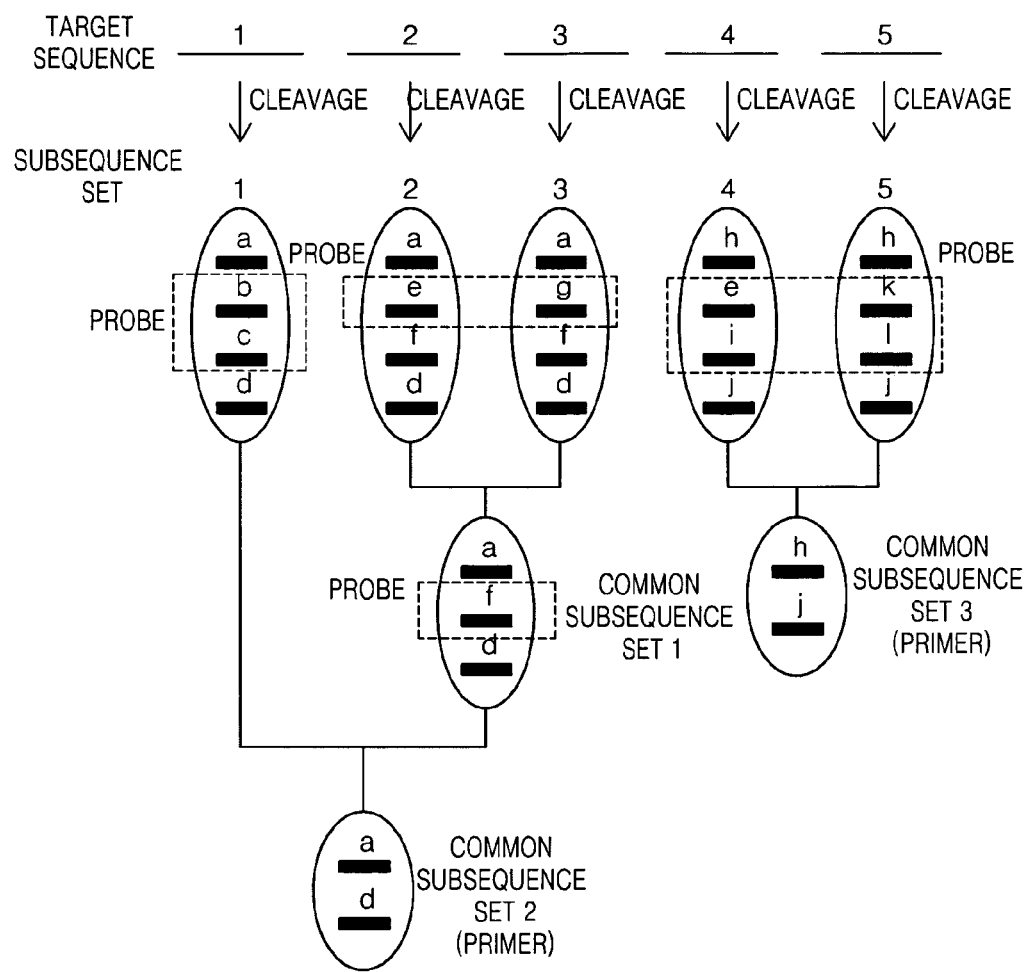
FIG. 4 is an example of a method of designing primer and probe sets according to an embodiment of the present invention.

FIG. 4 is a schematic diagram of the method of designing primer and probe sets according to an embodiment of the present invention.

Although five target sequences are used in this case, the number of target sequences is not limited thereto. It will be understood by those skilled in the art that as the number of target sequences increases, the present invention is more effective.

Referring to FIG. 4, 5 target sequences are cleaved according to a predetermined criterion while sliding 1 bp by 1 bp to provide each subsequence set. Although each subsequence set includes 4 subsequences in the FIG. 4, the number of actual subsequences will be much more.

5 subsequence sets respectively including 4 subsequences are compared and subsequence sets 2 and 3 which have the greatest number of subsequences having homology greater than a predetermined level (three subsequences a, f and d) are selected. Next, the three subsequences a, f and d are selected as a common subsequence set 1 and subsequences e and g are selected as probes.

Then, a plurality of subsequence sets in which the common subsequence set substitutes for the two subsequence sets, i.e., a subsequence set 1, a common subsequence set 1, a subsequence set 4, and a subsequence set 5 are compared again to select two (common) subsequence sets in which the number of subsequences having homology greater than a predetermined level is greatest. In FIG. 4, the number of subsequences having homology in the subsequence set 1 and the common subsequence set 1 (2: subsequences a and d) is equal to the number of subsequences having homology in the subsequence sets 4 and 5 (2: subsequences h and j). Thus, in the case of the subsequence set 1 and the common subsequence set 1, subsequences a and d are selected as a common subsequence set 2 and subsequences b, c and f are selected as probes. In the case of the subsequence sets 4 and 5, subsequences h and j are selected as a common subsequence set 3 and subsequences e, l, k and l are selected as probes.

Then, although subsequences of the common subsequence sets 2 and 3 are compared to select two common subsequence sets in which the number of subsequences having homology greater than a predetermined level, there are no subsequences having homology greater than a predetermined level. Thus, subsequences a, d, h and j of the common subsequence sets 2 and 3 are selected as primers.

According to another embodiment of the present invention, there is provided a primer and probe sets designed using the method described above.

According to another embodiment of the present invention, there is provided a microarray having a substrate on which the probe set is immobilized and a kit for identification of a target sequence including the primer set.

The microarray may be manufactured using the probe set according to a typical method known to those skilled in the art. That is, the substrate may be coated with an active group selected from the group consisting of amino-silane, poly-L- lysine, and aldehyde. The substrate may be a silicon wafer, glass, quartz, metal, or plastic. The probe set may be immobilized on the substrate using a piezoelectric micropipetting method, a pin-shaped spotter, etc.

According to another embodiment of the present invention, there is provided a method of identifying a target sequence using the primer and probe set.

The method of identifying a target sequence may include: amplifying the target sequence using the primer set; hybridizing the amplified target sequence with the probe set; washing and removing a non-specific reaction; and detecting a fluorescent signal due to hybrid formation.

According to another embodiment of the present invention, there is provided a computer readable medium recorded thereon a program to execute the method of designing primer and probe sets.

The invention can also be embodied as computer (all devices with a data processing capability) readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices The present invention will be described in greater detail with reference to the following example. The following example is for illustrative purposes only, and is not intended to limit the scope of the invention.

EXAMPLE 1

Design of Primer and Probe Sets for Identification of 10 Species of Bacteria

In the present Example, primer and probe sets were designed using 16S rRNA sequences of 10 species of bacteria belonging to streptococcus species among bacteria related to sepsis or bacteremia, as set forth in Table 1, as target sequences. Sequence data of 77 sequences for 10 species are based on opened data of rRNA database which is called RDP2.

TABLE 1

| Species | 16S rRNA sequence |
|---|---|
| Streptococcus aglactiae | SEQ ID No: 1-SEQ ID No: 4 |
| Streptococcus bovis | SEQ ID No: 5-SEQ ID No: 19 |
| Streptococcus intermedius | SEQ ID No: 20 |
| Streptococcus mitis | SEQ ID No: 21-SEQ ID No: 30 |
| Streptococcus oralis | SEQ ID No: 31-SEQ ID No: 34 |
| Streptococcus pneumoniae | SEQ ID No: 35-SEQ ID No: 44 |
| Streptococcus pyogenes | SEQ ID No: 45-SEQ ID No: 69 |
| Streptococcus salivaruis | SEQ ID No: 70 |
| Streptococcus sanguinis | SEQ ID No: 71-SEQ ID No: 76 |
| Streptococcus vestibularis | SEQ ID No: 77 |

Figure 5:
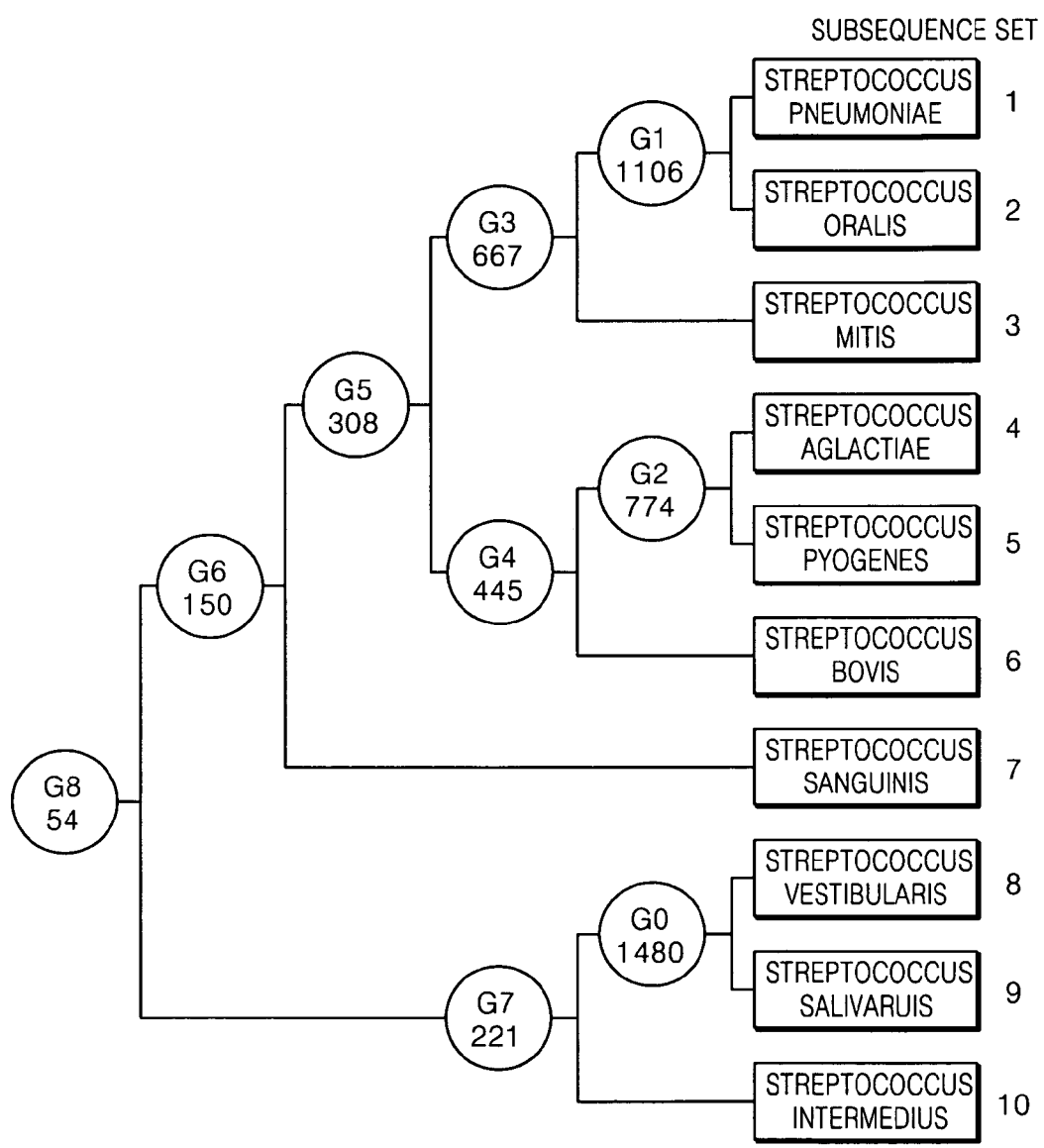
FIG. 5 is a schematic diagram of a method of designing primer and probe sets carried out in an Example of the present invention (homology upon comparison of a subsequence set; 100%)

FIG. 5 is a schematic diagram of the method of designing primer and probe sets performed in the present Example. First, 77 sequences of 16S rRNA, as described in Table 1, were cleaved to have a 20 bp length while sliding 1 bp by 1 bp to provide 77 subsequence sets, each of which had a number of sequences. Then, when one species had a number of sequences, only a common subsequence for the sequences was selected as a species representative subsequence and 10 subsequence sets were prepared.

10 subsequence sets were compared to select a subsequence 8 of *streptococcus vestibularis* and a subsequence 9 of *streptococcus salivaruis* in which the number of subsequences having 100% homology was greatest (1,480). 1,480 subsequences were selected as a common subsequence set G0 and the remaining subsequences which did not have homology were selected as probes. Then, subsequence sets 1-7, the common subsequence set G0, and a subsequence set 10 were compared to select a subsequence 1 of *streptococcus pneumoniae* and a subsequence 2 of *streptococcus oralis* in which the number of subsequences having 100% homology was greatest (1,106). 1,106 subsequences were selected as a common subsequence set G1 and the remaining subsequences which did not have homology were selected as probes. Subsequently, the above-described operations were repeated on the common subsequence set G1, subsequence sets 3-7, the common subsequence set G0, and the subsequence set 10. As a result, only the common subsequence set G8 having 54 subsequences was remained. The 54 subsequences were selected as primers.

EXAMPLE 2

Design of Primer and Probe Sets for Identification of 10 Species of Bacteria

The present Example was carried out in the same manner in Example 1, except that two subsequence sets were selected on the basis on homology of 90% or greater (allow 1-2 mismatches among 20 bp), instead of 100% homology.

Figure 6:
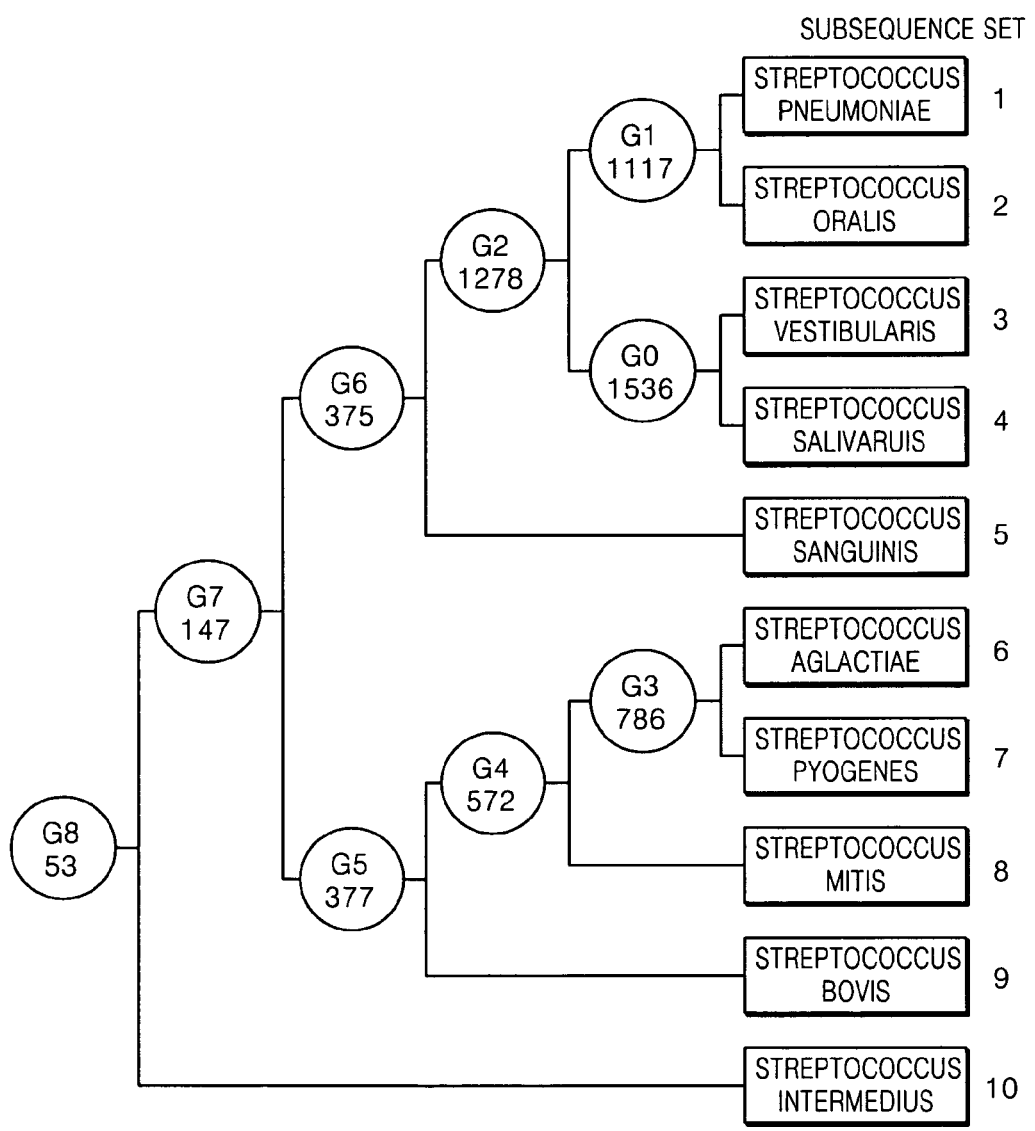
FIG. 6 is a schematic diagram of a method of designing primer and probe sets carried out in another Example of the present invention (homology upon comparison of a subsequence set; 90% or greater).

FIG. 6 is a schematic diagram of the method of designing primer and probe sets performed in the present Example. 10 subsequence sets were compared to select a subsequence 3 of *streptococcus vestibularis* and a subsequence 4 of *streptococcus salivaruis* in which the number of subsequences having homology of 90% or greater was greatest (1,536). 1,536 subsequences were selected as a common subsequence set G0 and the remaining subsequences which had homology less than 90% were selected as probes. Then, subsequence sets 1-2, the common subsequence set G0, and subsequence sets 5-10 were compared to select a subsequence 1 of *streptococcus pneumoniae* and a subsequence 2 of *streptococcus oralis* in which the number of subsequences having homology of 90% or greater was greatest (1,117). 1,117 subsequences were selected as a common subsequence set G1 and the remaining subsequences which had homology less than 90% were selected as probes. Subsequently, the above-described operations were repeated on common subsequence sets G0 and G1, and the subsequence sets 5-10. As a result, only the common subsequence set G8 having 53 subsequences was remained. The 53 subsequences were selected as primers.

EXAMPLE 3

Determination of Rate of the Method of Designing Primer and Probe Sets According to the Present Invention The methods of designing primer and probe sets, which was carried out in Examples 1 and 2, were written as computer programs and the rate of designing primer and probe sets of the program for 10 species of bacteria of Table 1 was compared with T-Coffee [C. Notredame, D. Higgins, J. Heringa, T-Coffee: A novel method for multiple sequence alignments, *Journal of Molecular Biology*, Vol 302, pp 205-217, 2000; http://igs-server.cnrs-mrs.fr/~cnotred/Projects_home_page/t_coffee_home_page.html], Clustalw (Chenna R, Sugawara H, Koike T, Lopez R, Gibson T J, Higgins D G, Thompson J D., Multiple sequence alignment with the Clustal series of programs. *Nucleic Acids Res.* 2003 July; 31(13), 3497-500; ftp://ftp.ebi.ac.uk/pub/software/unix/clustalw/) and Muscle (Edgar, Robert C. (2004), MUSCLE: multiple sequence alignment with high accuracy and high throughput, *Nucleic*

*Acids Research* 32(5), 1792-97; http://www.drive5.com/muscle/), which embodied the conventional multiple sequence alignment. The multiple sequence alignment is used as a middle step for designing primers and probes based on multiple sequence alignment and additional analysis is required to finally obtain a primer and probe list. However, since there is no program including such a function until now, the method of the present invention was compared with the multiple sequence alignment.

Each program was embodied under the same computer specifications (Intel Pentium III Xeon 700 MHz, 4 GB memory, GNU/Debian Linux).

The results are set forth in Table 2. Referring to Table 2, when T-Coffee was used, the computer stopped at 31,641 seconds before completing sequence alignment due to memory shortage. In the case of Clustalw and Muscle, it took 2,578 seconds and 60 seconds, respectively, to align sequences. Meanwhile, total time taken to perform Example 1 in which 100% homology was set was 17.4 seconds and total time taken to perform Example 2 in which homology of 90% or greater was set was 71.8 seconds. Thus, it can be seen that the method of the present invention has higher rate than conventional methods.

TABLE 2

| Program | Time (sec) | Note |
| --- | --- | --- |
| Coffee* | 31,641 | Stopped due to memory shortage |
| Clustalw* | 2,578 | |
| Muscle* | 60 | |
| Example 1 | 17.4 | 20 bp, 100 homology |
| Example 2 | 71.8 | 20 bp, homology of 90% or greater |

*represents only the time taken to align sequences

According to the present invention, primer and probe sets capable of identifying rapidly and accurately a number of target sequences can be readily designed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of designing primer and probe sets for identification of a target sequence by amplification and hybridization, comprising:

(a) preparing a subsequence set for each target sequence in a plurality of target sequences, wherein a subsequence set for a target sequence is prepared by cleaving the target sequence into subsequences meeting a predetermined criterion wherein each base pair (bp) of the target sequence is a start site for a subsequence meeting the predetermined criterion;

(b) comparing the subsequence sets pairwise for homology greater than or equal to a predetermined level to determine a number of subsequences in each pair of subsequence sets having homology greater than or equal to the predetermined level;

(c) selecting the pair of subsequence sets for which the number of subsequences having homology greater than the predetermined level is greatest among all the subsequence sets;

(d) selecting subsequences which have homology greater than the predetermined level in the selected pair of subsequence sets as a common subsequence set for the selected pair of subsequence sets and selecting the remaining subsequences in the selected pair of subsequence sets as probes for the selected pair of subsequence sets;

(e) replacing the selected pair of subsequence sets with the common subsequence set for the selected pair of subsequence sets;

(f) performing operations (b) to (e) on pairs of subsequence sets consisting of unselected subsequence sets and common subsequence sets until there is only one common subsequence set remaining or there are no subsequences having homology greater than or equal to the predetermined level between any pairs of subsequence sets remaining; and (g) selecting subsequences of remaining subsequence sets as primers for the plurality of target sequences, wherein the method is executed by a suitably-programmed computer.

2. The method of claim 1, wherein the predetermined criterion in operation (a) is at least one selected from the group consisting of a base length, a hybridization melting point (Tm), a GC content, self-alignment, a mutation position, a repeating sequence level, and a base composition at the 3' end.

3. The method of claim 1, wherein selecting two subsequence sets in operation (c) further comprises considering thermodynamic characteristics and position information for subsequences in the subsequence sets.

4. A computer readable recording medium recorded thereon a program to execute the method of claim 1.

5. The method of claim 1, wherein selecting subsequences of common subsequence sets which contain no subsequences having homology greater than or equal to the predetermined level as primers for the plurality of target sequences further comprises considering thermodynamic characteristics and position information for subsequences of common subsequence sets having homology greater than or equal to the predetermined level.

6. The method of claim 1, wherein selecting the remaining subsequences in the selected two subsequence sets as probes for the selected two subsequence sets in operation (d) further comprises considering thermodynamic characteristics and position information for the subsequences.

* * * * *